US012733917B2

(12) United States Patent
Xu et al.

(10) Patent No.: US 12,733,917 B2
(45) Date of Patent: Sep. 15, 2026

(54) TORQUE BALANCING DEVICE, SELF-BALANCING JOINT, AND SURGICAL ROBOT

(71) Applicant: BEIJING SURGERII ROBOTICS COMPANY LIMITED, Beijing (CN)

(72) Inventors: Kai Xu, Beijing (CN); Tiening Ma, Beijing (CN); Yi Sun, Beijing (CN); Ke Xiong, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 1113 days.

(21) Appl. No.: 17/790,477

(22) PCT Filed: Dec. 21, 2020

(86) PCT No.: PCT/CN2020/138009

§ 371 (c)(1),
(2) Date: Jun. 30, 2022

(87) PCT Pub. No.: WO2021/136003

PCT Pub. Date: Jul. 8, 2021

(65) Prior Publication Data

US 2023/0042160 A1 Feb. 9, 2023

(30) Foreign Application Priority Data

Dec. 30, 2019 (CN) ......................... 201911391727.6
Dec. 30, 2019 (CN) ......................... 201911391792.9
(Continued)

(51) Int. Cl.
*A61B 17/00* (2006.01)
*A61B 34/00* (2016.01)
(Continued)

(52) U.S. Cl.
CPC .............. *A61B 17/00* (2013.01); *A61B 34/30* (2016.02); *B25J 17/00* (2013.01); *B25J 19/0016* (2013.01);
(Continued)

(58) Field of Classification Search
CPC ......... A61B 17/00; A61B 34/30; A61B 34/25; B25J 17/00; B25J 19/0016; F16C 11/04; F16F 3/04; F16F 15/00
See application file for complete search history.

(56) References Cited

U.S. PATENT DOCUMENTS 6,328,487 B1 12/2001 Cartoni
2007/0180772 A1 8/2007 Finke
(Continued)

FOREIGN PATENT DOCUMENTS

CN 101234489 A 8/2008
CN 201743327 U 2/2011
(Continued)

OTHER PUBLICATIONS

Search Report issued in corresponding Chinese Application No. 2019113917276, mailed on Nov. 29, 2021, 2 pages.
(Continued)

*Primary Examiner* — Terence Boes
(74) *Attorney, Agent, or Firm* — Bayes PLLC

(57) ABSTRACT

A torque balancing device, a self-balancing joint and a surgical robot are provided. The torque balancing device includes a first body, a second body, an elastic part and a transmission part, the first body includes a first connection end and a first opposite end opposite to the first connection end, the second body includes a second connection end and a second opposite end opposite to the second connection end, the second connection end of the second body is rotatably connected to the first connection end of the first
(Continued)

body, the elastic part is provided in the first body, and the transmission part is connected to the second body and the elastic part.

8 Claims, 41 Drawing Sheets

(30) Foreign Application Priority Data

| | | |
|---|---|---|
| Dec. 30, 2019 | (CN) | 201911391794.8 |
| Dec. 30, 2019 | (CN) | 201911391803.3 |
| Dec. 30, 2019 | (CN) | 201911393239.9 |
| Dec. 30, 2019 | (CN) | 201911393257.7 |
| Dec. 30, 2019 | (CN) | 201911393258.1 |
| Dec. 30, 2019 | (CN) | 201922431993.9 |
| Dec. 30, 2019 | (CN) | 201922434125.6 |

(51) Int. Cl.

| | |
|---|---|
| ***A61B 34/30*** | (2016.01) |
| ***B25J 17/00*** | (2006.01) |
| ***B25J 19/00*** | (2006.01) |
| ***F16C 11/04*** | (2006.01) |
| ***F16F 3/04*** | (2006.01) |
| ***F16F 15/00*** | (2006.01) |

(52) U.S. Cl.

CPC ................ *F16C 11/04* (2013.01); *F16F 3/04* (2013.01); *F16F 15/00* (2013.01); *A61B 34/25* (2016.02)

(56) References Cited

U.S. PATENT DOCUMENTS

| | | | | |
|---|---|---|---|---|
| 2014/0202276 | A1 | 7/2014 | Song et al. | |
| 2015/0351857 | A1* | 12/2015 | Vander Poorten | B25J 18/007 606/130 |
| 2017/0014993 | A1 | 1/2017 | Barnes | |

FOREIGN PATENT DOCUMENTS

| | | | |
|---|---|---|---|
| CN | 201747760 | U | 2/2011 |
| CN | 202048864 | U | 11/2011 |
| CN | 103195859 | A | 7/2013 |
| CN | 203308440 | U | 11/2013 |
| CN | 203645460 | U | 6/2014 |
| CN | 104398366 | A | 3/2015 |
| CN | 104546147 | A | 4/2015 |
| CN | 204446127 | U | 7/2015 |
| CN | 105108777 | A | 12/2015 |
| CN | 205001781 | U | 1/2016 |
| CN | 205036718 | U | 2/2016 |
| CN | 106078793 | A | 11/2016 |
| CN | 106166738 | A | 11/2016 |
| CN | 106313115 | A | 1/2017 |
| CN | 205988396 | U | 3/2017 |
| CN | 107795615 | A | 3/2018 |
| CN | 107901032 | A | 4/2018 |
| CN | 108025445 | A | 5/2018 |
| CN | 108081310 | A | 5/2018 |
| CN | 109386557 | A | 2/2019 |
| CN | 208784914 | U | 4/2019 |
| CN | 109730781 | A | 5/2019 |
| CN | 212028411 | U | 11/2020 |
| CN | 212072015 | U | 12/2020 |
| CN | 212096416 | U | 12/2020 |
| CN | 212096422 | U | 12/2020 |
| CN | 212346589 | U | 1/2021 |
| CN | 212666100 | U | 3/2021 |
| CN | 212672213 | U | 3/2021 |
| DE | 19961398 | A1 | 6/2001 |
| DE | 102007003470 | A1 | 7/2008 |
| EP | 0595291 | A1 | 5/1994 |
| EP | 1384907 | A2 | 1/2004 |
| GB | 158867 | A | 3/1922 |
| GB | 747856 | A | 4/1956 |
| KR | 20120091940 | A | 8/2012 |
| KR | 20160099301 | A | 8/2016 |
| TW | M269376 | U | 7/2005 |
| WO | 2011149260 | A2 | 12/2011 |

OTHER PUBLICATIONS

Search Report issued in corresponding International Application No. PCT/CN/2020/138009, mailed on Mar. 15, 2021, 5 pages.
Extended European Search Report in related European Patent Application No. 20909879.7 dated Apr. 18, 2024 (14 pages).
Search Report in related Chinese Application No. 2019113917948 dated Sep. 2, 2025 (2 pages).
Search Report issued in corresponding Chinese Application No. 2020800891531 mailed on May 11, 2023, 3 pages.
Search Report from related Chinese Application No. 2019113932577 dated Jul. 4, 2025 (3 pages).
Search Report from related Chinese Application No. 2019113918033 dated Jul. 13, 2025 (2 pages).
Search Report from related Chinese Application No. 2019113932581 dated Jul. 13, 2025 (2 pages).
Search Report from related Chinese Application No. 2019113932399 dated Aug. 1, 2025 (3 pages).
Search Report in related Chinese Application No. 2019113917929 dated Jul. 7, 2025 (3 pages).
Supplementary Partial European Search Report in related European Application No. 20909879 dated Dec. 1, 2023 (12 pages).

* cited by examiner

200
G
211
210
X

280

284 282a 283a 273a 282b 273b 285 287 281a 286 281b 283b

TORQUE BALANCING DEVICE, SELF-BALANCING JOINT, AND SURGICAL ROBOT

CROSS-REFERENCE TO RELATED APPLICATIONS

This application is a national stage of International Application No. PCT/CN2020/138009, filed on Dec. 21, 2020, which claims priority to Chinese Patent Application Nos. 201911391803.3, filed on Dec. 30, 2019; 201911391794.8, filed on Dec. 30, 2019; 201911393258.1, filed on Dec. 30, 2019; 201911391792.9, filed on Dec. 30, 2019; 201911393239.9, filed on Dec. 30, 2019; 201911391727.6, filed on Dec. 30, 2019; 201922434125.6, filed on Dec. 30, 2019; 201922431993.9, filed on Dec. 30, 2019; and 201911393257.7, filed on Dec. 30, 2019. The entire contents of each of the above-identified applications are expressly incorporated herein by reference.

TECHNICAL FIELD

The present disclosure relates to the field of medical devices, and more particularly to a torque balancing device, a self-balancing joint, and a surgical robot.

BACKGROUND

It is well known that kinematic joints are the most commonly used mechanical parts in mechanical devices, especially in kinematic mechanisms. Depending on different applications, requirements for the performance of the kinematic joints may be different. There are many types of kinematic joints on the market at present, but most of them are used in occasions where requirements are not strict, such as low precision requirements, and most of them have an unidirectional power-assistance direction such that a load can only move in one direction.

However, in some important occasions where both high precision and bidirectional power-assistance are required, there is a need to provide a mechanical kinematic joint with an ingenious structure based on a simple and reliable principle.

Furthermore, it is expected in many cases that some kinematic joints are free to move or stop at any time, known as ready-to-stop joints. Such ready-to-stop joints need to meet performance requirements in two aspects: first, when being released, the kinematic joints immediately stop moving, achieving instant stop upon releasing; second, the kinematic joints have a power-assistance function such that a large force is not required when the joints are moved.

In some embodiments, the present disclosure provides an exemplary torque balancing device, the torque balancing device comprising: a first body comprising a first connection end and a first opposite end opposite to the first connection end; a second body comprising a second connection end and a second opposite end opposite to the second connection end, the second connection end of the second body being rotatably connected to the first connection end of the first body; an elastic part provided in the first body; and a transmission part connected to the second body and the elastic part, the transmission part being configured to be driven by rotation of the second body relative to the first body to compress the elastic part, and the elastic part being configured to provide torque balancing.

In some embodiments, the present disclosure further provides a self-balancing joint comprising a damping adjustment mechanism and a torque balancing device as described above.

In some embodiments, the present disclosure further provides a surgical robot, the surgical robot comprising at least one kinematic joint comprising a torque balancing device as described above or a self-balancing joint as described above.

BRIEF DESCRIPTION OF DRAWINGS

In order to explain the technical solutions in embodiments of the present disclosure more clearly, the accompanying drawings used in the description of the embodiments will be briefly introduced below. Obviously, the accompanying drawings in the following description are only some of the embodiments of the present disclosure, and for those of ordinary skill in the art, other accompanying drawings would also have been obtained from contents of the embodiments of the present disclosure and these drawings without involving any inventive effort.

FIG. 3(*b*) shows a schematic state diagram of a torsion spring with a second body in an intermediate position according to some embodiments of the present disclosure;

FIG. 6(*b*) shows a schematic state diagram of a torsion spring with a second body rotating clockwise according to some embodiments of the present disclosure;

FIG. 6(*c*) shows a schematic state diagram of a torsion spring with a second body in a left limit position according to some embodiments of the present disclosure;

FIG. 7(*b*) shows a schematic state diagram of a torsion spring with a second body rotating counterclockwise according to some embodiments of the present disclosure;

FIG. 7(*c*) shows a schematic state diagram of a torsion spring with a second body in a right limit position according to some embodiments of the present disclosure;

FIG. 29(*b*) shows a back view of the first body according to some embodiments of the present disclosure;

FIG. 41(*b*) is a schematic view of positions of components of the band brake device with the electromagnet being active;

FIG. 41(*c*) is a schematic view of positions of components of the band brake device when both the electromagnet and the band brake locking mechanism being active;

DETAILED DESCRIPTION

In order to make the technical problems solved by the present disclosure, technical solutions used by the present disclosure and technical effects achieved by the present disclosure more clear, the technical solutions of embodiments of the present disclosure will be described in detail below with reference to the accompanying drawings. Obviously, the described embodiments are merely some of, rather than all of, the embodiments of the present disclosure. All the other embodiments obtained by those skilled in the art based on the embodiments of the present disclosure without involving any creative efforts shall fall within the scope of protection of the present disclosure.

In the description, it should be explained that the orientation or positional relationships indicated by the terms "central", "upper", "lower", "left", "right", "vertical", "horizontal", "inner", "outer", etc. are based on the orientation or positional relationship shown in the accompanying drawings and are only for facilitating the description of the embodiments of the present disclosure and simplifying the description, rather than indicating or implying that a device or element referred to must have a particular orientation or be constructed and operated in a particular orientation, and therefore will not be interpreted as limiting the embodiments of the present disclosure. Moreover, the terms "first" and "second" are merely for illustrative purposes, and should not be construed as indicating or implying relative importance.

In the description of the present disclosure, it should be noted that unless explicitly specified and defined otherwise, the terms "mounting", "connecting", "connection", and "coupling" should be understood in a broad sense, for example, they may be a fixed connection, or a detachable connection, may be a mechanical connection or an electrical connection, may be a direct connection, an indirect connection via an intermediate medium, and may be internal communication between two elements. For those of ordinary skills in the art, the specific meaning of the terms mentioned above in the present disclosure may be construed according to specific circumstances.

In this disclosure, an end close to an operator is defined as a proximal end or part or a distal end or part, and an end close to a surgical patient is defined as a distal end or part or a proximal end or part.

In this disclosure, self balancing may be defined as providing an opposite acting force.

Figure 1:
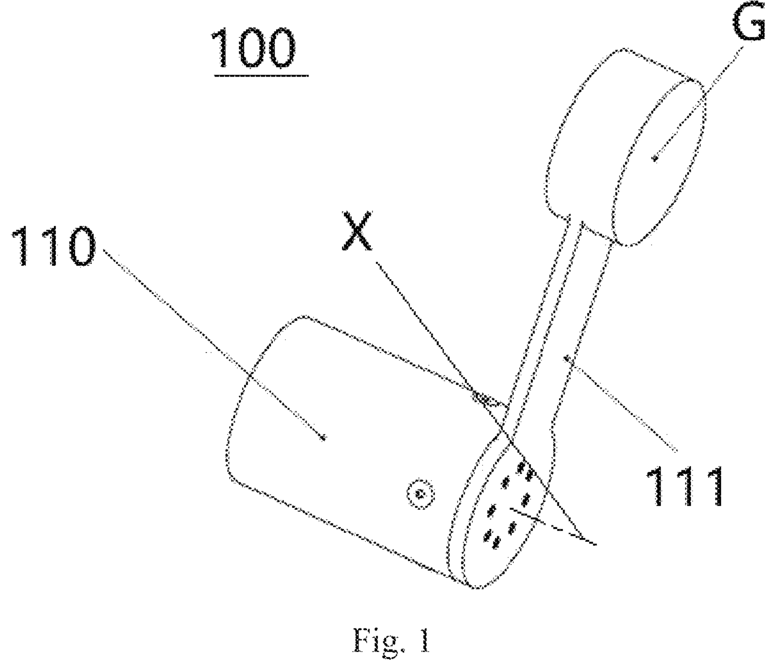
FIG. 1 shows a schematic structural diagram of a joint including a torque balancing device according to some embodiments of the present disclosure.
Figure 2:
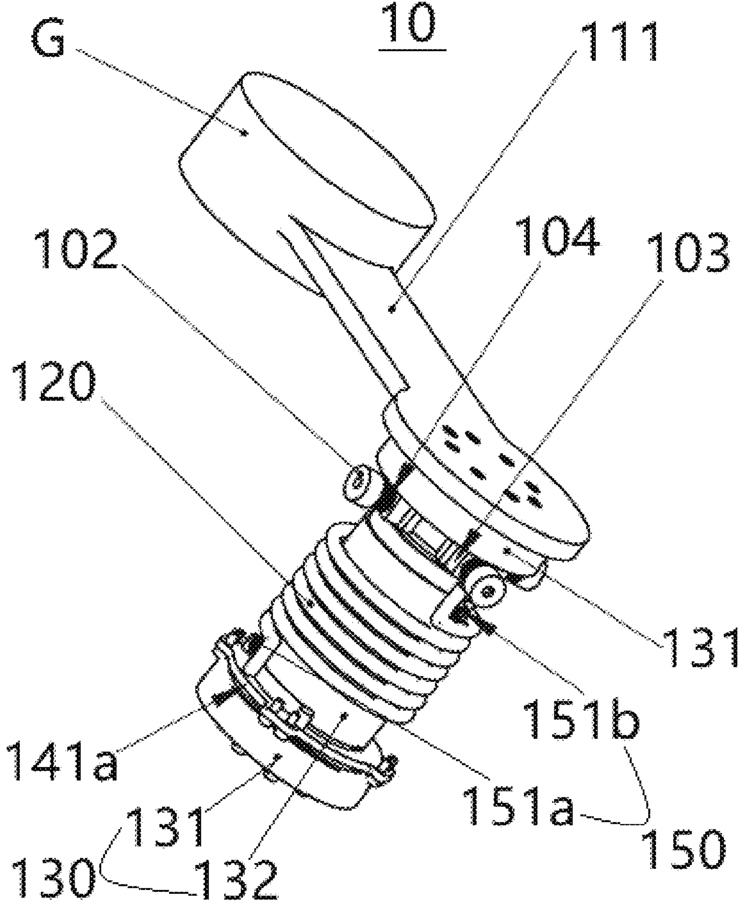
FIG. 2 shows a schematic structural diagram of a joint including a torque balancing device according to some embodiments of the present disclosure, with a first body removed.

FIGS. 1 and 2 respectively show a schematic diagram of an overall structure of a joint including a torque balancing device 100, and a schematic structural diagram with a first body 110 removed according to some embodiments of the present disclosure. As shown in FIGS. 1 and 2, the torque balancing device 100 provided in this embodiment may comprise an elastic part 120, a transmission part 130, as well as a first body 110 and a second body 111 that are rotatably connected to each other. The first body 110 may comprise a first connection end and a first opposite end opposite to the first connection end, the second body 111 may comprise a second connection end and a second opposite end opposite to the second connection end, the second connection end of the second body 111 is rotatably connected to the first connection end of the first body 110, and the second opposite end of the second body 111 may be provided with a load G (only exemplarily illustrated in FIGS. 1 and 2). The first connection end of the first body 110 may be fixedly connected to a movable or immovable carrier, or may be movably connected to a movable or immovable carrier, wherein the movable carrier may be a kinematic joint and the immovable carrier may be a base of a robot. The elastic part 120 is arranged in the first body 110, and the elastic part 120 may be a spring or other elastic member having an elastic restoring function. One end of the transmission part 130 is connected to the second body 111, and the other end of the transmission part 130 is connected to the elastic part 120. When the second body 111 is driven by an external force (or the load G) to rotate relative to the first body 110, the transmission part 130 is driven to move so as to compress the elastic part 120, and the elastic part 120 thus generates a reacting force comparable to the external force, such that torque balancing may be achieved.

The first body 110 and the second body 111 may be linkage structures. In some embodiments, the first body 110 and the second body 111 may be in cylindrical shapes, three-dimensional shapes, flat shapes, etc. In some embodiments, an axis of rotation X of the second body 111 may be perpendicular to lengthwise directions of the first body 110 and the second body 111. In some embodiments, as shown in FIG. 1, the axis of rotation X of the second body 111 may be parallel to the lengthwise direction of the first body 110 and perpendicular to the lengthwise direction of the second body 111. In some embodiments, the axis of rotation X of the second body 111 may be perpendicular to the lengthwise direction of the first body 110 and parallel to the lengthwise direction of the second body 111.

In some embodiments, as shown in FIG. 2, the transmission part 130 may comprise a bearing 131 and a rotating shaft 132, the bearing 131 including an inner race and an outer race that are rotatable relative to each other. At least one bearing 131 is mounted in the first body 110 (a pair of bearings 131 may be provided, and are respectively arranged at the first connection end and the first opposite end of the first body 110, as shown in FIG. 2), and the outer race of the bearing 131 is fixedly connected to the first body 110. One end of the rotating shaft 132 may be fixedly connected to the inner race of the bearing 131, and the other end of the rotating shaft 132 may be fixedly connected to the second connection end of the second body 111. As shown in FIG. 1, the axis of rotation X of the rotating shaft 132 is parallel to the lengthwise direction of the first body 110 and perpendicular to the lengthwise direction of the second body 111. Thus, the second body 111 may rotate relative to the first body 110.

Figure 3A:
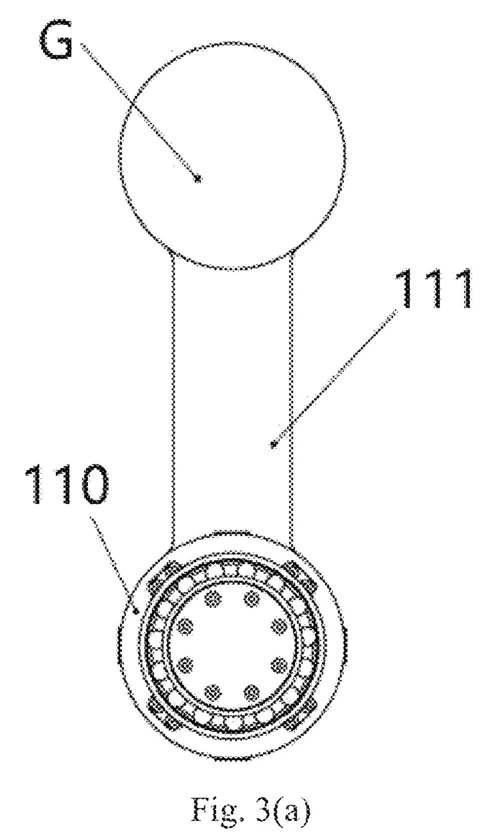
FIG. 3(*a*) shows a schematic state diagram of a second body in an intermediate position according to some embodiments of the present disclosure.
Figure 3B:
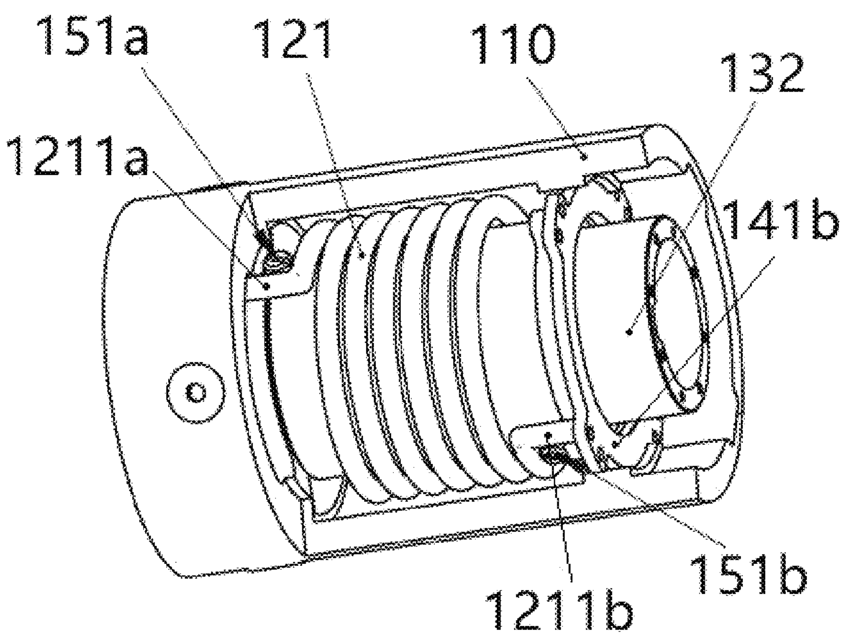

FIGS. 3(*a*) and 3(*b*) show a schematic state diagram of the second body 111 in an intermediate position and a schematic state diagram of a torsion spring 121 with the second body 111 in the intermediate position according to some embodiments of the present disclosure. As shown in FIG. 3(*b*), in some embodiments, the elastic part 120 may comprise the torsion spring 121, and two ends of the torsion spring 121 may each comprise outwardly extending leg 1211*a-b*.

Figure 4:
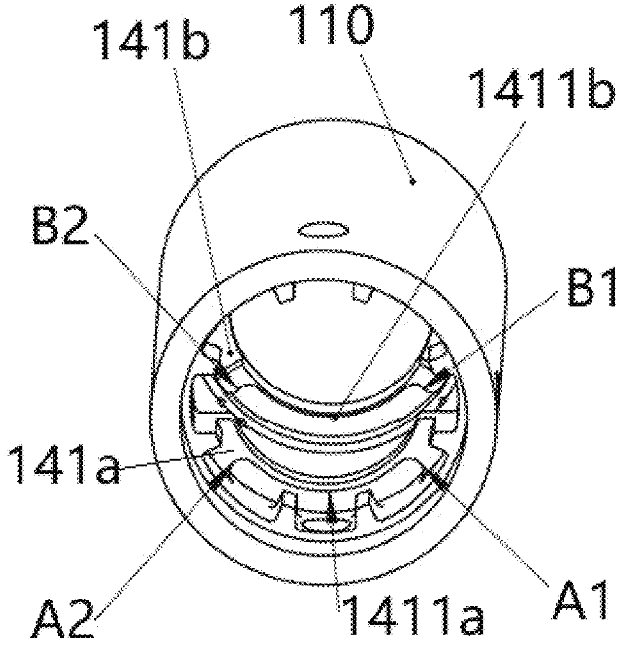
FIG. 4 shows a schematic structural diagram of a first body according to some embodiments of the present disclosure.
Figure 5:
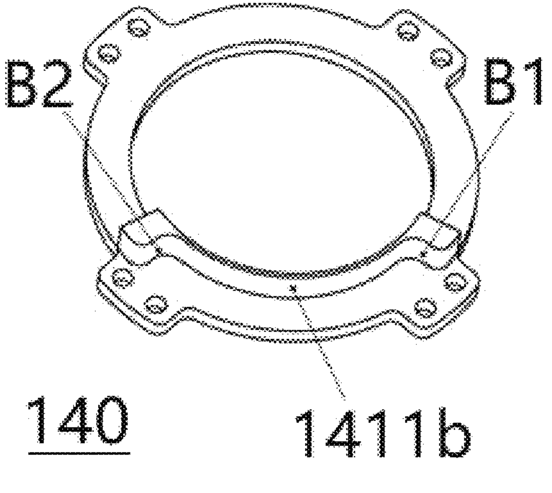
FIG. 5 shows a schematic structural diagram of a limiting baffle according to some embodiments of the present disclosure.

FIGS. 4 and 5 respectively show schematic structural diagrams of the first body 110 and a limiting baffle 141*b* according to some embodiments of the present disclosure. As shown in FIG. 5, in some embodiments, the torque balancing device 100 may further comprise a limiting part 140. As shown in FIG. 4, the limiting part 140 may comprise a first limiting baffle 141*a* and a second limiting baffle 141*b* arranged in the first body 110. Limiting slots 1411*a-b* for limiting the rotation of the torsion spring 121 within a given angle range are respectively formed in the first and second limiting baffles 141*a-b*. In some embodiments, as shown in FIG. 5, the first and second limiting baffles 141*a-b* may be annular plates, the limiting slots 1411*a-b* in the first and second limiting baffles 141*a-b* may be arc-shaped slots with radians matching an external contour of the rotating shaft 132, and a stop end A1-A2 and a stop end B1-B2 (refer to FIG. 4) for limiting the movements of the outwardly extending legs 1211*a-b* of the torsion spring 121 are respectively formed at two end portions of the limiting slots 1411*a-b*. The first and second limiting baffles 141*a-b* may be arranged in the first body 110, and are respectively sleeved with a distance therebetween at the two ends of the rotating shaft 132. The first and second limiting baffles 141*a-b* may be formed integrally with the first body 110 or fixedly connected to the first body 110.

In some embodiments, the torque balancing device 100 may further comprise a stopping part 150. The stopping part 150 may comprise at least one stopping screw. As shown in FIG. 2, the stopping part 150 may comprise a pair of stopping screws 151*a-b*, and the pair of stopping screws 151*a-b* may be fixedly or integrally formed at the two ends of the rotating shaft 132 respectively. The pair of the stopping screws 151*a-b* each extend in a radial direction of the rotating shaft 132.

As shown in FIG. 3(*a*), when the second body 111 is in an intermediate state, no torque is applied to the rotating shaft 132 by the load G, the torsion spring 121 does not need to provide a balancing force, and the torsion spring 121 at this time is in a state as shown in FIG. 3 (*b*) in which the outwardly extending leg 1211*a* of the torsion spring 121 may be in contact with the stopping screw 151*a* and the stop end A1 of the limiting slot 1411*a* (refer to FIG. 4) and the outwardly extending leg 1211*b* of the torsion spring 121 may be in contact with the stopping screw 151*b* and the stop end B2 of the limiting slot 1411*b*, and in this case, the torsion spring 121 is generally in a relaxed state except for a slight preload.

Figure 6A:
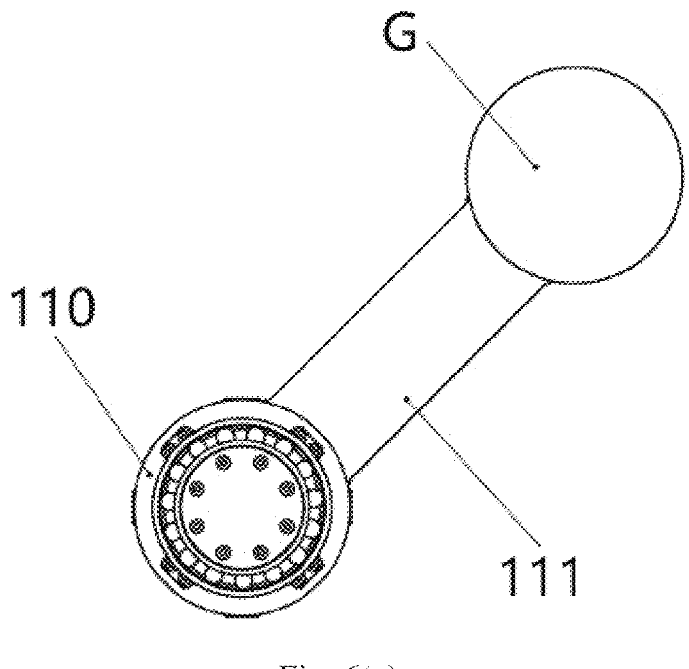
FIG. 6(*a*) shows a schematic state diagram of a second body rotating clockwise according to some embodiments of the present disclosure.
Figure 6B:
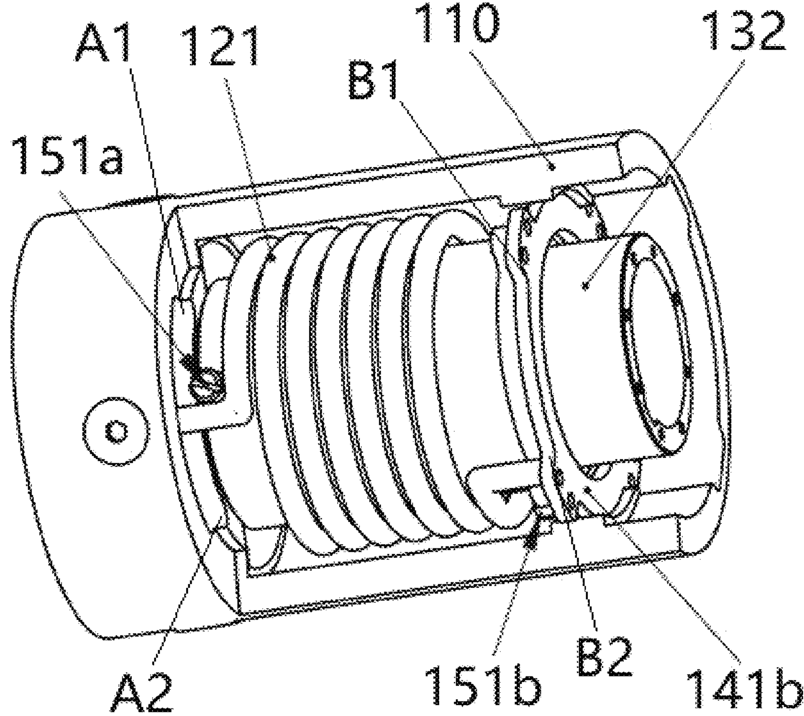
Figure 6C:
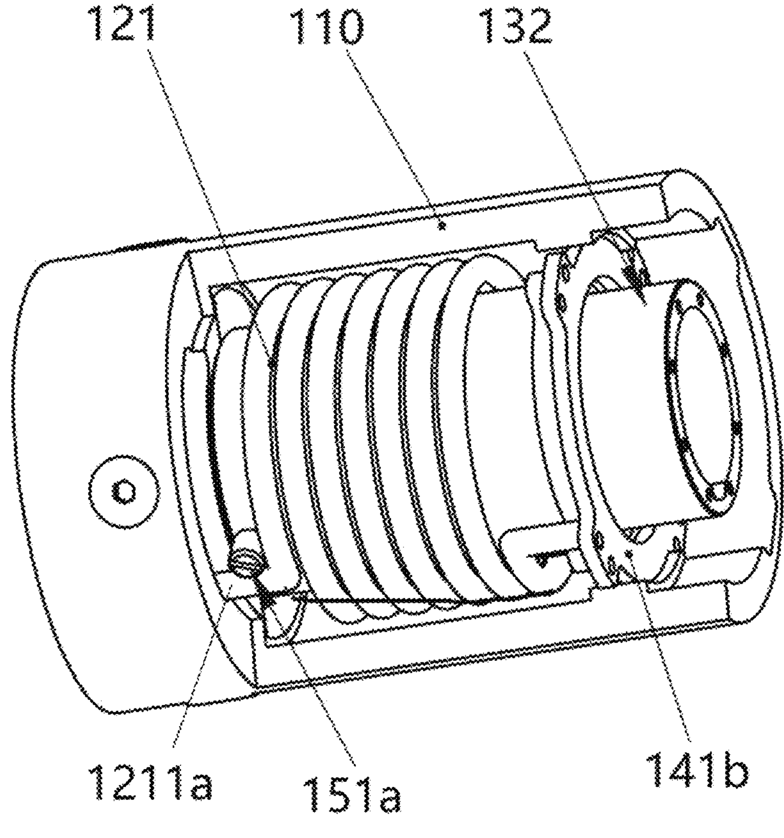

FIGS. 6(*a*), 6(*b*) and 6(*c*) respectively show a schematic state diagram of the second body 111 rotating clockwise, a schematic state diagram of the torsion spring 121 with the second body 111 rotating clockwise, and a schematic state diagram of the torsion spring 121 with the second body 111 in a clockwise limit position according to some embodiments of the present disclosure. As shown in FIG. 6(*a*), when the second body 111 rotates to the right (the term "right" herein refers to a clockwise direction as viewed in a direction perpendicular to a page plane of FIG. 6(*a*)), in this case the rotating shaft 132 rotates in the clockwise direction (the term "clockwise" herein refers to a clockwise direction as viewed in a direction perpendicular to the page planes of FIG. 5, FIG. 3(*a*), and FIG. 6(*a*)). As shown in FIG. 6(*b*), the stopping screws 151*a-b* that are fixedly connected to the rotating shaft 132 are driven to rotate, and the stopping screw 151*a* presses against and moves the outwardly extending leg 1211*a* of the torsion spring 121 from the stop end A1 to the stop end A2 of the limiting slot 1411*a* such that the torsion spring 121 is compressed, and at this time, the outwardly extending leg 1211*b* on the other side of the torsion spring 121 is limited to be immovable by the stop end B2 of the opposite limiting slot 1411*b*, whereby the torsion spring 121 may still generate a balancing force to balance the torque caused by the load G, achieving the purpose of force balancing and reducing an artificial acting force, and the state of the torsion spring 121 at this time is as shown in FIG. 6(*b*). When the second body 111 continues to rotate clockwise, the stopping screw 151*a* will continue to compress the torsion spring 121 until the outwardly extending leg 1211*a* of the torsion spring 121 reaches the stop end A2 of the limiting slot 1411*a*, at this time, the second body 111 enters a right limit state due to mechanical limiting, and a corresponding state of the torsion spring 121 is as shown in FIG. 6(*c*).

Figure 7A:
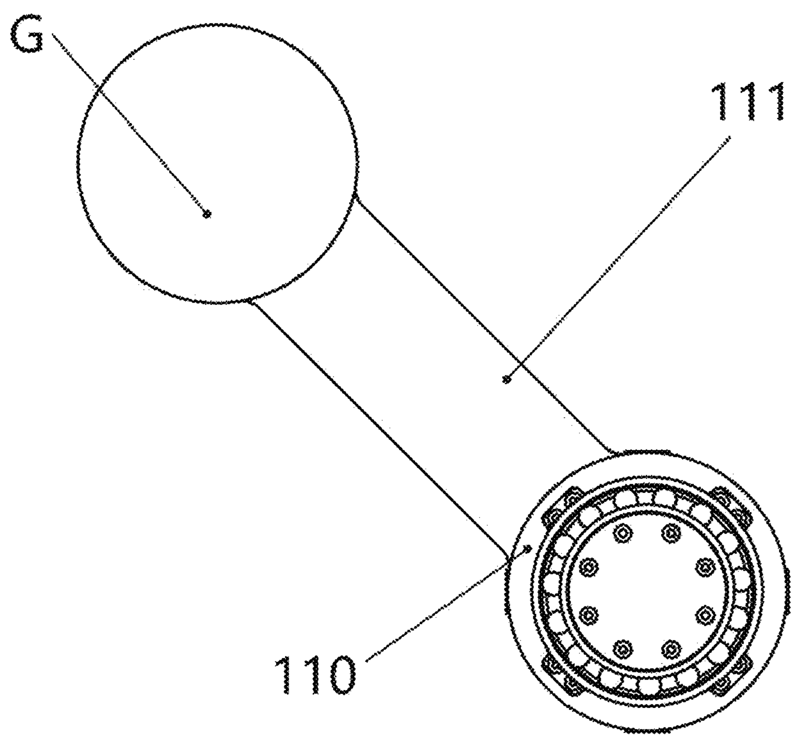
FIG. 7(*a*) shows a schematic state diagram of a second body rotating counterclockwise according to some embodiments of the present disclosure.
Figure 7B:
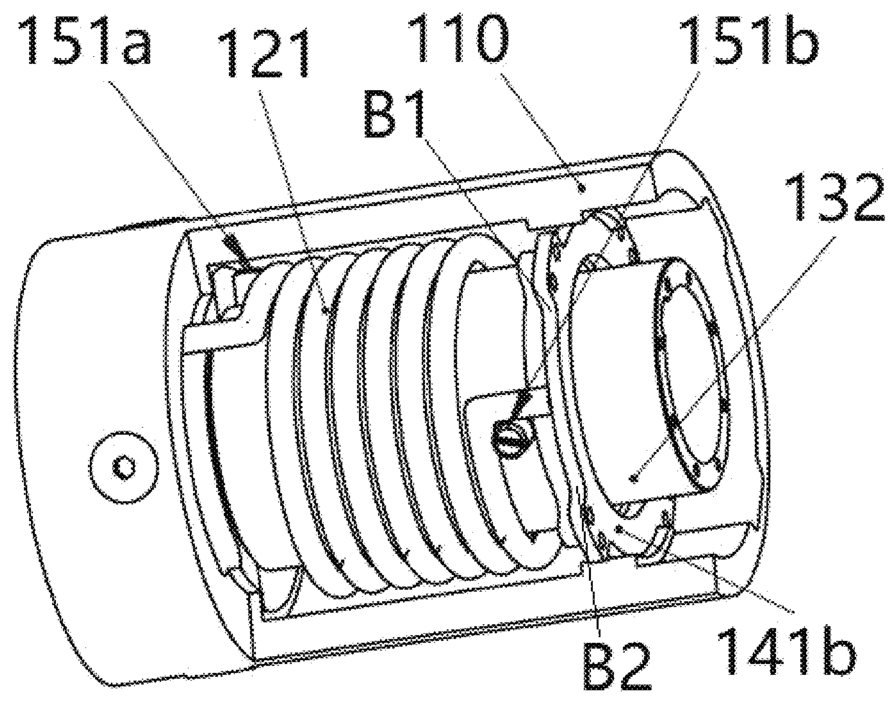
Figure 7C:
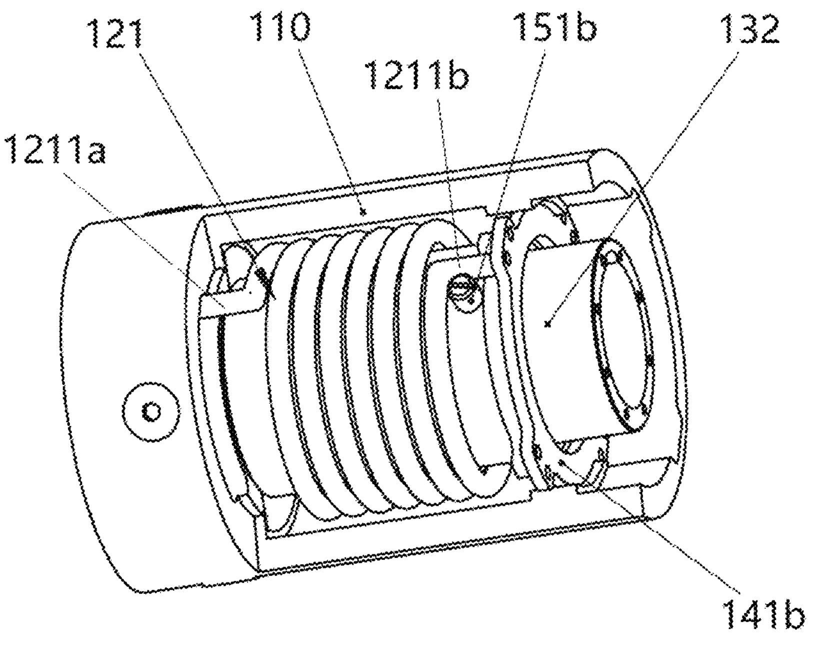

FIGS. 7(*a*), 7(*b*) and 7(*c*) respectively show a schematic state diagram of the second body 111 rotating counterclockwise, a schematic state diagram of the torsion spring 121 with the second body 111 rotating clockwise, and a schematic state diagram of the torsion spring 121 with the second body 111 in a counterclockwise limit position according to some embodiments of the present disclosure. As shown in FIG. 7(*a*), when the second body 111 rotates to the left (the term "left" herein refers to a counterclockwise direction as viewed in a direction perpendicular to the page plane of FIG. 7(*a*)), the rotating shaft 132 rotates in the counterclockwise direction (the term "counterclockwise" herein refers to the counterclockwise direction as viewed in a direction perpendicular to the page planes of FIG. 5, FIG. 3(*a*), FIG. 6(*a*), and FIG. 7(*a*)) to drive the stopping screw 151*b* fixedly connected to the rotating shaft 132 to rotate, the stopping screw 151*b* presses against and moves the outwardly extending leg 1211*b* on one side of the torsion spring 121 to move from the stop end B2 to the stop end B1 of the limiting slot 1411*b* such that the torsion spring 121 is rotatably compressed, and at this time, the outwardly extending leg 1211*a* on the other side of the torsion spring 121 is limited to be immovable by the stop end A1 of the limiting slot 1411*a*, whereby the torsion spring 121 may generate a balancing force to balance the torque caused by the load G, and the state of the torsion spring 121 at this time is as shown in FIG. 7(*b*). When the second body 111 continues to rotate counterclockwise, the stopping screw 151*b* will continue to compress the torsion spring 121 until the outwardly extending leg 1211*b* of the torsion spring 121 reaches the stop end B1 of the limiting slot 1411*b*, at this time, the second body 111 reaches a left limit position due to mechanical limiting, and a corresponding state of the torsion spring 121 is as shown in FIG. 7(*c*).

In some embodiments, one end of the torsion spring 121 may comprise an outwardly extending leg 1211. The limiting part 140 may comprise limiting baffles 141 fixedly arranged in the first body 110, and the limiting baffles 141 are sleeved with a distance therebetween outside the rotating shaft 132. The stopping part 150 comprises a stopping screw 151. In this case, the torsion spring 121 is sleeved outside the rotating shaft 132, the outwardly extending leg 1211 at one end of the torsion spring 121 abuts against the stopping screw 151, and a tip of the outwardly extending leg 1211 is movably constrained in the limiting slot 1411 of the limiting baffle 141. The other end of the torsion spring 121 may be fixedly arranged on the first body 110, whereby unidirectional torque balancing may be created, such that unidirectional power assistance may be achieved. The torque balancing device may provide an unidirectional balancing effect or a bidirectional balancing effect, has a compact structure, simple principles and easy to implement, and thus has very high practicality and reliability.

As shown in FIGS. 1 and 2, the self-balancing joint 10 provided by the present disclosure may comprise a torque balancing device 100 to achieve torque balancing when subjected to an external force or a load G. The torque balancing device mainly uses a mechanical structure so as to ensure that a kinematic joint and a ready-to-stop kinematic joint including the torque balancing device have very high stability and reliability.

In some embodiments, the self-balancing joint 10 may further comprise a damping adjustment mechanism 101.

Figure 8:
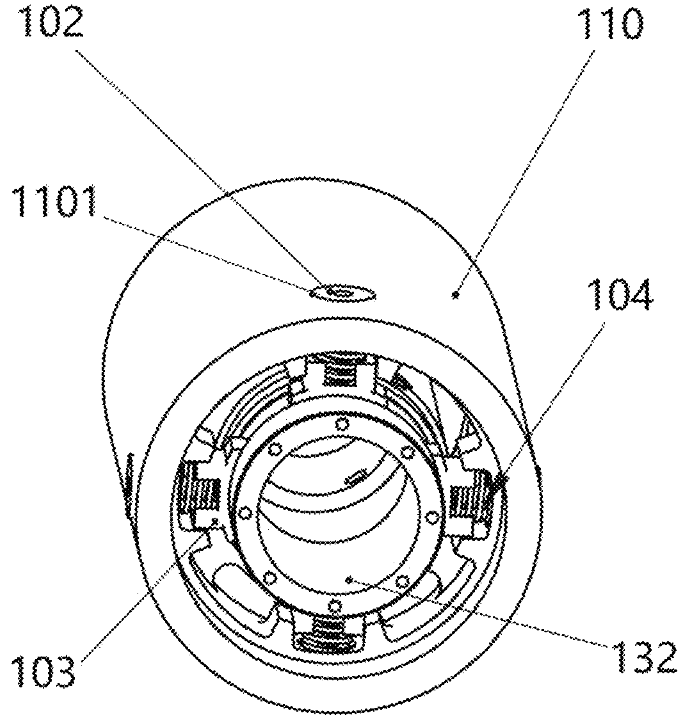
FIG. 8 shows a schematic structural diagram of a damping adjustment mechanism of a self-balancing joint according to some embodiments of the present disclosure.
Figures 9, 10:
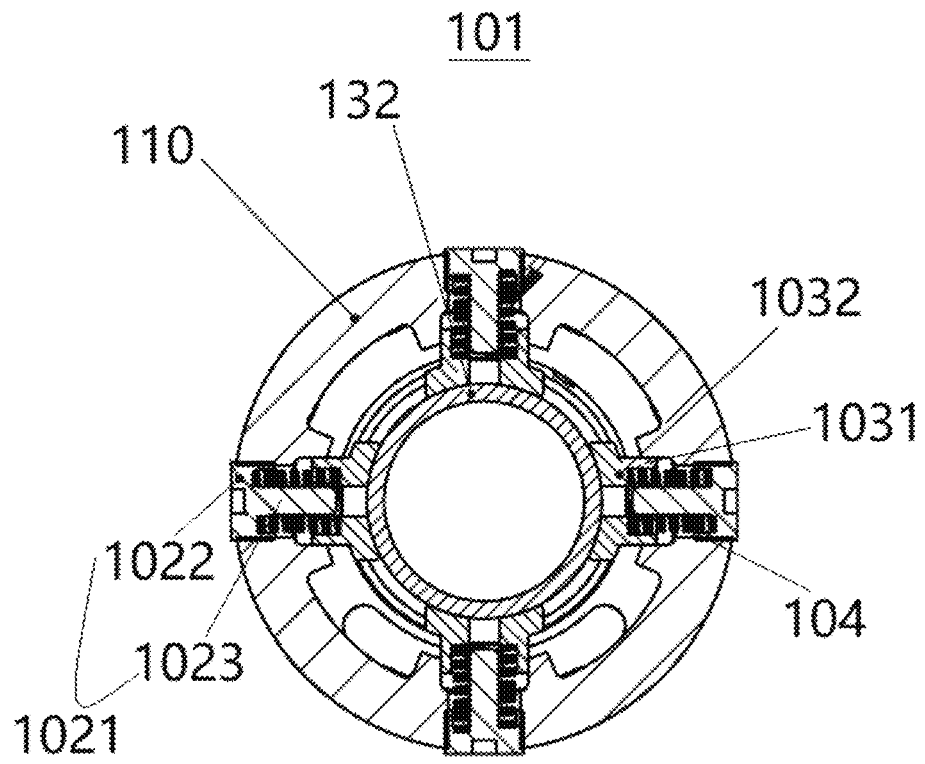
FIG. 9 shows a cross-sectional view of a damping increase mechanism according to some embodiments of the present disclosure.
FIG. 10 shows a schematic structural diagram of a torque balancing device according to some embodiments of the present disclosure.

FIGS. 8 and 9 respectively show a schematic structural diagram of the damping adjustment mechanism 101 of the self-balancing joint 10 and a cross-sectional view of the damping adjustment mechanism 101 according to some embodiments of the present disclosure. By packaging structures of a motion shafting, a spring power-assistance mechanism and a damping adjustment mechanism together, it is possible to achieve both a ready-to-stop kinematic joint moving in one direction and a ready-to-stop kinematic joint moving in two directions, and it is also possible to balance a large load in a small space.

As shown in FIGS. 8 and 9, the damping adjustment mechanism 101 may comprise a guiding member 102, a friction member 103, and a second elastic member 104. The guiding member 102 is arranged on the first body 110 and is movable in a radial direction of the first body 110. It will be appreciated that the guiding member 102 is slidable or movable by rotation by virtue of threads in the radial direction of the first body 110. The friction member 103 is radially movably and circumferentially non-rotatably arranged on the first body 110, an end portion of the friction member 103 is located outside the rotating shaft 132 and has a friction interface with the rotating shaft 132, and a play is left between the friction member 103 and the guiding member 102. One end of the second elastic member 104 abuts against the guiding member 102, and the other end of the second elastic member 104 abuts against the friction member 103. When the guiding member 102 moves in the radial direction of the first body 110 and close to the friction member 103, the second elastic member 104 is compressed to apply an acting force to the friction member 103, thereby increasing a friction force between the friction member 103 and the rotating shaft 132 and controlling a frictional damping to which the rotating shaft 132 is subjected in rotation. The damping adjustment mechanism may adjust the damping, such that the kinematic precision may be increased and the usability can be effectively ensured.

As shown in FIG. 9, in some embodiments, the guiding member 102 may be a guiding screw 1021. In some embodiments, the guiding screw 1021 comprises a guiding rod 1023 and a screw head 1022 integrally formed on one end of the guiding rod 1023, a mounting hole 1101 (refer to FIG. 8) for mounting the guiding screw 1021 may be provided in the first body 110, a part of the mounting hole 1101 away from the friction member 103 forms a threaded hole, a periphery of the guiding rod 1023 has an external thread fitting the threaded hole, and the guiding rod 1023 is disposed in the threaded hole in a screw-thread fit manner. The screw head 1022 may be configured to abut against the first body 110, namely, a limit position in which the guiding screw is screwed. In some embodiments, as shown in FIG. 9, a plurality of guiding screws 1021 may be provided, and the plurality of guiding screws 1021 may be uniformly arranged on the first body 110 in a circumferential direction.

As shown in FIG. 9, the friction member 103 may comprise a guiding post 1031 and a friction plate 1032 integrally formed on one end of the guiding post 1031, the friction plate 1032 is formed as having a friction surface in contact with the rotating shaft 132 which may be a curved surface matching the outer contour of the rotating shaft 132. In some embodiments, a stepped hole arranged in the radial direction of the rotating shaft 132 may be provided in the friction member 103, a thicker section of the stepped hole forms a spring positioning hole, and a thinner section of the stepped hole forms a screw guiding hole.

In some embodiments, another part of the mounting hole 1101 close to the friction member 103 forms a guiding hole, and the guiding post 1031 of the friction member 103 is slidably fitted in the guiding hole to limit the circumferential movement of the friction member 103 but not limit the radial movement of the friction member 103 along the rotating shaft 132.

In some embodiments, the second elastic member 104 may be a spring, the second elastic member 104 is sleeved on the guiding rod 1023 of the guiding screw 1021, the second elastic member 104 abuts against the screw head 1022 at one end and abuts against an end portion of the spring positioning hole of the stepped hole at the other end.

When the guiding rod 1023 of the guiding screw 1021 is screwed in or out in the radial direction of the first body 110 and close to or away from the friction member 103, the guiding rod 1023 is inserted into the screw guiding hole of the guiding post 1031 through the mounting hole 1101, and the guiding rod 1023 reciprocates along the screw guiding hole to change a distance between the guiding rod 1023 and the friction member 103, thereby changing the amount of compression of the second elastic member 104 to change a pressure of the friction member 103 on the rotating shaft 132, such that the damping provided by the friction member 103 to the rotating shaft 132 can be increased or decreased.

Figure 11:
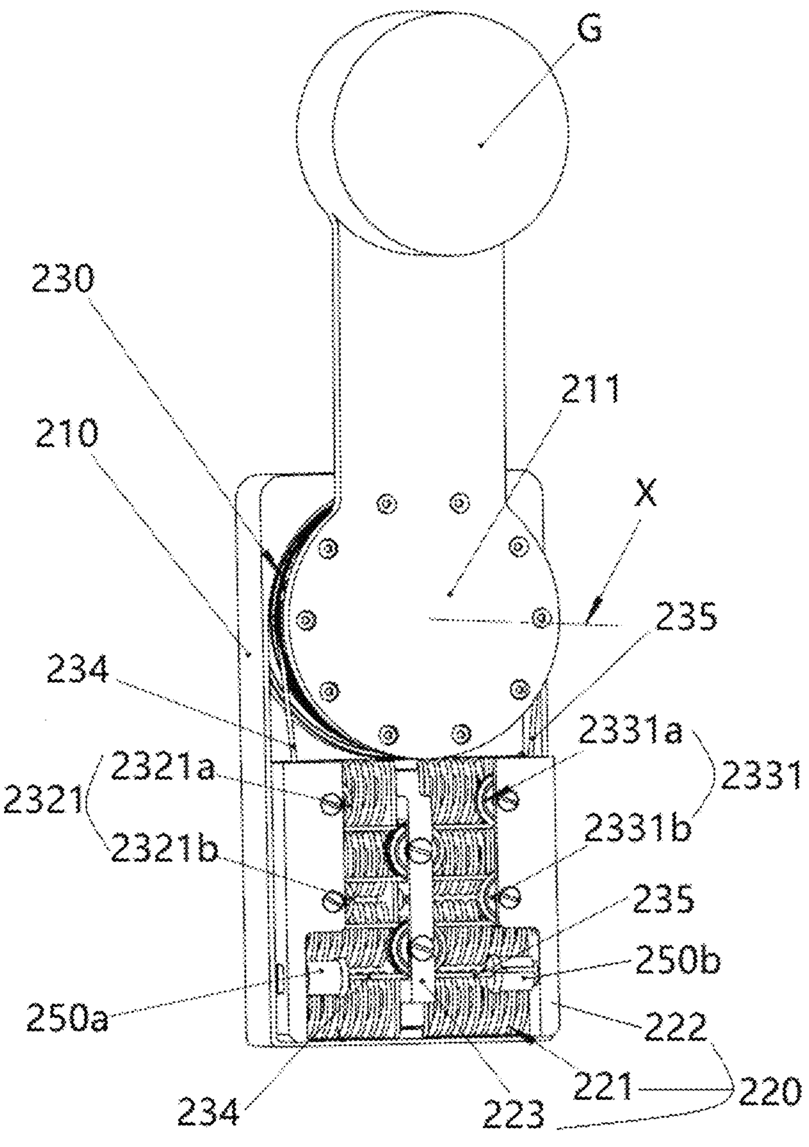
FIG. 11 shows a schematic diagram illustrating an internal structure of a torque balancing device according to some embodiments of the present disclosure.
Figure 12:
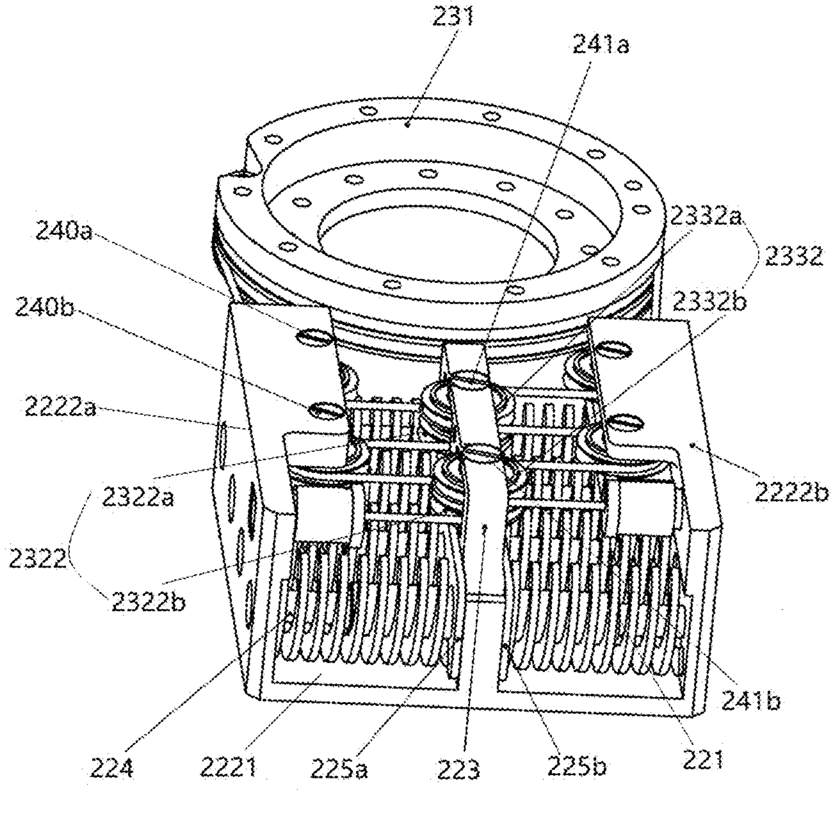
FIG. 12 shows a schematic diagram of a transmission part and an elastic part that cooperate with each other according to some embodiments of the present disclosure.

FIGS. 10 and 11 respectively show a schematic structural diagram of and a schematic diagram of an internal structure of a torque balancing device 200 according to some embodiments of the present disclosure, and FIG. 12 shows a schematic diagram of a transmission part 230 and an elastic part 220 that cooperate with each other according to some embodiments of the present disclosure.

In some embodiments, as shown in FIG. 11, the elastic part 220 may comprise a mounting seat 222, a sliding press block 223, and compression springs 221. The mounting seat 222 may be mounted on a first body 210, and the mounting seat 222 has an accommodating cavity therein. In some embodiments, the mounting seat 222 may be directly a part of the first body 210. As shown in FIG. 12, in some embodiments, the mounting seat 222 is in the form of a recess, the mounting seat 222 comprises a web plate 2221, and a first wing plate *2222a* and a second wing plate *2222b* located on two sides of the web plate 2221, and at least one guiding post 224 is provided between the first and second wing plates *2222a-b* of the mounting seat 222. The sliding press block 223 is located in an accommodating chamber of the mounting seat 222, and is slidably arranged on the guiding post 224. The sliding press block 223 may be in the form of a sheet or plate or the like. The compression springs 221 are disposed between the mounting seat 222 and the sliding press block 223. In some embodiments, the first and second wing plates *2222a-b* may each have an L-shaped cross section.

As shown in FIGS. 11 and 12, the sliding press block 223 is connected to a second body 211 via a transmission part 230. When the second body 211 rotates relative to the first body 210, the second body 211 drives the sliding press block 223 by means of the transmission part 230 to compress the compression spring 221, whereby the compression springs 221 generate a reaction force.

Figure 13:
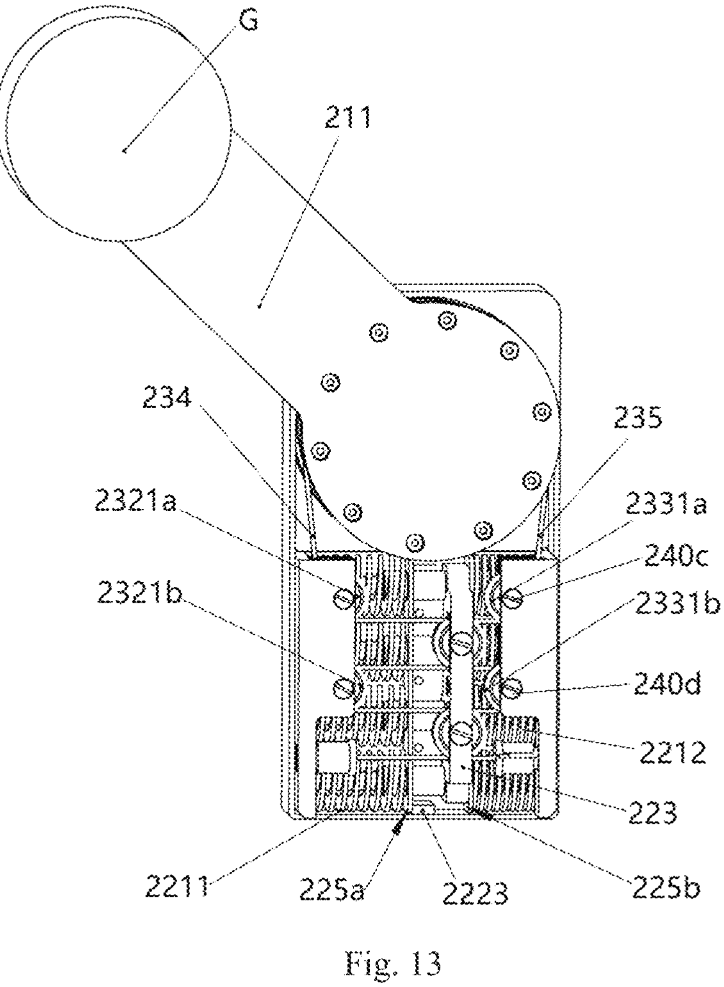
FIG. 13 shows a schematic state diagram of a second body rotating counterclockwise according to some embodiments of the present disclosure.
Figure 14:
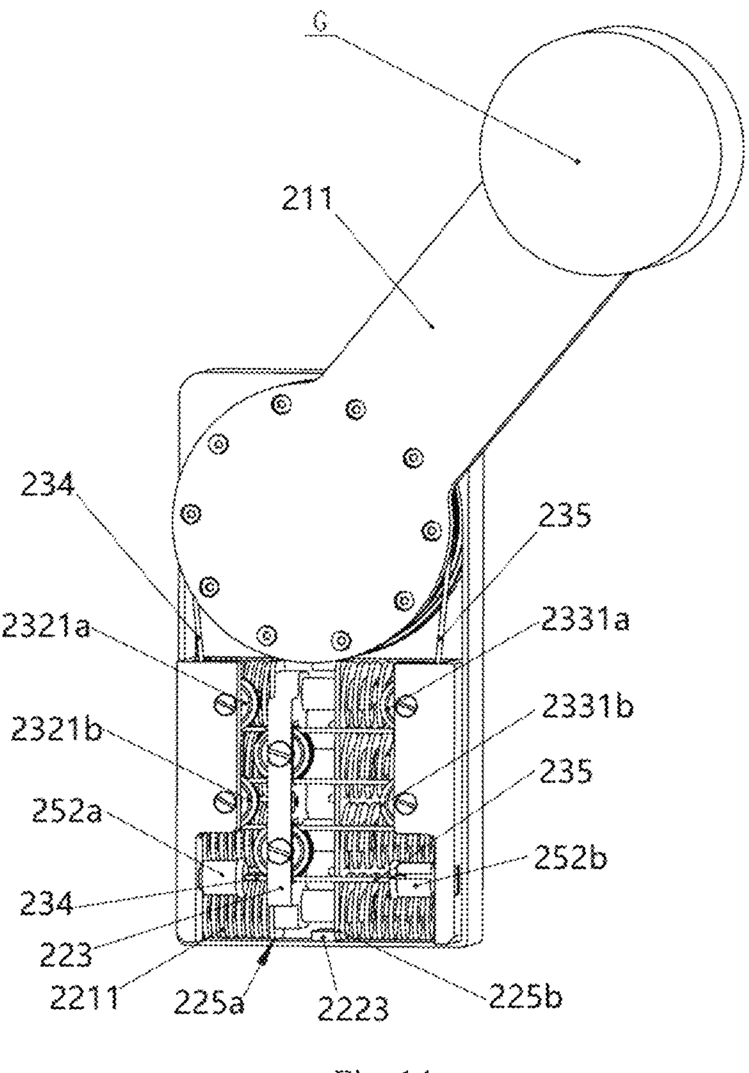
FIG. 14 shows a schematic state diagram of a second body rotating clockwise according to some embodiments of the present disclosure.

FIGS. 13 and 14 respectively show schematic state diagrams of the second body 211 rotating counterclockwise and clockwise according to some embodiments of the present disclosure. As shown in FIGS. 13 and 14, in some embodiments, the compression springs 221 may comprise a first group of compression springs 2211 and a second group of compression springs 2212 as shown in the figures. The elastic part may further comprise a pair of sliding press plates *225a-b*. The pair of sliding press plates *225a-b* are respectively slidably arranged on the guiding posts 224 located on two sides of the sliding press block 223, and the first group of compression springs 2211 and the second group of compression springs 2212 may respectively be sleeved on the guiding posts located between the sliding press plates 225*a-b* and the wing plates 2222*a-b* of the mounting seat 222. One end of each of the first group of compression springs 2211 and one end of each of the second group of compression springs 2212 respectively abut against the first and second wing plates 2222*a-b* of the mounting seat 222, and the other end of each of the first group of compression springs 2211 and the other end of each of the second group of compression springs 2212 respectively abut against the pair of sliding press plates 225*a-b*.

In some embodiments, at least one limiting block 2223 is provided on the web plate 2221 of the mounting seat 222 between the two sliding press plates 225*a-b* to restrict displacements of the sliding press plates 225*a-b*. In some embodiments, a plurality of the guiding posts 224 may be provided and are respectively spaced between the first and second wing plates 2222*a-b* of the mounting seat 222. The numbers of the first group of compression springs 2211 and the second group of compression springs 2212 may be adjusted as needed, and the first group of compression springs 2211 and the second group of compression springs 2212 may be respectively sleeved on corresponding guiding posts 224, such that loads G of different weights may be balanced to form a bidirectional power-assistance torque balancing device.

In some embodiments, the transmission part 230 may comprise a pulley transmission mechanism. As shown in FIGS. 11 and 12, the pulley transmission mechanism may comprise: an adapter block 231, a first pulley set, a second pulley set, a first traction rope 234 and a second traction rope 235.

The adapter block 231 is fixedly arranged at the second connection end of the second body 211, and the second body 211 may rotate relative to the first body 210 by means of the adapter block 231. It should be understood that the adapter block 231 may be a rotating shaft, an annular rotating member, a bearing, or the like, and that a circumferential surface of the adapter block 231 is provided with grooves arranged at intervals.

As shown in FIGS. 11 and 12, the first pulley set may comprise a first fixed pulley set 2321 and a first movable pulley set 2322, wherein the first fixed pulley set 2321 is rotatably arranged on the first wing plate 2222*a* of the mounting seat 222, and the first movable pulley set 2322 is rotatably arranged on the sliding press block 223. The second pulley set comprises a second fixed pulley set 2331 and a second movable pulley set 2332, wherein the second fixed pulley set 2331 is rotatably arranged on the second wing plate 2222*b* of the mounting seat 222, and the second movable pulley set 2332 is rotatably arranged on the sliding press block 223.

In some embodiments, the first traction rope 234 and the second traction rope 235 may be steel wire ropes or other high-strength ropes or belts. The first traction rope 234 and the second traction rope 235 are respectively located on two sides of the adapter block 231. The first traction rope 234 and the second traction rope 235 are fixedly connected to the adapter block 231 at one end and are wound around the grooves of the adapter block 231, the other end of the first traction rope 234 passes over the first fixed pulley set 2321 and the first movable pulley set 2322 and is then fixedly connected to the first wing plate 2222*a* of the mounting seat 222, and the other end of the second traction rope 235 passes over the second fixed pulley set 2331 and the second movable pulley set 2332 and is then fixedly connected to the second wing plate 2222*b* of the mounting seat 222.

As shown in FIGS. 12 and 13, in some embodiments, the first fixed pulley set 2321 may comprise a pair of first fixed pulleys 2321*a* and 2321*b* each rotatably connected to the first wing plate 2222*a* of the mounting seat 222 by means of a pair of fixed pulley pins 240*a-b*, and the second fixed pulley set 2331 may comprise a pair of second fixed pulleys 2331*a* and 2331*b* each rotatably connected to the second wing plate 2222*b* of the mounting seat 222 by means of a pair of fixed pulley pins 240*c-d*.

As shown in FIG. 13, in some embodiments, the first movable pulley set 2322 may comprise a pair of first movable pulleys 2322*a* and 2322*b* each rotatably connected to the sliding press block 223 by means of a pair of movable pulley pins 241*a-b*, and the second movable pulley set 2332 may comprise second movable pulleys 2332*a* and 2332*b* each rotatably connected to the sliding press block 223 by means of movable pulley pins 241*a-b*.

The other end of the first traction rope 234 passes over the first fixed pulley 2321*a*, the first movable pulley 2322*a*, the first fixed pulley 2321*b* and the first movable pulley 2331*b* in sequence and is then connected to the first wing plate 2222*a* of the mounting seat 222, and the other end of the second traction rope 235 passes over the second fixed pulley 2331*a*, the second movable pulley 2332*a*, the second fixed pulley 2331*b* and the second movable pulley 2332*b* in sequence and is then connected to the second wing plate 2222*b* of the mounting seat 222.

In an initial state (as shown in FIG. 11), the center of gravity of the load G is located directly above the axis of rotation X of the adapter block 231, and at this time, the load G (e.g., the gravity) does not generate a torque to the adapter block 231. At this time, the sliding press block 223 is in an intermediate state in which the left sliding press plate 225*a* rightwards abuts against the limiting block 2223 on the mounting seat 222 under the action of the first group of compression springs 2211, and the right sliding press plate 225*b* leftwards abuts against the limiting block 2223 on the mounting seat 222 under the action of the second group of compression springs 2212, and at this time, the first group of compression springs 2211 and the second group of compression springs 2212 are substantially in an original length state except for a slight preload, and the first group of compression springs 2211 and the second group of compression springs 2212 have no acting force on the adapter block 231 or the second body 211, and the entire device is in a balanced state in this case.

When the second body 211 rotates to the left (as shown in FIG. 13) (the term "left" herein refers to a counterclockwise direction as viewed in a direction perpendicular to the page plane of FIG. 13), the adapter block 231 rotates in the counterclockwise direction (the term "counterclockwise" herein refers to a counterclockwise direction as viewed in a direction perpendicular to the page planes of FIGS. 11 and 13), the load G generates a counterclockwise torque to the adapter block 231, the second traction rope 235 moves upwards under the drive of the adapter block 231 at this time, the second traction rope 235 has an increased length wound around the adapter block 231 to drive the sliding press block 223 to move to the right by means of the second movable pulleys 2332*a* and 2332*b*, and the sliding press block 223 makes the second group of compression springs 2212 on its right side in a compressed state by means of the right sliding press plate 225*b*, such that a balancing force is generated to balance the torque generated by the load G to the adapter block 231. Meanwhile, the first group of compression springs 2211 on the left side is in an original state under the restriction of the left sliding press plate 225*a* (cannot move to the right due to the restriction by the limiting block 2223). However, since the sliding press block 223 drives the first movable pulley 2322*a* and the first movable pulley 2322*b* to move to the right, the first traction rope 234 has a reduced length wound around the adapter block 231, and this length is exactly the same as the length required for allowing the first movable pulleys 2322*a* and 2322*b* to move to the right. Therefore, the first traction rope 234 always maintains in a tensioned state under the drawing of the first movable pulleys 2322*a* and 2322*b*. Thus, when the load G moves to the left, a sudden acceleration would not occur under a balancing force, and an external acting force required when the torque balancing device 200 returns to its original state is greatly reduced, such that a good power assistance function can be achieved.

When the second body 211 rotates to the right (as shown in FIG. 14) (the term "right" herein refers to a clockwise direction as viewed in a direction perpendicular to the page plane of FIG. 14), the adapter block 231 rotates in the clockwise direction (the term "clockwise" herein refers to a clockwise direction as viewed in a direction perpendicular to the page planes of FIGS. 11 and 14). The load G generates a clockwise torque to the adapter block 231, the first traction rope 234 moves upwards under the drive of the adapter block 231 at this time, the first traction rope 234 has an increased length wound around the adapter block 231 and then drive the sliding press block 223 to move to the left by means of the first movable pulleys 2322*a* and 2322*b*, and the sliding press block 223 makes the first group of compression springs 2211 on its left side in a compressed state by means of the left-side sliding press plate 225*a*, such that a balancing force is generated to balance the torque provided by the load G to the rotating shaft. Meanwhile, the second group of compression springs 2212 on the right side is in an original state under the restriction of the right sliding press plate 225*b* (cannot move to the left due to the restriction by the limiting block 2223). However, since the sliding press block 223 drives the second movable pulleys 2332*a* and 2332*b* to move to the right, the second traction rope 235 has a reduced length wound around the adapter block 231, and this length is exactly the same as the length required for allowing the second movable pulleys 2332*a* and 2332*b* to move to the right. Therefore, the second traction rope 235 always maintains in a tensioned state under the drawing of the second movable pulleys 2332*a* and 2332*b*.

In some embodiments, the elastic part 220 may comprise a first group of compression springs 2211 and a sliding press block 223. The first group of compression springs 2211 are sleeved on the guiding posts 224 located between the first wing plate 2222*a* located on one side of the mounting seat 222 and the sliding press block 223, one end of each of the first group of compression springs 2211 abuts against the first wing plate 2222*a* of the mounting seat 222 and the other end thereof abuts against the sliding press block 223. In some embodiments, the pulley transmission mechanism comprises: an adapter block 231, a first pulley set and a first traction rope 234. The first traction rope 234 is located on one side of the adapter block 231, the first traction rope 234 is fixedly connected to the adapter block 231 at one end of and is wound around a groove of the adapter block 231, and the other end of the first traction rope 234 passes over the first fixed pulley set 2321 and the first movable pulley set 2322 and is then fixedly connected to the first wing plate 2222*a* of the mounting seat 222. It is thus possible to form an unidirectional power-assistance torque balancing device 200.

Figure 15:
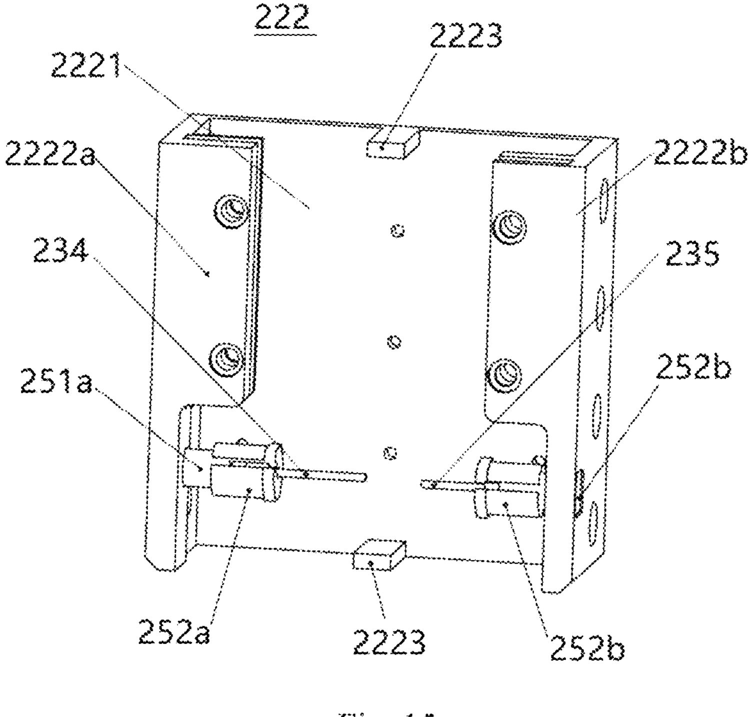
FIG. 15 shows a schematic structural diagram of a mounting seat according to some embodiments of the present disclosure.

FIG. 15 shows a schematic structural diagram of a mounting seat 222 according to some embodiments of the present disclosure. As shown in FIGS. 11 and 15, in some embodiments, the torque balancing device 200 may further comprise first and second traction rope adjustment parts 250*a-b*. The first traction rope adjustment part 250*a* may comprise a stud 251*a* and an adjustment block 252*a*, and the second traction rope adjustment part 250*b* may comprise a stud 251*b* and an adjustment block 252*b*, wherein the studs 251*a* and 251*b* are respectively arranged on the first and second wing plates 2222*a-b* of the mounting block 222, and external threads are each formed on the studs 251*a* and 251*b*. The adjustment blocks 252*a* and 252*b* are in the form of a hollow cylinder, and internal threads matching with the external threads of the studs 251*a* and 251*b* are respectively formed on the inside of the adjustment blocks 252*a* and 252*b*. The adjustment blocks 252*a* and 252*b* are respectively in threaded connection with the studs 251*a* and 251*b*, and the first traction rope 234 and the second traction rope 235 are respectively fixedly connected to the adjustment blocks 252*a* and 252*b*. Thus, by means of rotating the adjustment blocks 252*a* and 252*b*, movement of the adjustment blocks along the studs 251*a* and 251*b* may be achieved, which in turn may adjust the positions of the first traction rope 234 and the second traction rope 235, such that the sliding press block 223 is in the middle of the guiding post 224 and both the first traction rope 234 and the second traction rope 235 are in a tensioned state during balancing. It will be appreciated that the positions of the adjustment blocks 252*a* and 252*b* may maintain unchanged during use.

In some embodiments, as shown in FIG. 15, the adjustment blocks 252*a* and 252*b* may each be formed with a notch in an axial direction, and the other end of each of the first traction rope 234 and the second traction rope 235 forms a protruding abutment portion that may be in the form of a block or a post or have other shapes and that may be used for preventing the first traction rope 234 and the second traction rope 235 from slipping off the notches. The first traction rope 234 and the second traction rope 235 are respectively threaded into the adjustment blocks 252*a* and 252*b* through the notches, such that the abutment portions of the first traction rope 234 and the second traction rope 235 are respectively constrained within the adjustment blocks 252*a* and 252*b*.

Figure 16:
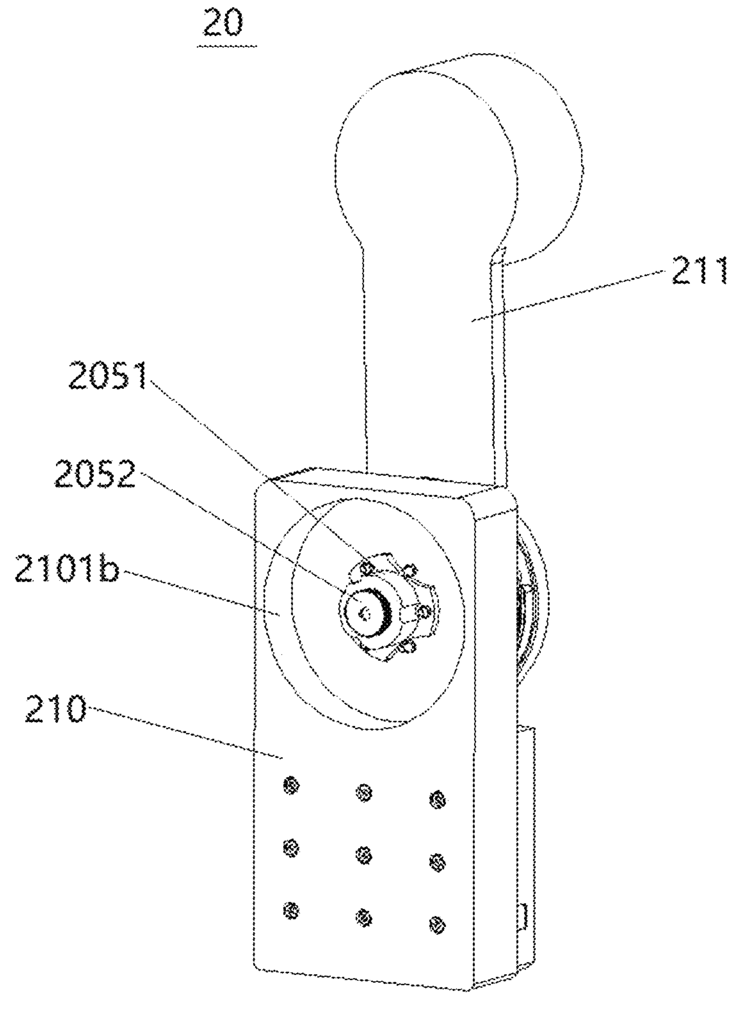
FIG. 16 shows a schematic structural diagram of a back surface of a self-balancing joint according to some embodiments of the present disclosure.
Figure 17:
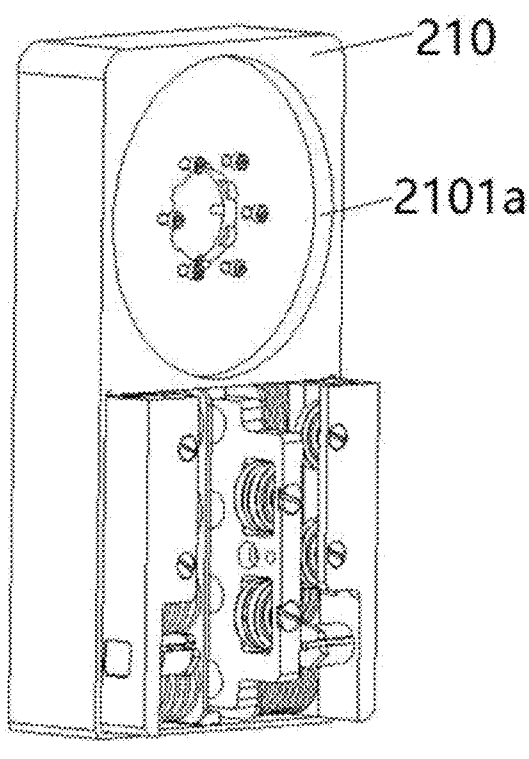
FIG. 17 shows a partial schematic structural diagram of a self-balancing joint according to some embodiments of the present disclosure.
Figure 18:
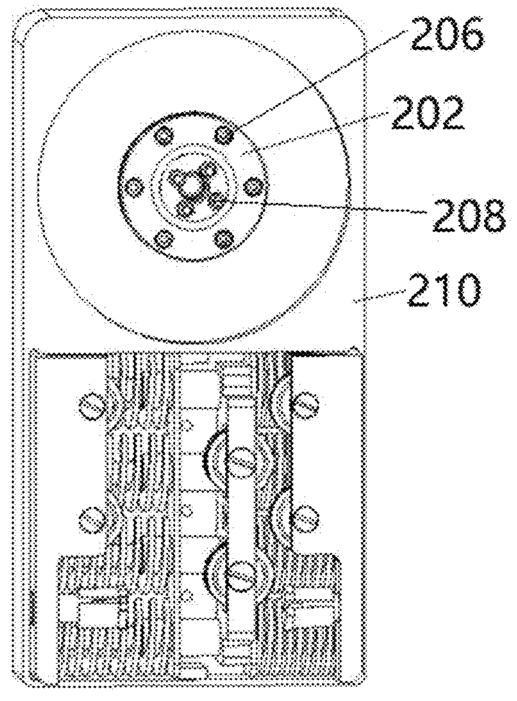
FIG. 18 shows another partial schematic structural diagram of a self-balancing joint according to some embodiments of the present disclosure.

FIGS. 16, 17, and 18 respectively show structural diagrams of a back surface, a partial schematic structural diagram and another partial schematic structural diagram of a self-balancing joint 20 according to some embodiments of the present disclosure. In some embodiments, as shown in FIGS. 16, 17, and 18, the self-balancing joint 20 provided by the present disclosure may comprise a torque balancing device 200 to achieve torque balancing when subjected to an external force or a load G.

Figure 19:
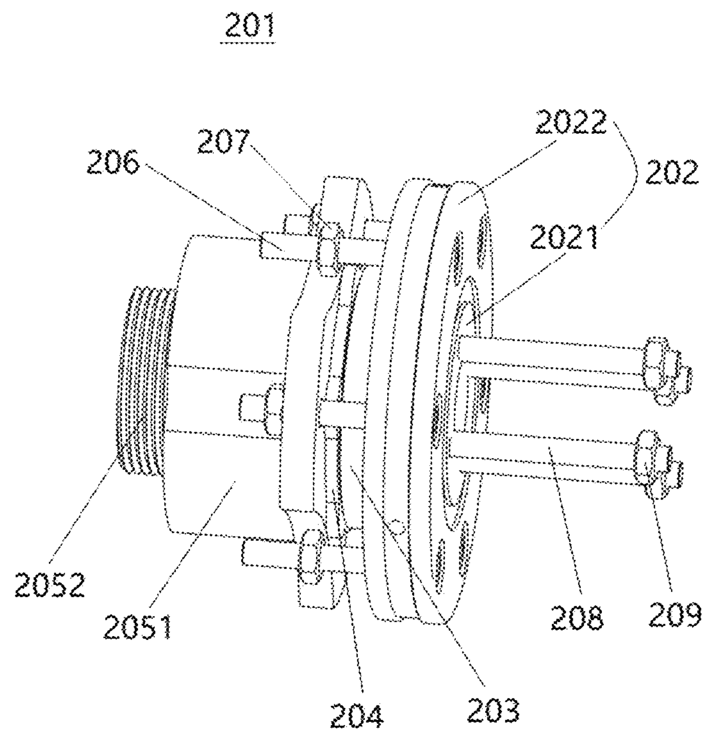
FIG. 19 shows a schematic structural diagram of a damping adjustment mechanism according to some embodiments of the present disclosure.
Figure 20:
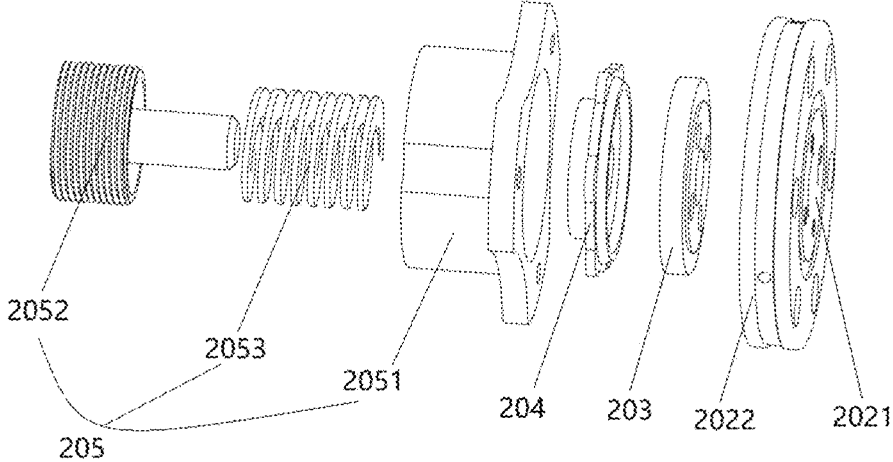
FIG. 20 shows an exploded view of a damping adjustment mechanism according to some embodiments of the present disclosure.

In some embodiments, the self-balancing joint 20 may further comprise a damping adjustment mechanism 201. FIGS. 19 and 20 respectively show a schematic structural diagram of a damping adjustment mechanism 201 and an exploded view of the damping adjustment mechanism 201 according to some embodiments of the present disclosure, and FIG. 21 shows a cross-sectional view of a self-balancing joint 20 according to some embodiments of the present disclosure.

Figure 21:
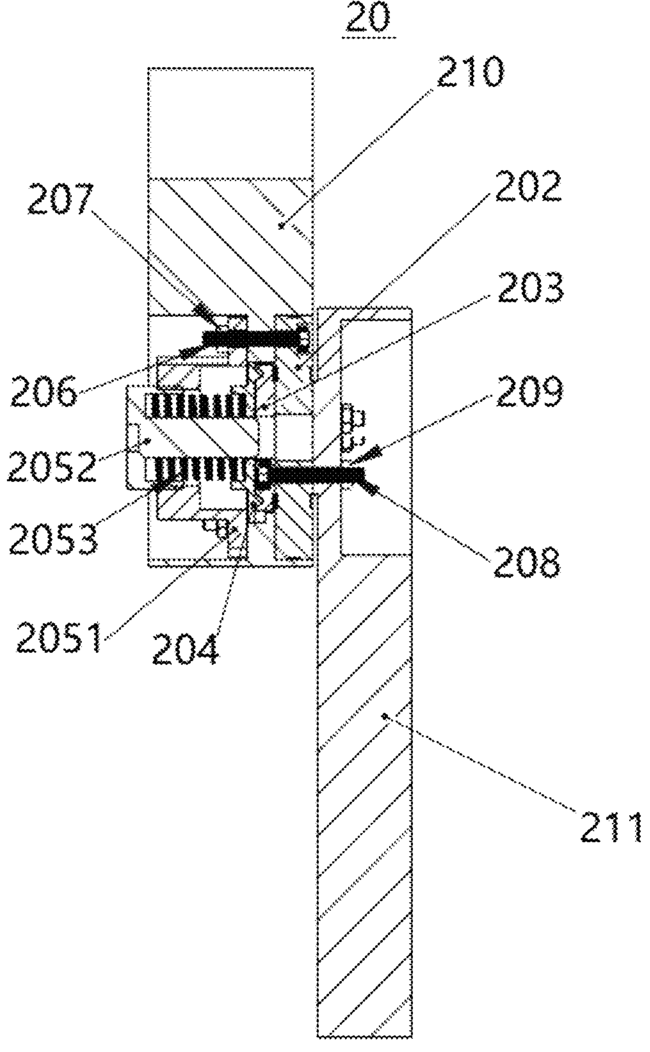
FIG. 21 shows a cross-sectional view of a self-balancing joint according to some embodiments of the present disclosure.

As shown in FIGS. 19, 20, and 21, the damping adjustment mechanism 201 may comprise: a rotating part 202, a first friction part 203, a second friction part 204 and an adjustment part 205. The rotating part 202 comprises an inner race 2021 and an outer race 2022 that are relatively rotatable, and the outer race 2022 of the rotating part 202 is fixedly connected to the first body 210. The first friction part 203 is fixedly connected to the inner race 2021 of the rotating part 202 and the second body 211. The second friction part 204 is axially movably and circumferentially non-rotatably arranged on the first body 210, and a friction interface is formed between the second friction part 204 and the first friction part 203. The adjustment part 205 is connected to the second friction part 204 for driving the second friction part 204 to move closer to or away from the first friction part 203 in an axial direction of the damping adjustment mechanism 201, such that frictional damping at the friction interface between the second friction part 204 and the first friction part 203 increases or decreases, which may control the frictional damping to which the rotating part 202 is subjected during rotation.

As shown in FIG. 19, in some embodiments, the rotating part 202 may be a crossed roller bearing with the outer race 2022 being able to be fixedly connected to the first body 210 by means of bolts 206 and nuts 207. The inner race 2021 of the crossed roller bearing is fixedly connected to the first friction part 203 and the second body 211 by means of bolts 208 and nuts 209, and the first friction part 203 is located on a side of the crossed roller bearing close to the first body 210, and the second body 211 is located on the other side of the crossed roller bearing away from the first body 210. In some embodiments, the first friction part 203 may be an inner race friction ring, and the second friction part 204 may be an outer race friction ring. In some embodiments, the first friction part 203 and the second friction part 204 may also be friction blocks or friction plates.

In some embodiments, the adjustment part 205 may comprise: a retainer 2051, a guiding member 2052, and a first elastic member 2053. The retainer 2051 may be fixedly connected to the first body 210 and the outer race 2022 of the crossed roller bearing by means of the bolts 206 and the nuts 207. The guiding member 2052 is arranged on the retainer 2051 and is movable in an axial direction of the retainer 2051. It will be appreciated that the guiding member 2052 is slidable or movable by rotation by virtue of threads in the axial direction of the first body 210. The first elastic member 2053 may be sleeved on the guiding member 2052, one end of the first elastic member 2053 abuts against the guiding member 2052, and the other end of the first elastic member 2053 abuts against the second friction part 204. In some embodiments, the first elastic member 2053 may be a spring.

In some embodiments, as shown in FIG. 20, the guiding member 2052 may be a guiding screw which may comprise a guiding rod and a screw head integrally formed on one end of the guiding rod, wherein the periphery of the screw head has an external thread, and an inner race of the retainer 2051 has an internal thread matching with the external thread of the screw head, such that the screw head is threadedly connected in the retainer 2051. A spring positioning sleeve is formed between the guiding rod and the screw head, one end of the first elastic member 2053 is located in the spring positioning sleeve, and the other end of the first elastic member 2053 abuts against the second friction part 204.

Thus, when the guiding member 2052 is rotated to be screwed in in the axial direction of the damping adjustment mechanism 201, the first elastic member 2053 is compressed to apply an acting force to the second friction part 204, such that larger frictional damping is generated between the second friction part 204 and the first friction part 203 to limit relative rotation between the inner race 2021 and the outer race 2022 of the rotating part 202 and thus limit relative rotation between the second body 211 and the first body 210 that are respectively connected to the inner race 2021 and the outer race 2022 of the rotating part 202. On the contrary, when the guiding member 2052 is rotated to be screwed out in the axial direction of the damping adjustment mechanism 201, the amount of compression of the first elastic member 2053 is reduced to reduce the frictional damping between the second friction part 204 and the first friction part 203, such that the relative rotation between the inner race 2021 and the outer race 2022 of the rotating part 202 is facilitated and the relative rotation between the second body 211 and the first body 210 that are respectively connected to the inner race 2021 and the outer race 2022 of the rotating part 202 is thus facilitated.

In some embodiments, as shown in FIGS. 17 and 18, recesses 2101*a* and 2101*b* are respectively formed in two sides of the first connection end of the first body 210. The rotating part 202 is located in the recess 2101*a*, and the retainer 2051, the first elastic member 2053, and the guiding member 2052 are located in the recess 2101*b*. A guiding channel is formed in the first body 210 between the recess 2101*a* and the recess 2101*b*, and the first friction part 203 and the second friction part 204 are located in the guiding channel.

Figure 22:
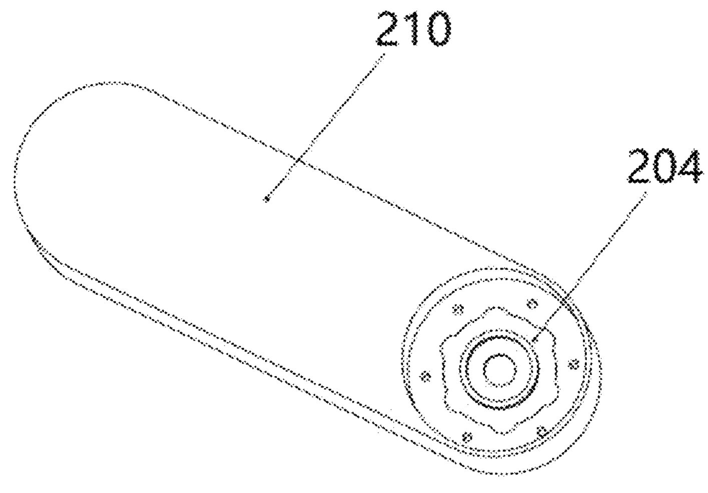
FIG. 22 shows a schematic structural diagram of the first body and the second friction part that cooperate according to some embodiments of the present disclosure.

FIG. 22 shows a schematic structural diagram of the first body 210 and the second friction part 204 that cooperate according to some embodiments of the present disclosure. As shown in FIG. 22, in some embodiments, a plurality of bulging teeth are formed on the second friction part 204, a guiding groove that fits the outer contour of the second friction part 204 is formed in the guiding channel of the first body 210, and the second friction part 204 fits in the guiding groove such that the guiding groove may limit the circumferential movement of the second friction part 204 but does not limit the movement of the second friction part 204 in the axial direction of the damping adjustment mechanism 201.

Figure 23:
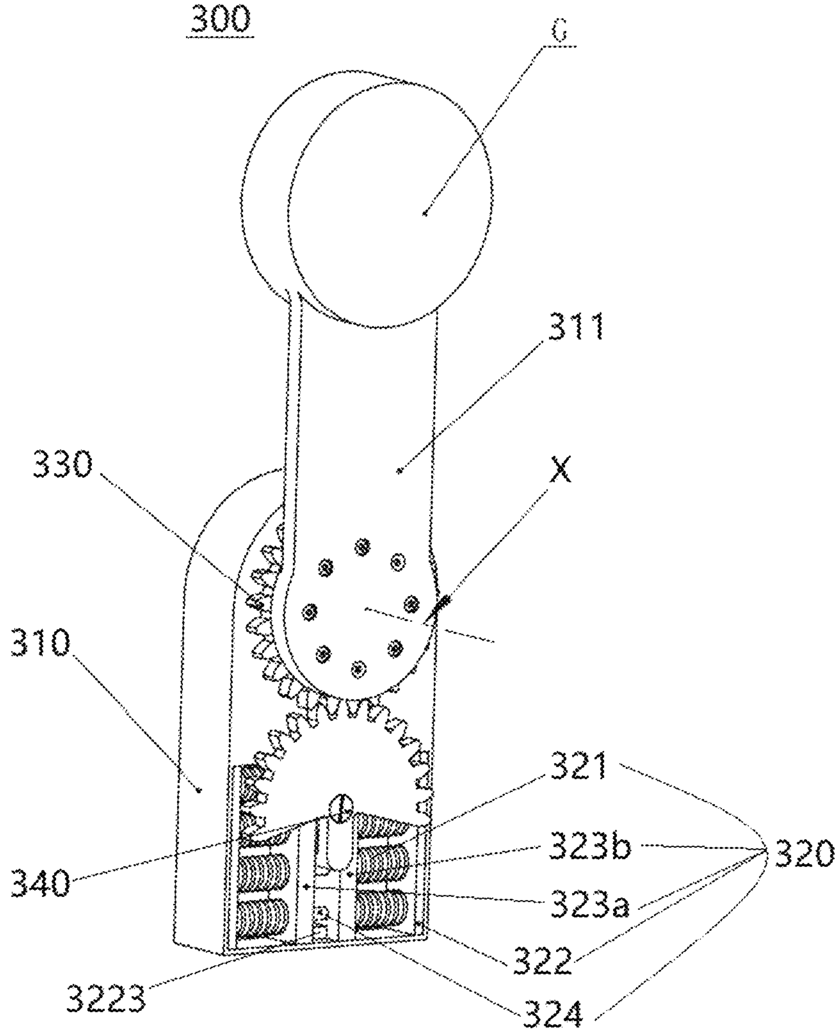
FIG. 23 shows a schematic structural diagram of a torque balancing device according to some embodiments of the present disclosure.
Figure 24:
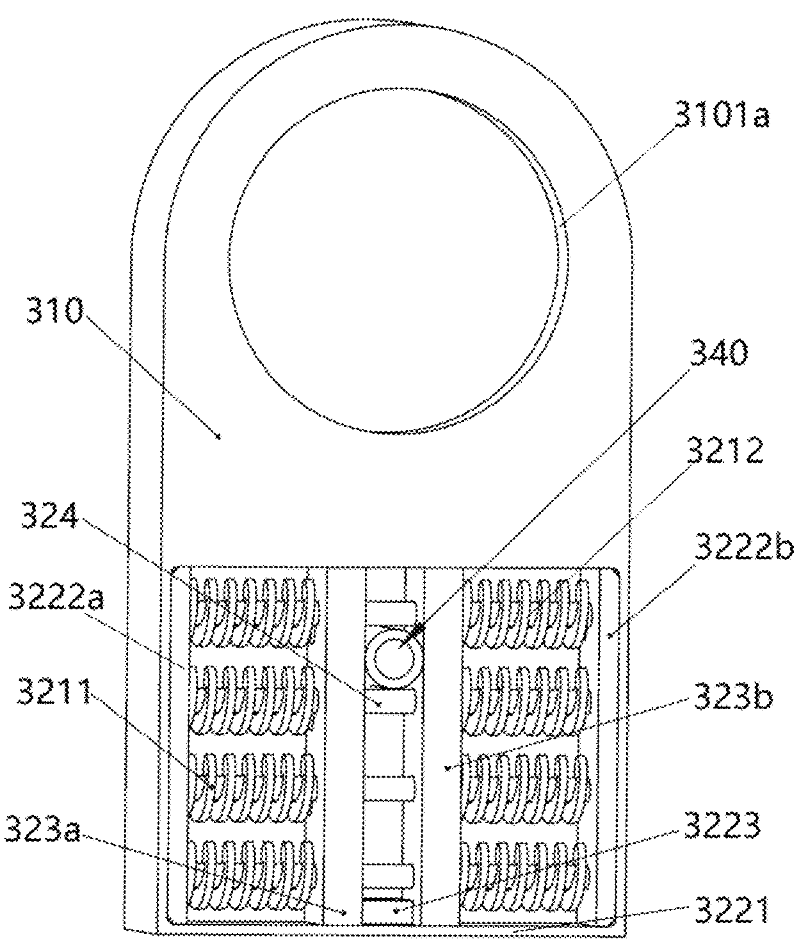
FIG. 24 shows a partial schematic structural diagram of a torque balancing device according to some embodiments of the present disclosure.

FIGS. 23 and 24 respectively show a schematic structural diagram and a partial schematic structural diagram of a torque balancing device 300 according to some embodiments of the present disclosure.

In some embodiments, as shown in FIG. 23, an elastic part 320 may comprise a mounting seat 322, a first sliding press block 323*a*, a second sliding press block 323*b*, and compression springs 321. As shown in FIG. 24, the compression springs 321 may comprise a first group of compression springs 3211 and a second group of compression springs 3212. The first and second sliding press blocks 323*a-b* are respectively slidably arranged on guiding posts 324, and the first group of compression springs 3211 and the second group of compression springs 3212 may respectively be sleeved on the guiding posts 324 located between the first and second sliding press blocks 323*a-b* and wing plates 3222*a-b* of the mounting seat 322. One end of each of the first group of compression springs 3211 and one end of each of the second group of compression springs 3212 respectively abut against the first and second wing plates 3222*a-b* of the mounting seat 322, and the other end of each of the first group of compression springs 3211 and the other end of each of the second group of compression springs 3212 respectively abut against the first and second sliding press blocks 323*a-b*. In some embodiments, at least one limiting block 3223 is provided on a web plate 3221 of the mounting seat 322 between the first and second sliding press blocks 323*a-b* to restrict displacements of the first and second sliding press blocks 323*a-b*.

Figure 25:
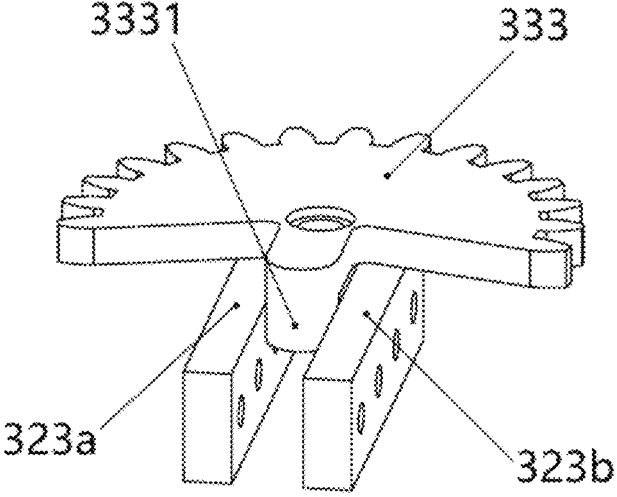
FIG. 25 shows a schematic structural diagram of the driven gear according to some embodiments of the present disclosure.
Figure 26:
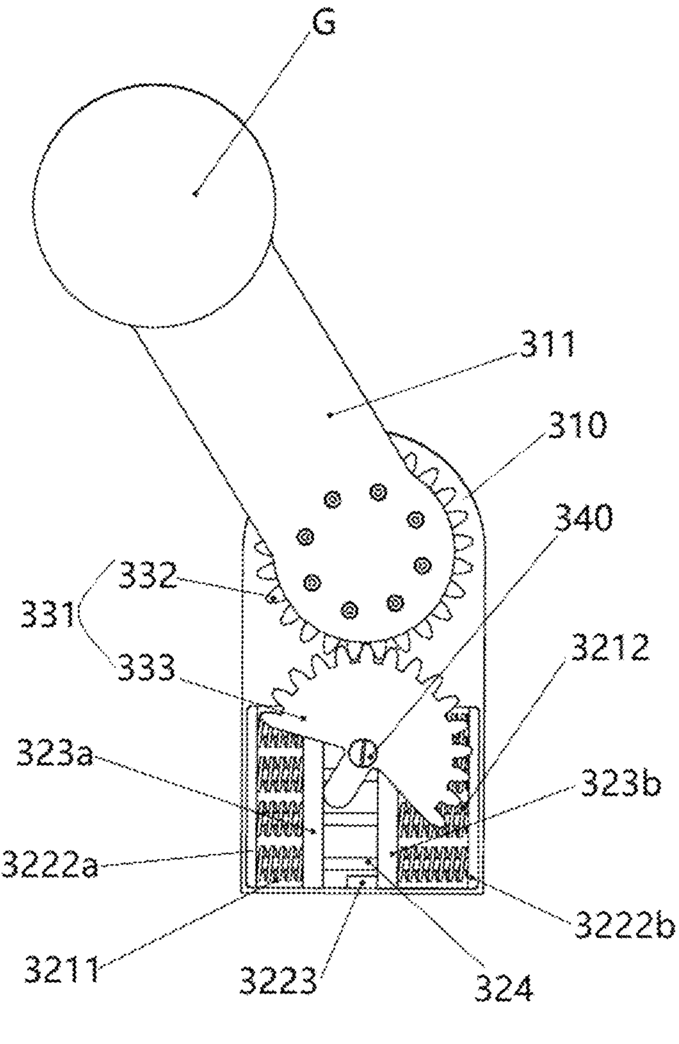
FIG. 26 shows a schematic state diagram of a second body rotating counterclockwise according to some embodiments of the present disclosure.

In some embodiments, a transmission part 330 may comprise a gear transmission mechanism 331, and the gear transmission mechanism 331 may comprise a driving gear 332 and a driven gear 333. FIG. 25 shows a schematic state diagram of the driven gear 333 according to some embodiments of the present disclosure, and FIG. 26 shows a schematic state diagram of a second body 311 rotating counterclockwise according to some embodiments of the present disclosure. As shown in FIGS. 25 and 26, the driving gear 332 is fixedly arranged at a second connection end of the second body 311, and the second connection end of the second body 311 may be rotatably connected to a first body 310 by means of a rotating shaft (not shown) or a bearing, thereby driving the driving gear 332 to rotate with the second body 311 relative to the first body 310. The driven gear 333 may be rotatably connected to the first body 310 by means of a gear connecting pin 340 and engages with the driving gear 332. It should be understood that the gear connecting pin 340 may also form a limiting block 3223 to restrict the displacements of the first and second sliding press blocks 323*a-b*. In some embodiments, the driven gear 333 may be in the form of a major arc sector. It should be understood that the driven gear 333 may also be semi-circular or sector-shaped, etc. A lever block 3331 is formed on a side of the driven gear 333 opposite a tooth surface, the lever block 3331 is located on the other opposite sides of the first and second sliding press blocks 323*a-b* that are respectively in contact with the first compression spring 3211 and the second compression spring 3212, and the lever block 3331 extends into a gap between the first and second sliding press blocks 323*a-b*. The lever block 3331 is configured for pushing the first sliding press block 323*a* or the second sliding press block 323*b* in a direction away from an axis of rotation of the driven gear 333 as the driven gear 333 rotates, and other parts of the driven gear 333 except the lever block 3331 are not in contact with the first and second sliding press blocks 323*a-b*.

In an initial state (as shown in FIG. 23), the center of gravity of the load G is located directly above the axis of rotation X of the rotating shaft, and at this time, the gravity of the load G does not generate a torque to the rotating shaft. At this time, the left first sliding press block 323*a* rightwards abuts against the limiting block 3223 on the mounting seat 322 under the action of the first group of compression springs 3211, and the right second sliding press block 323*b* leftwards abuts against the limiting block 3223 on the mounting seat 322 under the action of the second group of compression springs 3212, and at this time, the first group of compression springs 3211 and the second group of compression springs 3212 are substantially in a relaxed state except for a slight preload, and the first group of compression springs 3211 and the second group of compression springs 3212 have no acting force on the rotating shaft or the second body 311, and the entire device is in a balanced state in this case.

As shown in FIG. 26, when the second body 311 rotates to the left (the term "left" herein refers to a counterclockwise direction as viewed in a direction perpendicular to the page plane of FIG. 26), the rotating shaft rotates in the counterclockwise direction (the term "counterclockwise" herein refers to a counterclockwise direction as viewed in the direction perpendicular to the page planes of FIGS. 23 and 26), the load G generates a counterclockwise torque to the rotating shaft, and the driven gear 333 rotates clockwise in this case under the action of the driving gear 332, thereby driving the lever block 3331 of the driven gear 333 to move to the left. The lever block 3331 pushes the left first sliding press block 323*a* to compress the first group of compression springs 3211 on the left side, and the first group of compression springs 3211 on the left side generates a resilient force to limit the leftward movement of the left first sliding press block 323*a*, thereby achieving the effect of balancing the counterclockwise torque caused by the load G. Meanwhile, the second group of compression springs 3212 on the right side is in the original state under the restriction of the right second sliding press block 323*b* (cannot move to the left due to the restriction by the limiting block 3223).

Figure 27:
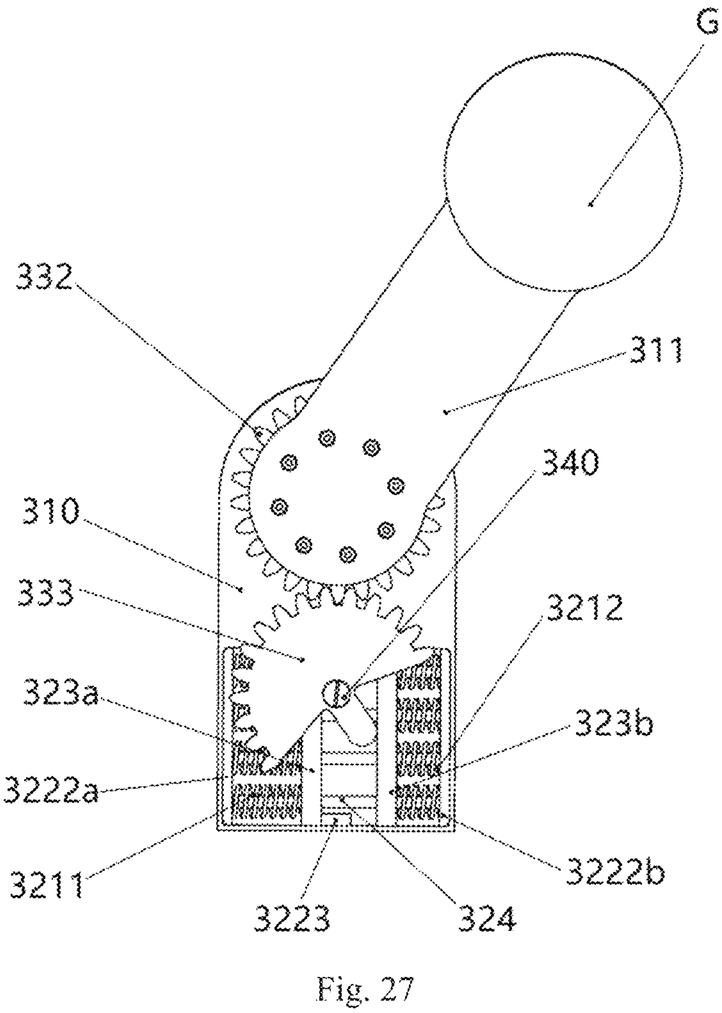
FIG. 27 shows a schematic state diagram of the second body rotating clockwise according to some embodiments of the present disclosure.

FIG. 27 shows a schematic state diagram of the second body 331 rotating clockwise according to some embodiments of the present disclosure. As shown in FIG. 27, when the second body 311 rotates to the right (the term "right" herein refers to a clockwise direction as viewed in a direction perpendicular to the paper plane of FIG. 27), the rotating shaft rotates in the clockwise direction (the term "clockwise" herein refers to a clockwise direction as viewed in a direction perpendicular to the paper planes of FIG. 23, and FIG. 27). The load G generates a clockwise torque to the rotating shaft, and the driven gear 333 rotates counterclockwise in this case under the action of the driving gear 332, thereby driving the lever block 3331 of the driven gear 333 to move to the right. The lever block 3331 pushes the right second sliding press block 323*b* to compress the second group of compression springs 3212 on the right side, and the second group of compression springs 3212 on the right side generates a resilient force to limit the rightward movement of the second sliding press block 323*b*, thereby achieving the effect of balancing the counterclockwise torque caused by the load G. Meanwhile, the first group of compression springs 3211 is in the original state under the restriction of the left first sliding press block 323*a* (cannot move to the right due to the restriction by the limiting block 3223).

In some embodiments, the elastic part 320 may comprise a first group of compression springs 3211 and a first sliding press block 323*a*. The first group of compression springs 3211 are sleeved on the guiding posts 324 located between the first wing plate 3222*a* located on one side of the mounting seat 322 and the first sliding press block 323*a*, one end of each of the first group of compression springs 3211 abuts against the first wing plate 3222*a* of the mounting seat 322 and the other end thereof abuts against the first sliding press block 323*a*. In some embodiments, the gear transmission mechanism 331 comprises: a driving gear 332 and a driven gear 333. The lever block 3331 on the driven gear 333 is located on the other opposite side of the first sliding press block 323*a* that is in contact with the first group of compression springs 3211. It is thus possible to form an unidirectional power-assistance torque balancing device 300.

Figure 28:
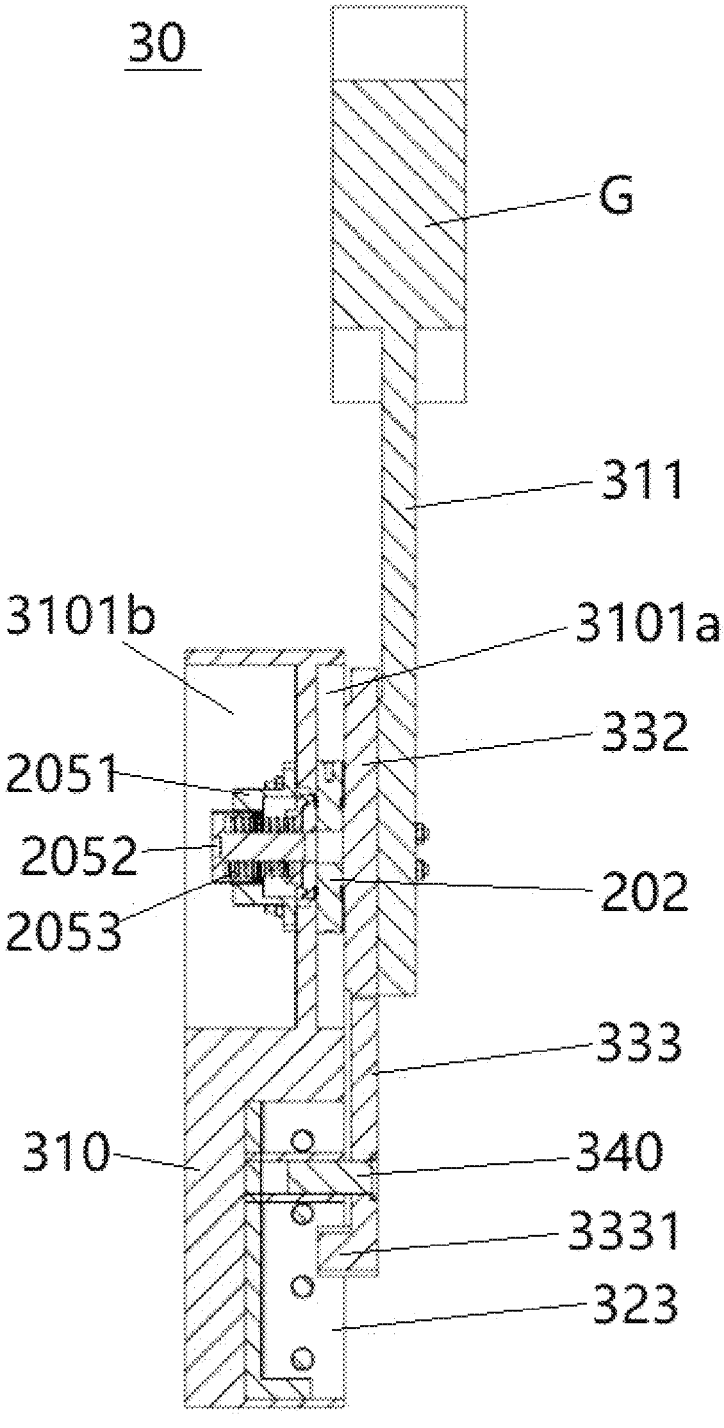
FIG. 28 shows a cross-sectional view of a self-balancing joint according to some embodiments of the present disclosure.

FIG. 28 shows a cross-sectional view of a self-balancing joint 30 according to some embodiments of the present disclosure. In some embodiments, as shown in FIG. 28, the self-balancing joint 30 provided by the present disclosure may comprise a torque balancing device 300 to achieve torque balancing when subjected to an external force or a load G.

In some embodiments, the self-balancing joint 30 may further comprise a damping adjustment mechanism 201.

As shown in FIGS. 28, 19, and 20, the retainer 2051 of the adjustable damping mechanism 201 may be fixedly connected to the outer race 2022 of the rotating part 202 and the first body 310 by means of the bolts 206 and the nuts 207. The first friction part 203 is fixedly connected to the inner race 2021 of the rotating part 202 and the second body 311 by means of the bolts 208 and the nuts 209. The second friction part 204 is axially movably and circumferentially non-rotatably arranged on the first body 310, and a contact interface is formed between the second friction part 204 and the first friction part 203.

When the guiding member 2052 is rotated to be screwed in or out in the axial direction of the damping adjustment mechanism 201, the first elastic member 2053 is compressed or released to increase or decrease the frictional damping between the second friction part 204 and the first friction part 203 to limit relative rotation between the inner race 2021 and the outer race 2022 of the rotating part 202 and thus limit relative rotation between the second body 311 and the first body 310 that are respectively connected to the inner race 2021 and the outer race 2022 of the rotating part 202.

Figure 29A:
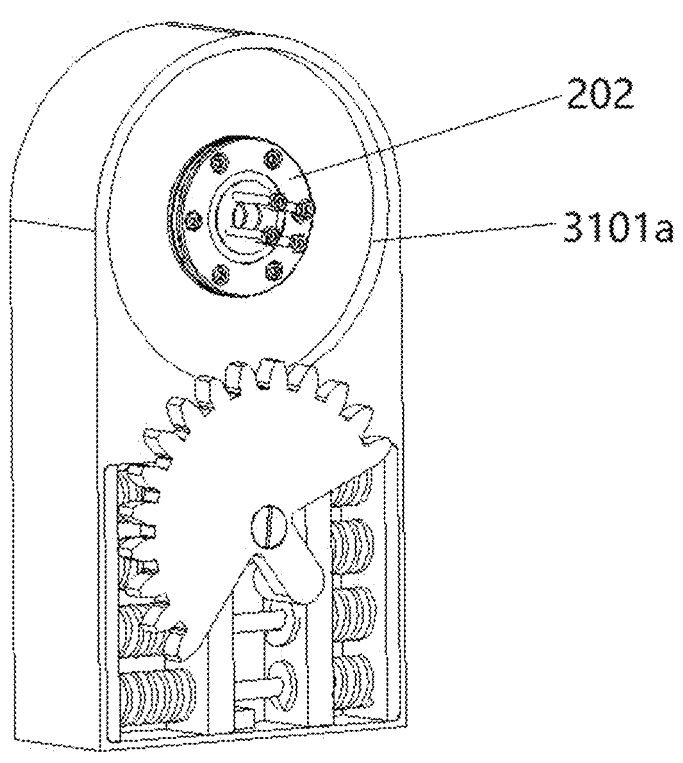
FIG. 29(*a*) shows a front view of the first body according to some embodiments of the present disclosure.
Figure 29B:
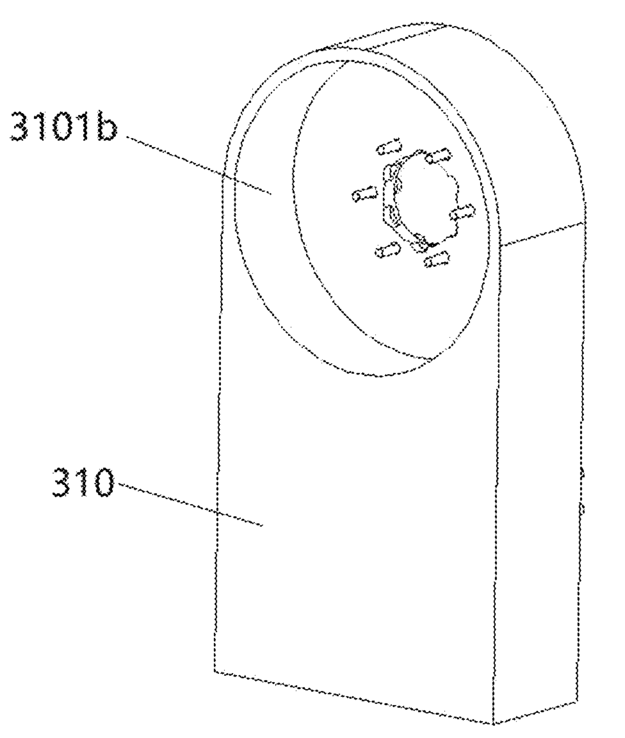

FIGS. 29(*a*) and 29(*b*) respectively show front and back views of the first body 310 according to some embodiments of the present disclosure. As shown in FIGS. 28, 29(*a*) and 29(*b*), in some embodiments, recesses 3101*a* and 3101*b* are respectively formed in the two sides of the first connection end of the first body 310. The rotating part 202 is located in the recess 3101*a*, and the retainer 3051, the first elastic member 2053, and the guiding member 2052 are located in the recess 3101*b*. A guiding channel is formed in the first body 310 between the recess 3101*a* and the recess 3101*b*, and the first friction part 203 and the second friction part 204 are located in the guiding channel.

In some embodiments, a plurality of bulging teeth are formed on the second friction part 204, a guiding groove (refer to FIGS. 29(*b*)) that fits the outer contour of the second friction part 204 is formed in the guiding channel of the first body 310, and the second friction part 204 fits in the guiding groove such that the guiding groove may limit the circumferential movement of the second friction part 204 but does not limit the movement of the second friction part 204 in the axial direction of the damping adjustment mechanism 201.

Some embodiments of the present disclosure further provide a gear locking mechanism. The torque balancing device 100 may further comprise a gear locking mechanism in some embodiments of the present disclosure. In some embodiments, the gear locking mechanism of the torque balancing device 100 is an end face tooth engagement locking mechanism 160.

Figure 30:
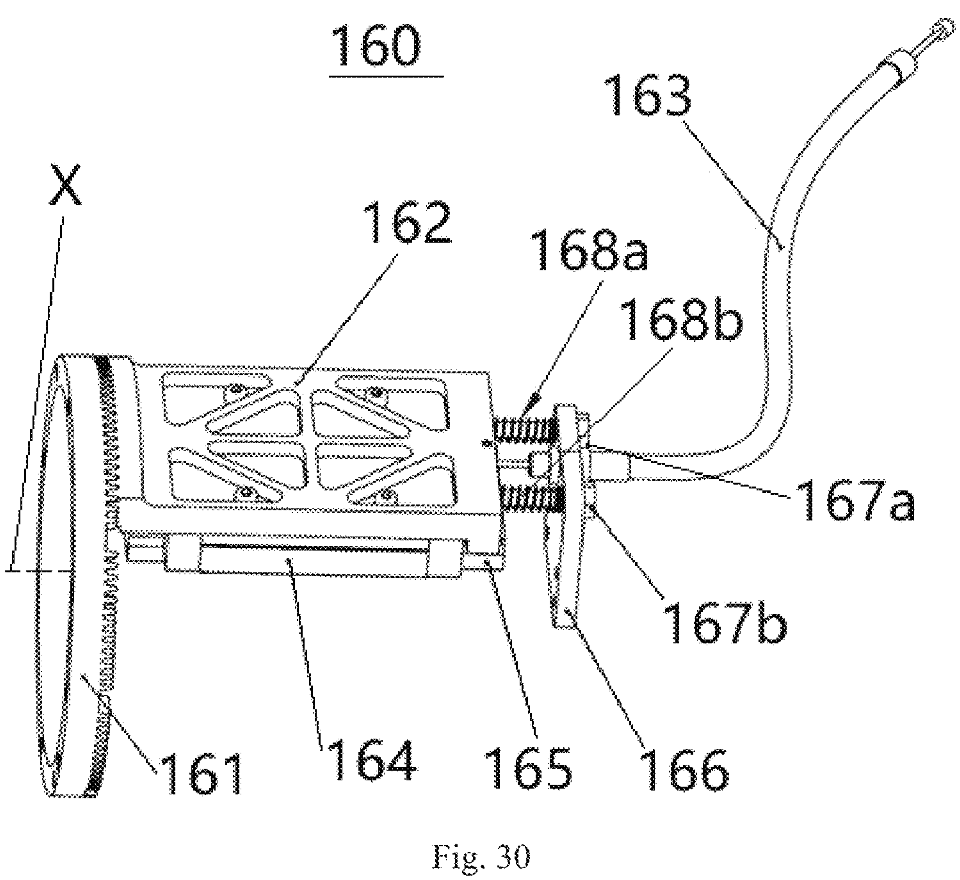
FIG. 30 shows a schematic structural diagram of an end face tooth engagement locking mechanism according to some embodiments of the present disclosure.
Figure 31:
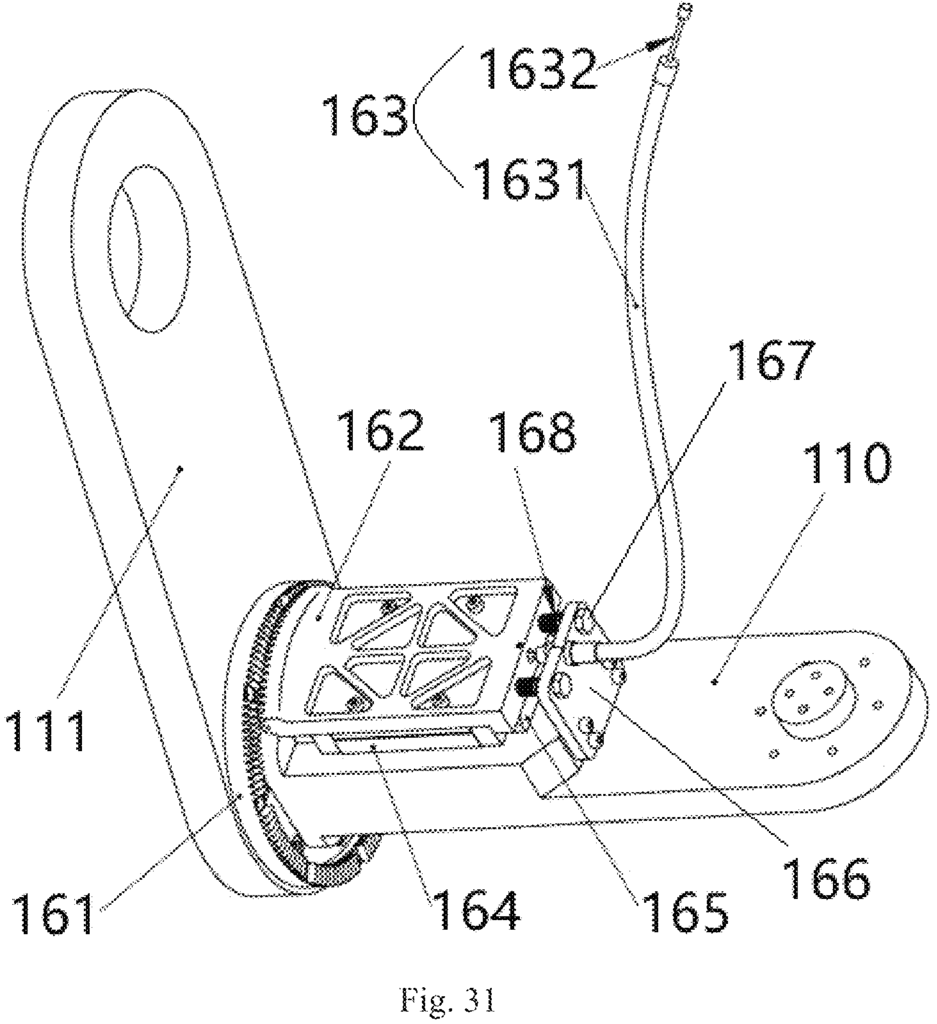
FIG. 31 shows a schematic structural diagram of a torque balancing device according to some embodiments of the present disclosure.

FIGS. 30 and 31 respectively show schematic structural diagrams of an end face tooth engagement locking mechanism 160 and a torque balancing device 100 according to some embodiments of the present disclosure. It should be understood that the end face tooth engagement locking mechanism 160 may also be applied to other joints. As shown in FIGS. 30 and 31, the end face tooth engagement locking mechanism 160 may comprise an end face toothed disk 161 and an end face tooth translation block 162. In some embodiments, the axis of rotation X of the torque balancing device 100 is parallel to the lengthwise direction of the first body 110 and perpendicular to the lengthwise direction of the second body 111. The end face toothed disk 161 may be fixed to the second body 111, and in some embodiments, the centerline of the end face toothed disk 161 is disposed coaxially with the axis of rotation X. It should be understood that the end face toothed disk 161 may be a toothed disk of which one side end face is provided with engaging teeth in a circumferential direction, the engaging teeth extending in an axial direction of the end face toothed disk 161, as shown in FIG. 30.

The end face tooth translation block 162 is movably arranged on the first body 110. In some embodiments, as shown in FIGS. 30 and 31, the end face tooth translation block 162 may be slidably arranged on the first body 110 by means of a slider 164 and a guide rail 165, a side of the end face tooth translation block 162 close to the end face toothed disk 161 has engaging teeth that mate with the end face toothed disk 161, and the end face tooth translation block 162 is movable in the lengthwise direction of the first body 110 to engage with or disengage from the end face toothed disk 161.

In some embodiments, a retaining plate 166 is fixedly arranged on the first body 110 on the other side of the end face tooth translation block 162 away from the end face toothed disk 161. As shown in FIG. 30, two guiding screws 167*a* and 167*b* may be provided on the retaining plate 166 in the lengthwise direction of the first body 110, and the two guiding screws 167*a* and 167*b* each are slidably connected to the end face tooth translation block 162 and are fixedly connected to the retaining plate 166, for example by means of threaded connection. Springs 168*a* and 168*b* may be respectively sleeved on the two guiding screws 167*a* and 167*b*, one end of each of the springs 168*a* and 168*b* abuts against the end face tooth translation block 162, and the other end of each of the springs 168*a* and 168*b* abuts against the retaining plate 166. In some embodiments, only one guiding screw 167 or three or more guiding screws 167 may be provided on the retaining plate 166, with the spring 168 being sleeved on the guiding screw 167.

As shown in FIG. 30, the end face tooth engagement locking mechanism 160 may comprise an unlocking control cable 163, wherein one end of the unlocking control cable 163 is connected to a side of the end face tooth translation block 162 away from the end face toothed disk 161, and the other end of the unlocking control cable 163 passes through the retaining plate 166 between the two guiding screws 167*a* and 167*b* for driving the end face tooth translation block 162 to move in the lengthwise direction of the first body 110 under a drawing action.

Thus, in a natural state, the springs 168*a* and 168*b* may push the end face tooth translation block 162 to engage with the end face toothed disk 161, in this case a kinematic pair between the first body 110 and the second body 111 is in a locked state, and the first body 110 and the second body 111 cannot rotate freely. When the unlocking control cable 163 is pulled with a sufficient force, the end face tooth translation block 162 slides by means of the slider 164 along the guide rail 165 in a direction away from the end face toothed disk 161, the end face tooth translation block 162 overcomes a friction force and a elastic force of the spring 168 to disengage from the end face toothed disk 161, in this case the kinematic pair between the first body 110 and the second body 111 will be in an unlocked state, and the first body 110 and the second body 111 can rotate freely.

In some embodiments, as shown in FIG. 31, the unlocking control cable 163 may comprise an outer sleeve 1631 and an inner steel wire rope 1632, wherein one end of the outer sleeve 1631 is connected to the retaining plate 166, one end of the inner steel wire rope 1632 passes through the outer sleeve 1631 and is then fixedly connected to the end face tooth translation block 162, and the other end of the inner steel wire rope 1632 may be connected to an unlocking handle (not shown) to achieve manual unlocking. In some embodiments, the other end of the inner steel wire rope 1632 may be connected to a kinematic unit (e.g., a drive unit or a transmission unit) to achieve automatic unlocking.

The torque balancing device 200 (or the torque balancing device 300) provided by the present disclosure may further comprise a gear locking mechanism. In some embodiments, the gear locking mechanism of the torque balancing device 200 (or the torque balancing device 300) is a circumferential tooth engagement locking mechanism 260.

Figure 32:
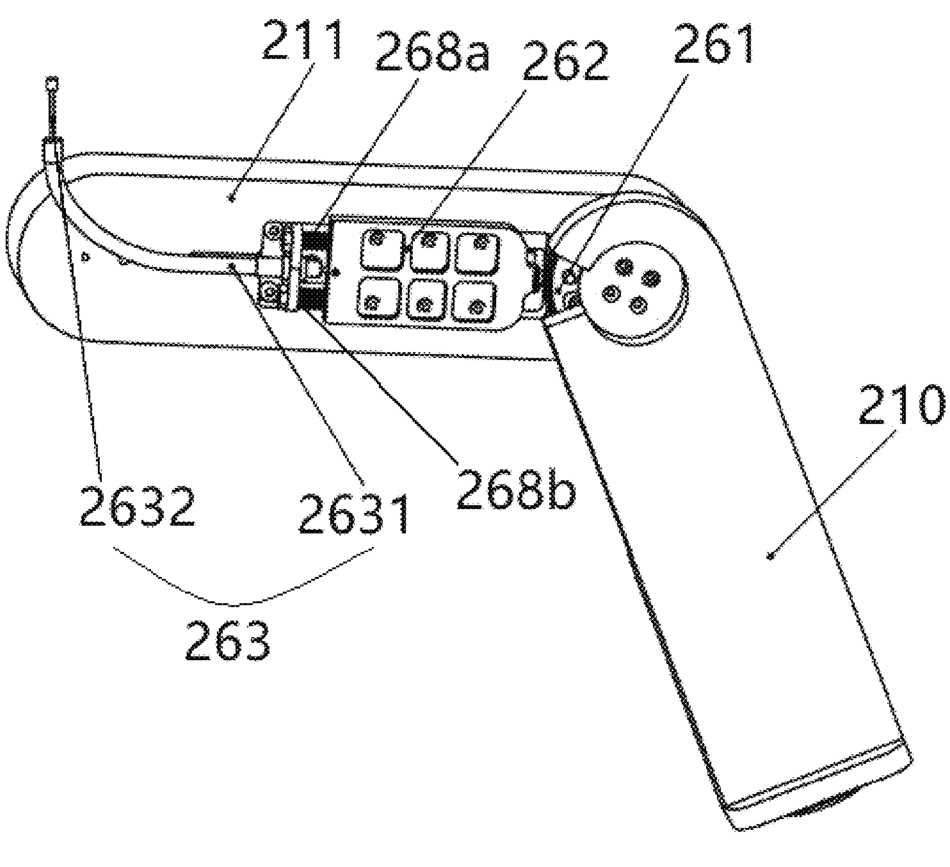
FIG. 32 shows a schematic structural diagram of a torque balancing device according to some embodiments of the present disclosure.
Figure 33:
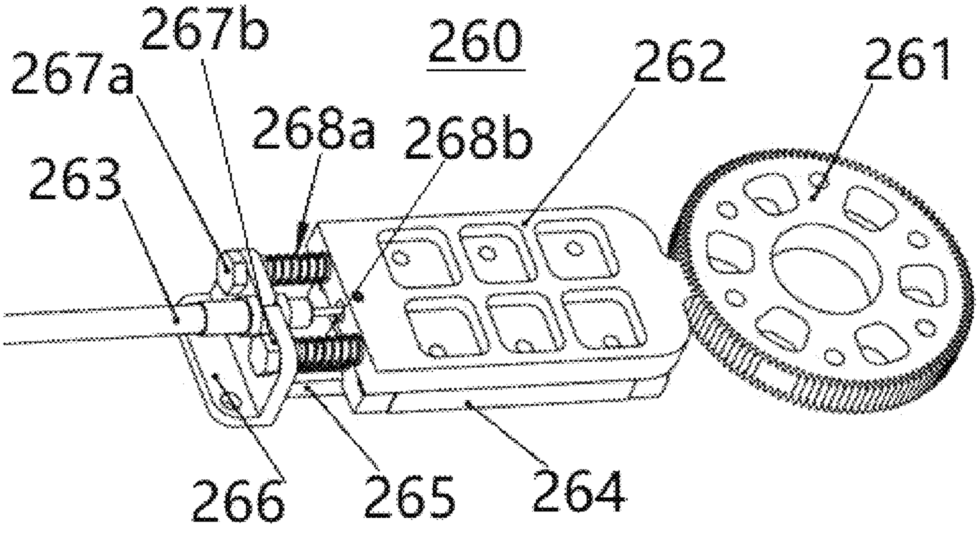
FIG. 33 shows a schematic structural diagram of a circumferential tooth engagement locking mechanism according to some embodiments of the present disclosure.
Figure 34:
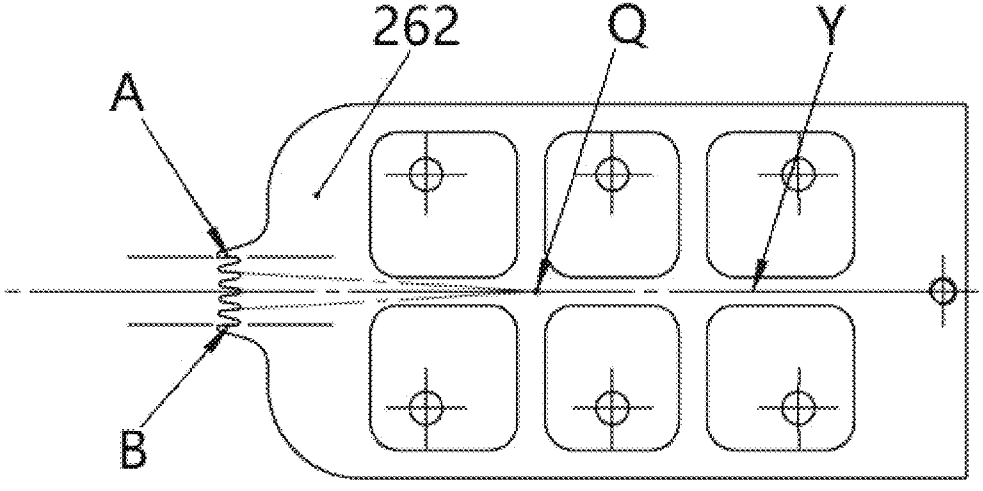
FIG. 34 shows a schematic structural diagram of a circumferential tooth translation block according to some embodiments of the present disclosure.

FIG. 32 shows a schematic structural diagram of the torque balancing device 200 (or 300) according to some embodiments of the present disclosure, and FIG. 33 shows a schematic structural diagram of the circumferential tooth engagement locking mechanism 260 according to some embodiments of the present disclosure. As shown in FIGS. 32 and 33, the circumferential tooth engagement locking mechanism 260 may comprise a circumferential toothed disk 261 and a circumferential tooth translation block 262. In some embodiments, the axis of rotation X of the torque balancing device 200 is perpendicular to the lengthwise directions of the first body 210 and the second body 211. The circumferential toothed disk 261 may be fixed to the first body 210, and in some embodiments, the centerline of the circumferential toothed disk 261 is disposed coaxially with the axis of rotation X. It should be understood that the circumferential toothed disk 261 may be a toothed disk that is provided with engaging teeth in a circumferential direction, the engaging teeth extending in a radial direction of the circumferential toothed disk 261, as shown in FIG. 33. A circumferential tooth translation block 262 is movably arranged on the second body 211, and a side of the circumferential tooth translation block 262 close to the circumferential toothed disk 261 has engaging teeth that mate with the circumferential toothed disk 261.

In some embodiments, as shown in FIG. 33, a retaining plate 266 is fixedly provided on the second body 211, two guiding screws 267*a* and 267*b* are provided on the retaining plate 266 in the lengthwise direction of the second body 211, and the two guiding screws 267*a* and 267*b* are respectively in threaded connection with the circumferential tooth translation block 262 and the retaining plate 266. Springs 268*a* and 268*b* may be respectively sleeved on the two guiding screws 267*a* and 267*b*, one end of each of the springs 268*a* and 268*b* abuts against the end face tooth translation block 262, and the other end of each of the springs 268*a* and 268*b* abuts against the retaining plate 266. In some embodiments, only one guiding screw 267, or three or more guiding screws 267 may be provided on the retaining plate 266.

One end of an unlocking control cable 263 of the circumferential tooth engagement locking mechanism 260 is connected to one side of the circumferential tooth translation block 262, and the other end of the unlocking control cable 263 may pass through the retaining plate 266 for driving the circumferential tooth translation block 262 to move in the lengthwise direction of the second body 211 under a pulling action.

Thus, in the natural state, the springs 268*a* and 268*b* may push the circumferential tooth translation block 262 to engage with the circumferential toothed disk 261, in this case the kinematic pair between the first body 210 and the second body 211 is in the locked state, and the two bodies cannot rotate freely. When the unlocking control cable 263 is pulled with a sufficient force, the end face tooth translation block 262 slides by means of the slider 264 along the guide rail 265 in a direction away from the circumferential toothed disk 261, the circumferential tooth translation block 262 overcomes a friction force and an elastic force of the spring 268 to disengage from the circumferential toothed disk 261, in this case the kinematic pair between the first body 210 and the second body 211 will be in an unlocked state, and the first body 210 and the second body 211 can rotate freely.

Some embodiments of the present disclosure further provide a band brake device. The torque balancing device 200 (or the torque balancing device 300/the self-balancing joint 20/the self-balancing joint 30) provided by the present disclosure may further comprise a band brake device 270.

Figure 35:
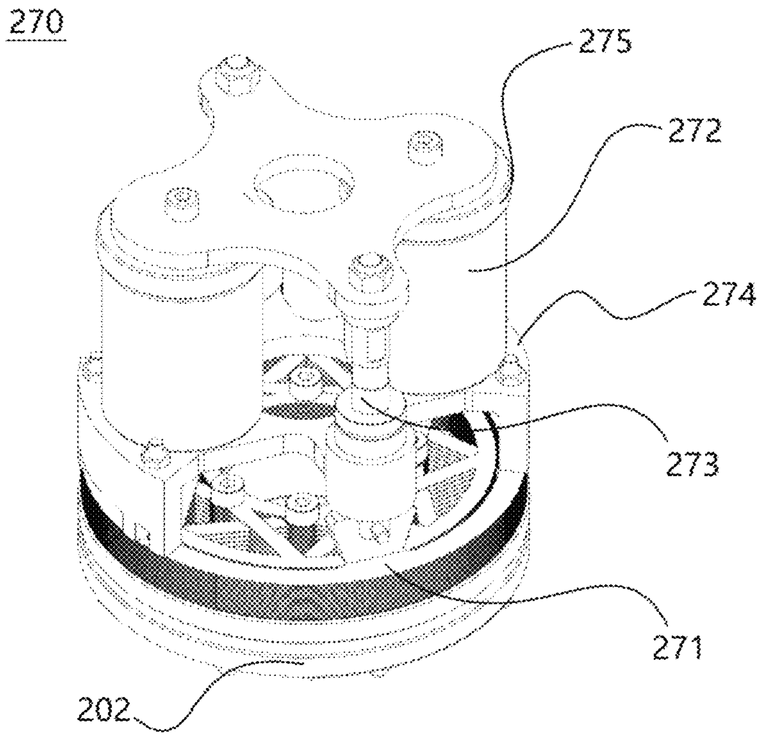
FIG. 35 shows a schematic structural diagram of a multi-sheet layer electromagnet band brake device according to some embodiments of the present disclosure.

In some embodiments, the band brake device 270 may be a multi-sheet layer electromagnet band brake device. FIG. 35 shows a schematic structural diagram of a multi-sheet layer electromagnet band brake device according to some embodiments of the present disclosure. As shown in FIG. 35, the band brake device 270 may comprise a multi-sheet layer 271, electromagnets 272, rods 273, a retainer 274, and opposite attraction blocks 275. In some embodiments, the multi-sheet layer electromagnet band brake device may comprise a pair of electromagnets 272 and a pair of rods 273 that are symmetrically arranged on the retainer 274, wherein the pair of electromagnets 272 and the pair of rods 273 may be distributed in a rectangular or parallelogram pattern. In some embodiments, the multi-sheet layer electromagnet band brake device may comprise an electromagnet 272 and a pair of rods 273, wherein the electromagnet 272 and the pair of rods 273 may be distributed in a triangular or linear pattern. It should be understood that the number and distribution of the electromagnets 272 and the rods 273 may comprise, but are not limited to, those of the embodiments described above.

Figures 36, 37:
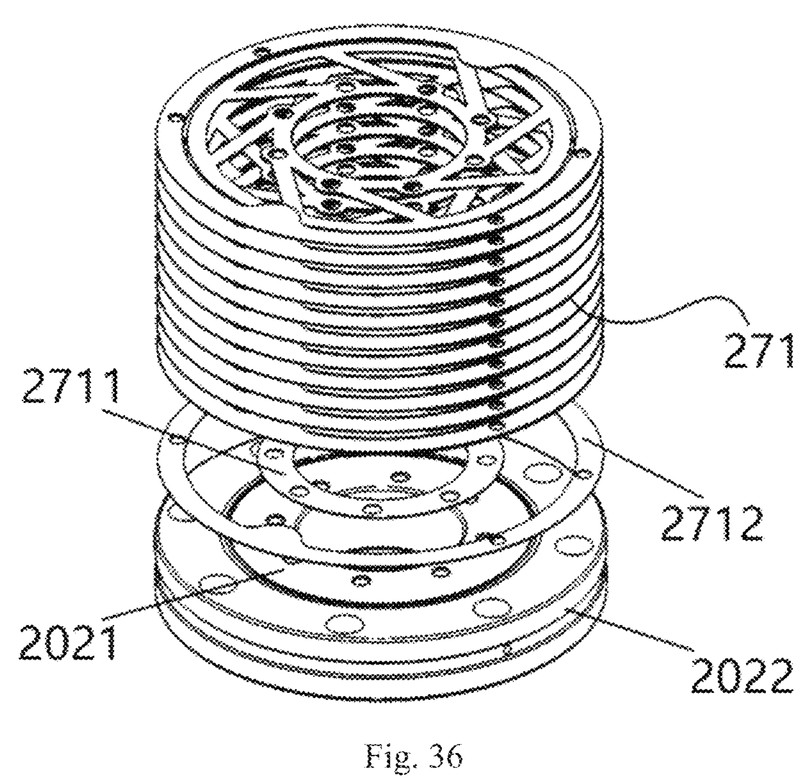
FIG. 36 shows a schematic structural diagram of a multi-sheet layer according to some embodiments of the present disclosure.
FIG. 37 shows a schematic diagram illustrating a connection between a band brake locking mechanism and a band brake device according to some embodiments of the present disclosure.

FIG. 36 shows a schematic structural diagram of a multi-sheet layer 271 according to some embodiments of the present disclosure. As shown in FIG. 36, in some embodiments, an inner race 2711 and an outer race 2712 of the multi-sheet layer 271 may be in contact respectively with the inner race 2021 and the outer race 2022 of the rotating part 202 (e.g., a cross-roller bearing) of the self-balancing joint 20 (or the self-balancing joint 30), and parts of the inner race 2711 and the outer race 2712 of the multi-sheet layer 271 overlap with a small gap therebetween. In an energized state, the electromagnet 272 provides a magnetic action, and the opposite attraction blocks 275 are attracted together by the electromagnet 272, such that the rods 273 may be driven to compress an overlapping region between the inner race 2711 and the outer race 2712 of the multi-sheet layer 271, the relative rotation of the inner race 2021 and the outer race 2022 of the rotating part 202 is locked, and the band brake device 270 is kept in a locked state. In a de-energized state, the magnetism of the electromagnet 272 disappears, the rods 273 are ejected, the inner race 2711 and the outer race 2712 of the multi-sheet layer 271 are disengaged from each other, and the inner race 2021 and the outer race 2022 of the rotating part 202 may rotate relative to each other, thereby unlocking the band brake device 270 from the locked state.

In some embodiments, the first body 210 and the second body 211 of the torque balancing device 200 (or the torque balancing device 300) may be rotatably connected by means of a crossed roller bearing, and the band brake device 270 may also achieve locking or unlocking of the torque balancing device 200 (or the torque balancing device 300).

In some embodiments, the band brake device 270 may comprise a first band brake device 270*a*. The first band brake device 270*a* may further comprise a band brake locking mechanism 280.

Figures 38, 39:
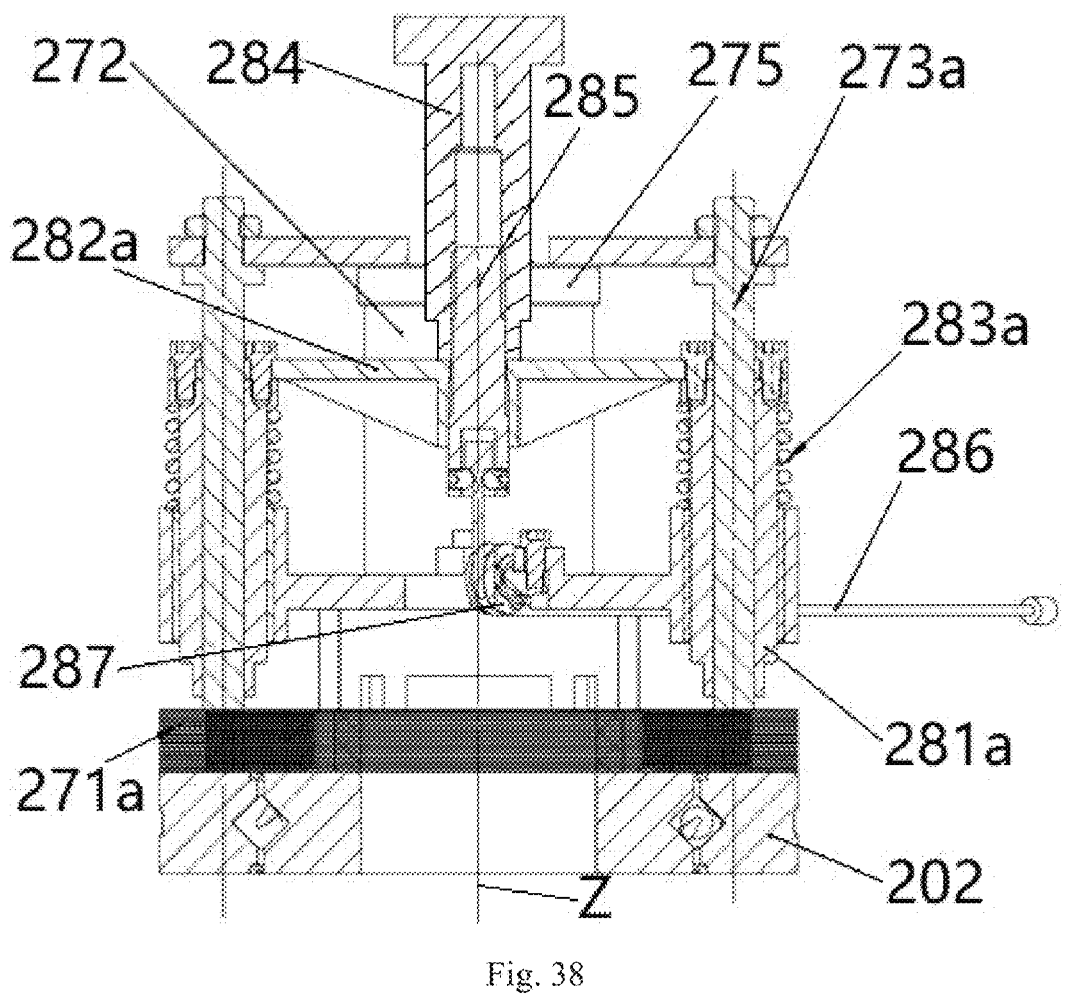
FIG. 38 shows a cross-sectional view of a band brake locking mechanism and a band brake device that are assembled according to some embodiments of the present disclosure.
FIG. 39 shows a schematic structural diagram of a band brake locking mechanism according to some embodiments of the present disclosure.

FIGS. 37 and 38 show a schematic diagram and a cross-sectional view respectively illustrating the connection and assembly of the band brake locking mechanism 280 and the band brake device 270 according to some embodiments of the present disclosure, and FIG. 39 shows a schematic structural diagram of the band brake locking mechanism 280 according to some embodiments of the present disclosure. As shown in FIGS. 37-39, in some embodiments, the band brake locking mechanism 280 may comprise first additional rods 281*a*, a first locking compression beam 282*a*, first return springs 283*a*, and an actuating component.

Figure 40:
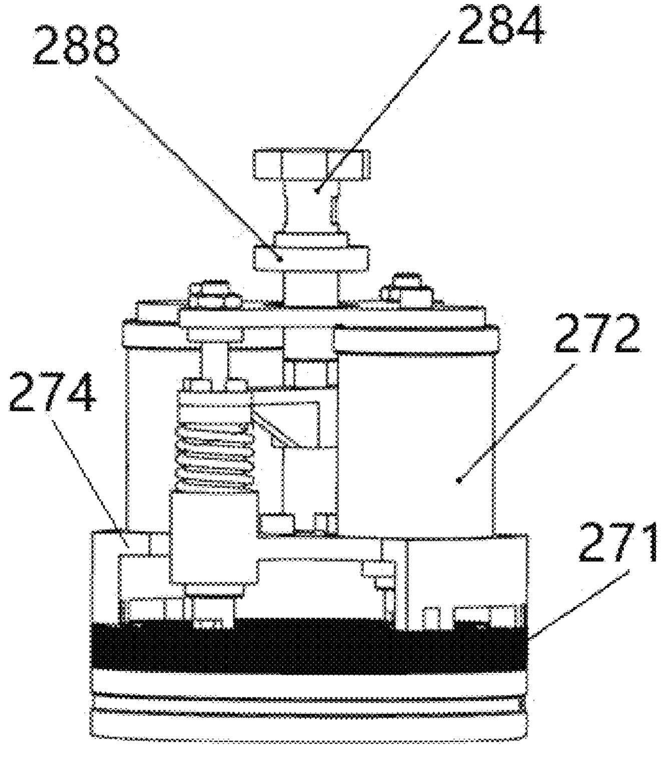
FIG. 40 shows a schematic diagram illustrating single-sided locking of a band brake locking mechanism according to some embodiments of the present disclosure.

In some embodiments, as shown in FIGS. 37-39, a pair of first additional rods 281*a* are respectively sleeved outsides of the pair of rods 273*a* of the first band brake device 270*a* and are in a clearance fit therewith, and a first end of each of the first additional rods 281*a* passes through the retainer 274 of the first band brake device 270*a* and may be used for compressing or being separated from the multi-sheet layer 271*a* of the first band brake device 270*a*. A second end of the first additional rod 281*a* is fixedly connected to the first locking compression beam 282*a*, and two ends of the first locking compression beam 282*a* are respectively movably sleeved outside the pair of rods 273*a*. In some embodiments, the actuating component may be an actuating knob 284. The actuating knob 284 may drive the first locking compression beam 282*a* to move along an axis Z of the actuating knob 284 (refer to FIG. 38). In some embodiments, as shown in FIG. 40, a stopper 288 may be provided on the actuating knob 284 to limit the range of axial movement of the actuating knob 284. A pair of first return springs 283*a* are respectively sleeved on the first additional rods 281*a*, and two ends of each of the first return springs 283*a* respectively abut against the first locking compression beam 282*a* and the retainer 274 of the first band brake device 270*a*.

FIG. 40 shows a schematic diagram illustrating single-sided locking of a band brake locking mechanism 280 according to some embodiments of the present disclosure. As shown in FIG. 40, in some embodiments, the band brake locking mechanism 280 may comprise only a first additional rod 281*a*, wherein the first additional rod 281*a* is fixedly connected to the first locking compression beam 282*a*, and one end of the first locking compression beam 282*a* is movably sleeved outside the rod 273*a*.

The first locking compression beam 282*a* may be driven to move along the axis Z of the first additional rod 281*a* by means of the actuating knob 284, such that the first additional rod 281*a* may be driven to compress or is separated from the multi-sheet layer 271*a*, and the first return spring 283*a* is compressed or released by means of the movement of the first locking compression beam 282*a* to generate a resilient force for facilitating return of the first locking compression beam 282*a* to its original position, thereby achieving the locking or unlocking of the first band brake device 270*a*. The first additional rod 281*a* and the rod 273*a* of the first band brake device 270*a* may respectively perform the function of compressing the multi-sheet layer 271*a* of the first band brake device 270*a* without influencing each other, and the band-type locking mechanism 280 may prevent the risk of entire structure failure caused by the failure in a locking function of the electromagnet 272 of the first band brake device 270*a*.

In some embodiments, as shown in FIG. 37, the band brake device 270 may further comprise a second band brake device 270*b*. The band brake locking mechanism 280 may further comprise a moving slider 285, a transfer rope 286, second additional rods 281*b*, and a second locking compression beam 282*b*.

As shown in FIGS. 38 and 39, the moving slider 285 is mounted on the first locking compression beam 282*a*, the moving slider 285 may pass through the first locking compression beam 282*a* and is in threaded connection with the actuating knob 284, the moving slider 285 makes no rotation relative to the first locking compression beam 282*a*, and makes a relative linear movement in an axial direction of the actuating knob 284. As shown in FIG. 39, the pair of second additional rods 281*b* are respectively sleeved outside the pair of rods 273*b* of the second band brake device 270*b* and are in clearance fit therewith, and a first end of each of the second additional rods 281*b* passing through the retainer 274 of the second band brake device 270*b* may be used for compressing or being separated from the multi-sheet layer 271*b* of the second band brake device 270*b*. At least one end of the second locking compression beam 282*b* is movably sleeved outside the rod 273*b* of the second band brake device 270*b* and is connected to the second end of the second additional rod 281*b*. A pair of second return springs 283*b* are respectively sleeved on a pair of second additional rods 281*b*, and two ends of each of the second return spring 283*b* respectively abut against the second locking compression beam 25 and the retainer 274 of the second band brake device 270*b*. A first end of the transfer rope 286 is connected to the moving slider 285, and a second end of the transfer rope 286 is turned by means of a turning pulley 287 mounted on the retainer 274 of the first band brake device 270*a* and is then connected to the second locking compression beam 282*b*.

Thereby, relative positions of the moving slider 285 and the first locking compression beam 282*a* may be changed by means of the actuating knob 284, and a distance between the first locking compression beam 282*a* and the second locking compression beam 282*b* may be changed by the transfer rope 286. When the distance between the first locking compression beam 282*a* and the second locking compression beam 282*b* is reduced, the first locking compression beam 282*a* and the second locking compression beam 282*b* respectively drive the first additional rods 281*a* and the second additional rods 281*b* to compress the multi-sheet layers 271*a-b* of the first band brake device 270*a* and the second band brake device 270*b* respectively. When the distance between the first locking compression beam 282*a* and the second locking compression beam 282*b* is increased, the first locking compression beam 282*a* and the second locking compression beam 282*b* respectively drive the first additional rods 281*a* and the second additional rods 281*b* away from the multi-sheet layers 271*a-b* of the first band brake device 270*a* and the second band brake device 270*b* under the action of the first return springs 283*a* and the second return springs 283*b*.

Figure 41A:
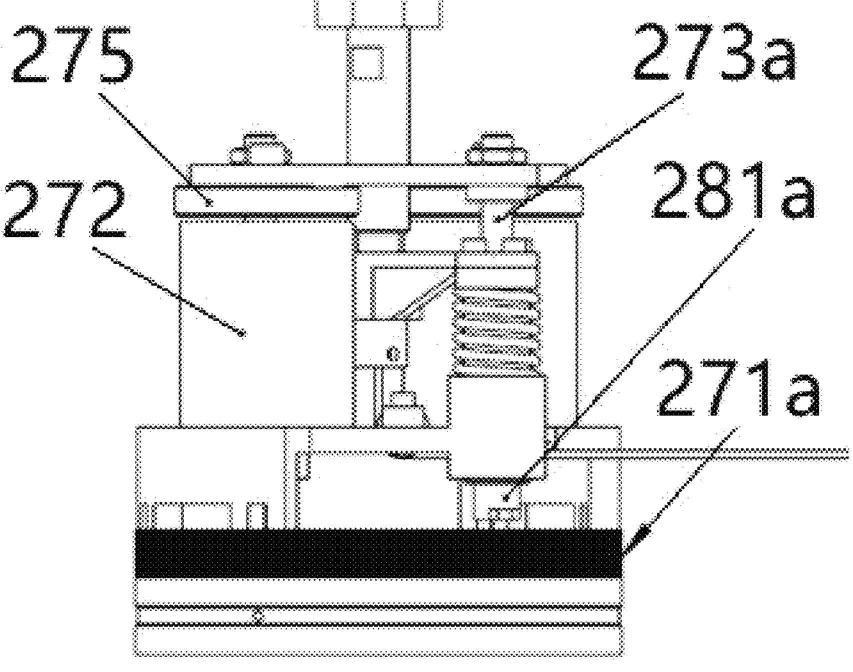
FIG. 41(*a*) shows a schematic view of positions of components of the band brake device with the electromagnet being inactive according to some embodiments of the present disclosure.
Figure 41B:
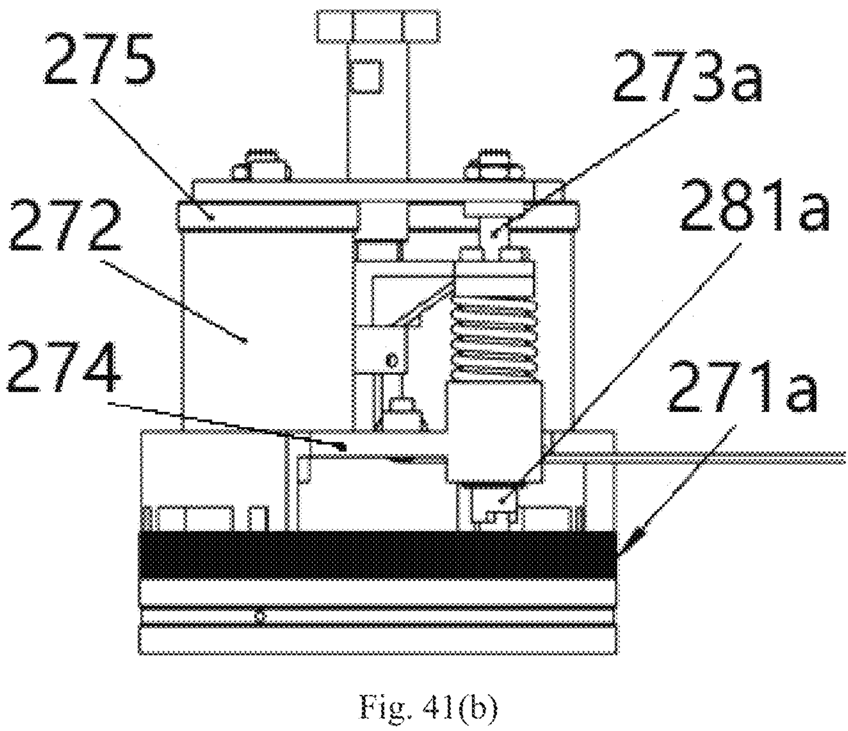
Figure 41C:
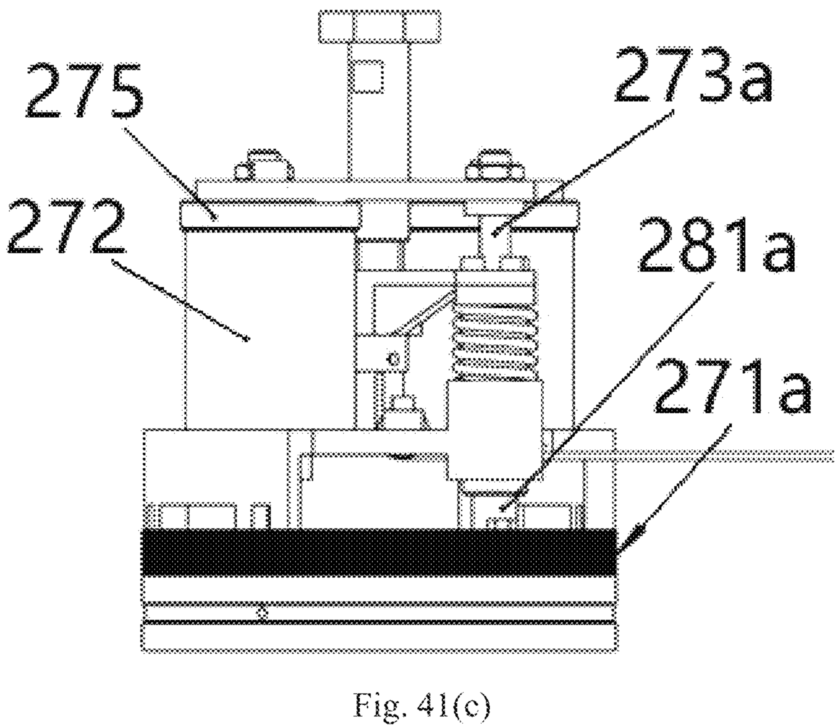

FIGS. 41 (*a*) and 41(*b*) respectively show a schematic view of positions of components of the band brake device 270 with the electromagnet 272 being inactive, and a schematic view of positions of components of the band brake device 270 with the electromagnet 272 being active according to some embodiments of the present disclosure, and FIG. 41(*c*) is a schematic view of positions of components of the band brake device 270 with both the electromagnet 272 and the band brake locking mechanism 280 being active. An operating process for cooperation of the band brake locking mechanism 280 with the band brake device 270 is as follows. In an initial state, the electromagnet 272 is de-energized (as shown in FIG. 41(*a*)), the first band brake device 270*a* is inactive, and the rod 273*a* does not compress the multi-sheet layer 271*a*. Thereafter, the electromagnet 272 is energized (as shown in FIG. 41(*b*)), the first band brake device 270*a* applies locking, the rod 273*a* compresses the multi-sheet layer 271*a*, but at this time, the first additional rod 281*a* does not compresses the multi-sheet layer 271*a* of the first band brake device 270*a*, and the band brake locking mechanism 280 is inactive. Finally, the actuating knob 284 is turned to allow the first locking compression beam 282*a* and the second locking compression beam 282*b* to move in a direction for compressing the multi-sheet layers 271*a-b* of the first band brake device 270*a* and the second band brake device 270*b* respectively, which resulting in the first additional rod 281*a* and the second additional rod 281*b* respectively compressing the multiple layers 271*a-b* of the first band brake device 270*a* and the second band brake device 270*b* (as shown in FIG. 41(*c*)). Since the first locking compression beam 282*a* and the second locking compression beam 282*b* are connected by means of the transfer rope 286, it can be achieved that the distances by which the first additional rod 281*a* and the second additional rod 281*b* respectively compress the multi-sheet layers 271*a-b* of the first band brake device 270*a* and the second band brake device 270*b* are substantially equal, thereby achieving substantially the same degree of compression.

Figure 42:
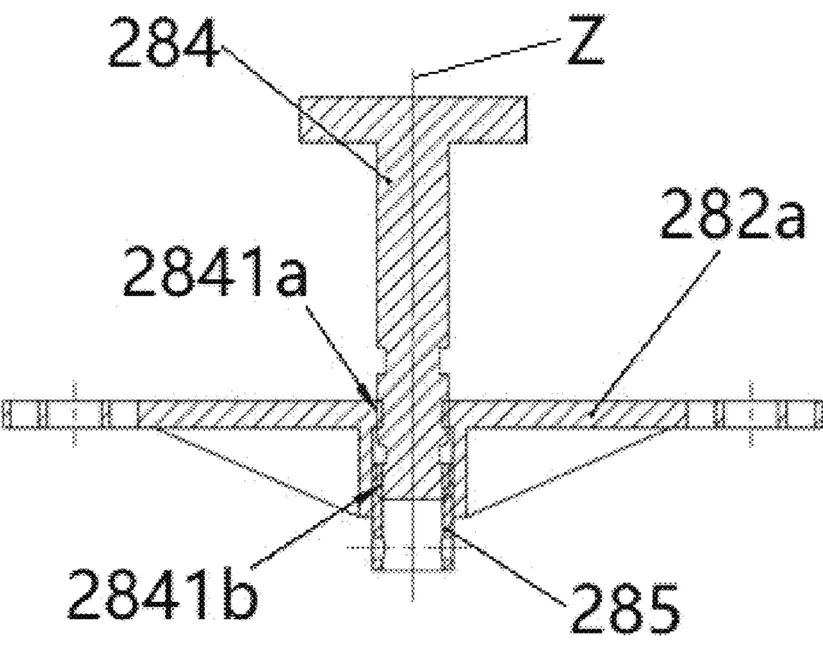
FIG. 42 shows a structural cross-sectional view of an actuating knob according to some embodiments of the present disclosure.

FIG. 42 shows a schematic structural diagram of the actuating knob 284 according to some embodiments of the present disclosure. As shown in FIG. 42, in some embodiments, the actuating knob 284 has a thread 2841*a* and a thread 2841*b* that are opposite in running directions, the thread 2841*a* and the thread 2841*b* are in threaded connection with the first locking compression beam 282*a* and the moving slider 285 respectively, and the running directions of the threads on the first locking compression beam 282*a* and the moving slider 285 respectively correspond to the running directions of the threads 2841*a* and 2841*b* on the actuating knob 284. By turning the actuating knob 284, the first locking compression beam 282*a* and the moving slider 285 may move in opposite directions along the axis Z of the actuating knob 284. Thus, the actuating knob 284 has two connections such that it is more stable during the movement. Moreover, the change in the distance between the first locking compression beam 282*a* and the moving slider 285 is twice the distance by which the actuating knob 284 travels in a circle of turn, which resulting in less total number of turns of the actuating knob 284 and a reduced travel required for achieving an additional locking function of the first and second band brake devices 270*a* and 270*b*.

Figure 43:
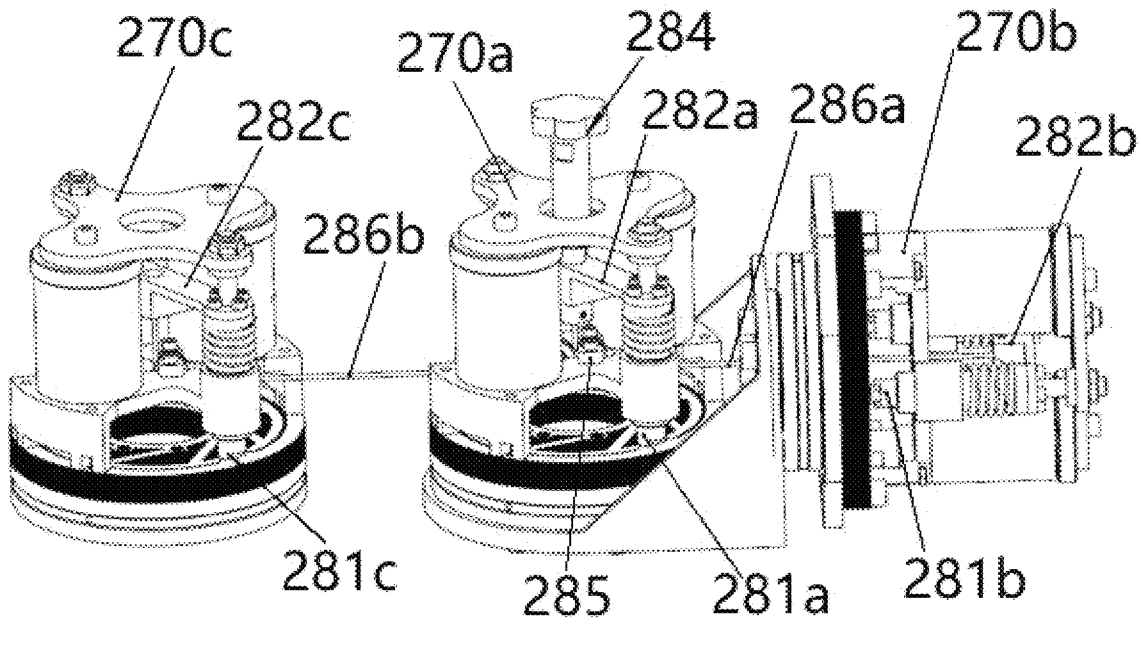
FIG. 43 shows a schematic diagram of a plurality of band brake devices locked in parallel according to some embodiments of the present disclosure.

FIG. 43 shows a schematic diagram of a plurality of band brake devices locked in parallel according to some embodiments of the present disclosure. As shown in FIG. 43, in some embodiments, the band brake device 270 may further comprise a third band brake device 270*c*. In some embodiments, as shown in FIG. 43, the first band brake device 270*a* may respectively draw the second locking compression beam 282*b* of the second band brake device 270*b* and the third locking compression beam 282*c* of the third band brake device 270*c* by leading two transfer ropes 286*a* and 286*b* (which are exemplary only, and the number of the ropes is not limited herein and may be three or more) from a lower end of the moving slider 285 so as to achieve synchronous locking of the three band brake devices, which is referred to as parallel locking.

Figure 44:
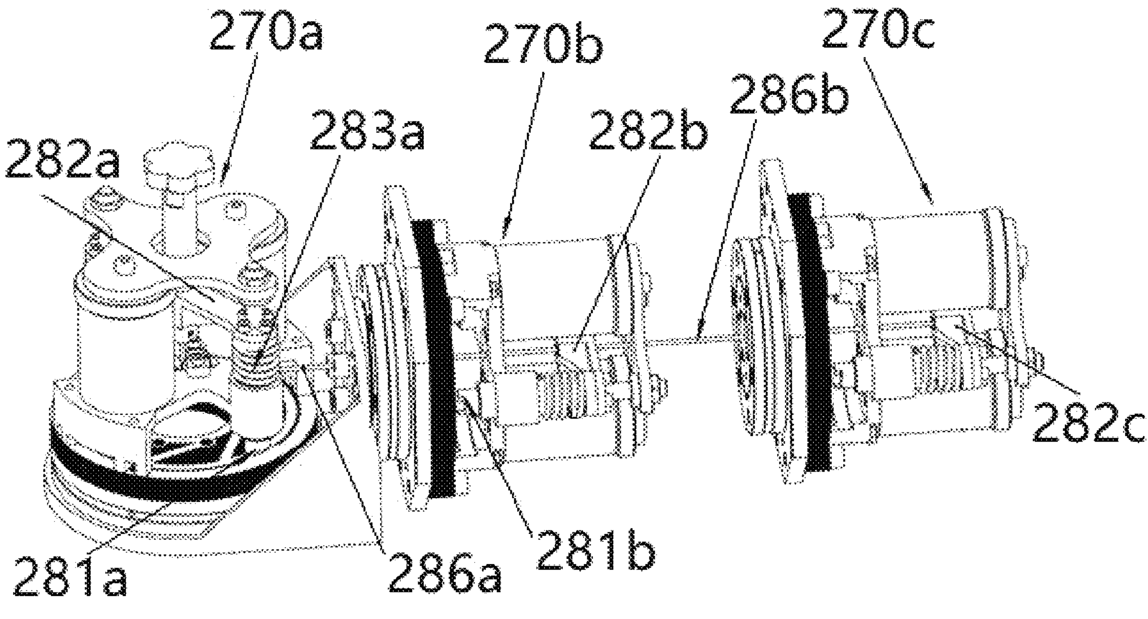
FIG. 44 shows a schematic diagram of a plurality of band brake devices locked in series according to some embodiments of the present disclosure.

FIG. 44 shows a schematic diagram of a plurality of band brake devices locked in series according to some embodiments of the present disclosure. In some embodiments, as shown in FIG. 44, a further transfer rope 286*b* may extend from the second locking compression beam 282*b* of the second band brake device 270*b* for connection to the third locking compression beam 282*c* of the third band brake device 270*c*, and so on, thereby achieving synchronous locking of the plurality of band brake devices, which is referred to as serial locking.

Figure 45:
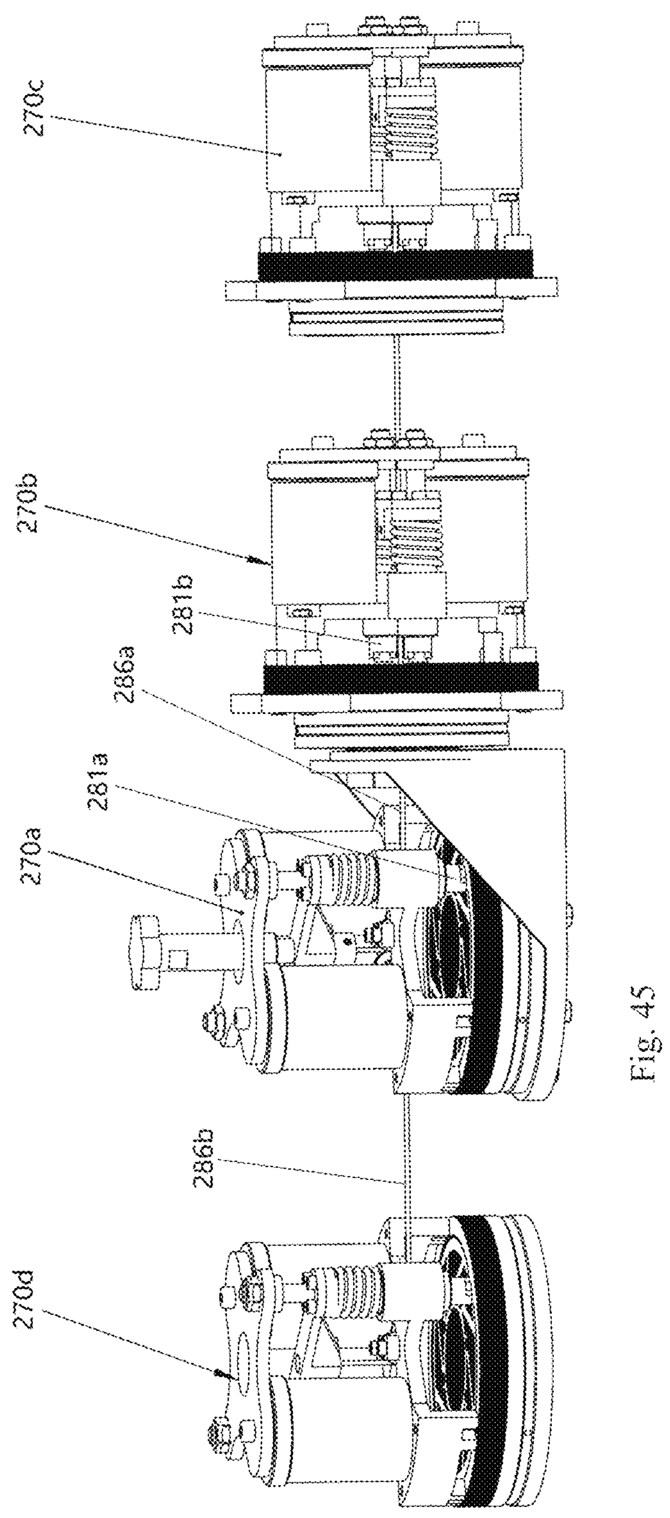
FIG. 45 shows a schematic diagram of a plurality of band brake devices locked in parallel and series according to some embodiments of the present disclosure.

FIG. 45 shows a schematic diagram of a plurality of band brake device locked in parallel and series according to some embodiments of the present disclosure. In some embodiments, as shown in FIG. 45, two transfer ropes 286*a* and 286*b* extend from the first locking compression beam 282*a* of the first band brake device 270*a*, the first band brake device 270*a* may be connected to the second band brake device 270*b* and the fourth band brake device 270*d* via the transfer ropes 286*a* and 286*b*, and a further transfer rope 286*c* extends from the second band brake device 270*b* for connection to the third band brake device 270*c*. Thereby, it may be achieved that the first, second and third band brake devices 270*a-c* are locked in series and are locked in parallel with the fourth band brake device 270*d*, and this way of using the above two connection methods of parallel locking and serial locking is referred to as hybrid locking.

Figure 46:
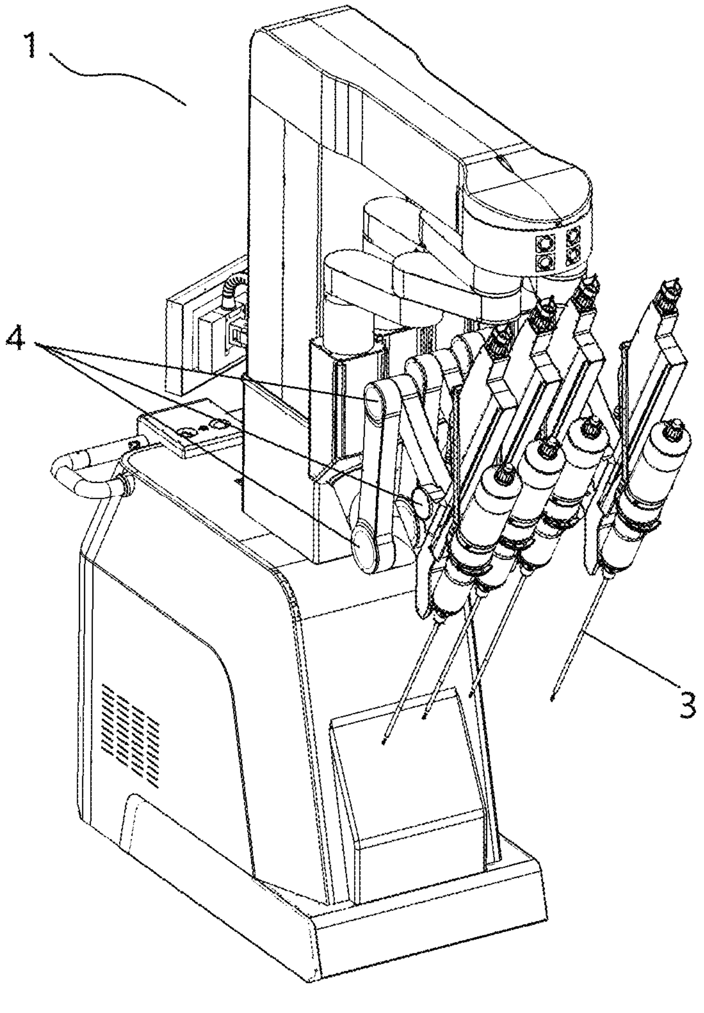
FIG. 46 shows a schematic structural diagram of a surgical robot according to some embodiments of the present disclosure.

FIG. 46 shows a schematic structural diagram of a surgical robot 1 according to some embodiments of the present disclosure. As shown in FIG. 46, the surgical robot 1 may comprise at least one kinematic joint 4. In some embodiments, the at least one kinematic joint 4 may comprise at least one of the torque balancing devices 100-300. In some embodiments, the at least one kinematic joint 4 may comprise at least one of the self-balancing joints 10-30.

Figure 47:
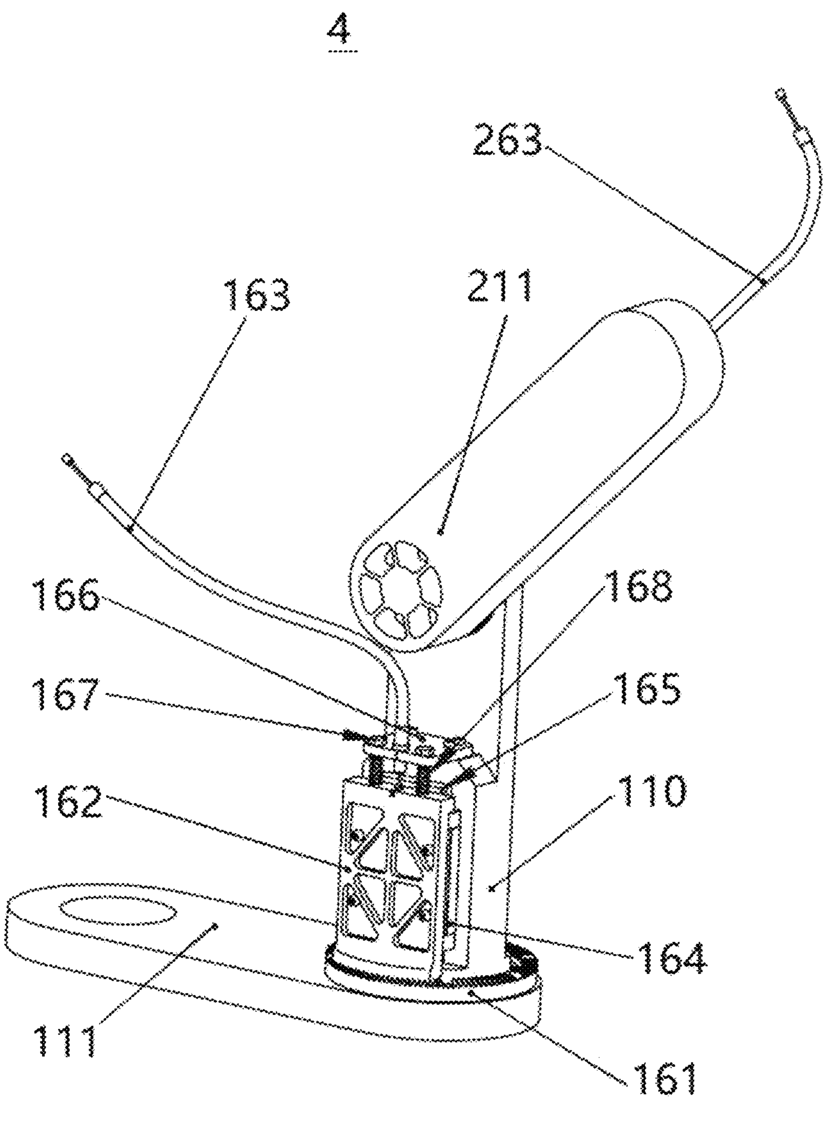
FIG. 47 shows a schematic structural diagram of a kinematic joint from one perspective according to some embodiments of the present disclosure.
Figure 48:
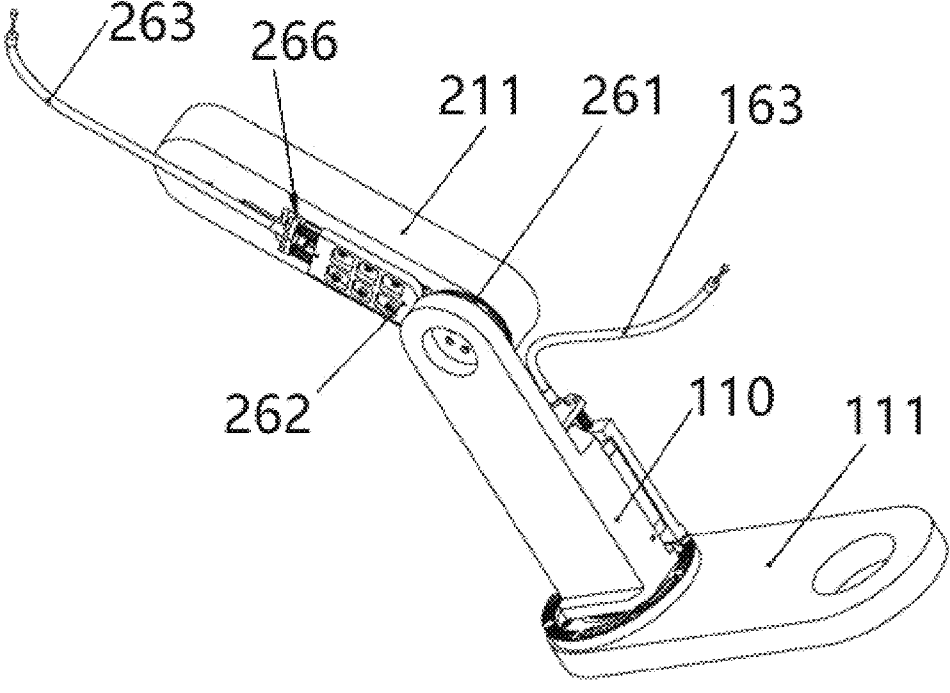
FIG. 48 shows a schematic structural diagram of a kinematic joint from another perspective according to some embodiments of the present disclosure.

FIGS. 47 and 48 respectively show schematic structural diagrams of a kinematic joint 4 from one perspective and another perspective according to some embodiments of the present disclosure. In some embodiments, the kinematic joint 4 comprises at least one torque balancing device 100 and at least one torque balancing device 200 (or 300). In this case, as shown in FIGS. 47 and 48, the torque balancing device 100 and the torque balancing device 200 share a first body 110 (or 210), a first connection end of the first body 110 of the torque balancing device 100 is connected to a second connection end of a second body 111 to form a first rotary kinematic joint, and a first opposite end of the first body 110 forms a first connection end of the first body 210 of the torque balancing device 200 for connection to a second connection end of the second body 211 to form a second rotary kinematic joint. Thus, two successive rotary kinematic joints 4 are formed.

In some embodiments, as shown in FIG. 47, an end face tooth engagement locking mechanism 160 is arranged between the first connection end of the first body 110 and the second connection end of the second body 111 of the torque balancing device 100, and may be configured for locking or unlocking the first rotary kinematic joint. As shown in FIG. 48, a circumferential tooth engagement locking mechanism 260 is arranged between the first connection end of the first body 210 (equivalent to 110 as illustrated) and the second connection end of the second body 211 of the torque balancing device 200 and may be configured for locking or unlocking the second rotary kinematic joint.

In some embodiments, an unlocking control cable 163 of the end face tooth engagement locking mechanism 160 and an unlocking control cable 263 of the circumferential tooth engagement locking mechanism 260 may be controlled by the same unlocking control cable, or may be controlled by separate unlocking control cables respectively, so as to achieve separate movement or linkage of at least the first and second rotary kinematic joints.

In some embodiments, a respective band brake device, such as first and second band brake devices 270*a* and 270*b*, may also be arranged between the first connection end of the first body 110 and the second connection end of the second body 111 of the torque balancing device 100, and between the first connection end of the first body 210 and the second connection end of the second body 211 of the torque balancing device 200, and the first and second band brake devices 270*a* and 270*b* may be configured to respectively control locking or unlocking of the first and second rotary kinematic joints. It should be understood that the band brake device may further comprise any other form of band brake stop structures that can achieve locking or unlocking.

In some embodiments, it is also possible to arranged the end face tooth engagement locking mechanism 160 at the first rotary kinematic joint, arranged a band brake device 270 at the second rotary kinematic joint, or arranged a band brake device 270 at the first rotary kinematic joint, and arranged the circumferential tooth engagement locking mechanism 260 at the second rotary kinematic joint, whereby locking or unlocking of the first rotary joint or the second rotary joint may be achieved.

Figure 49:
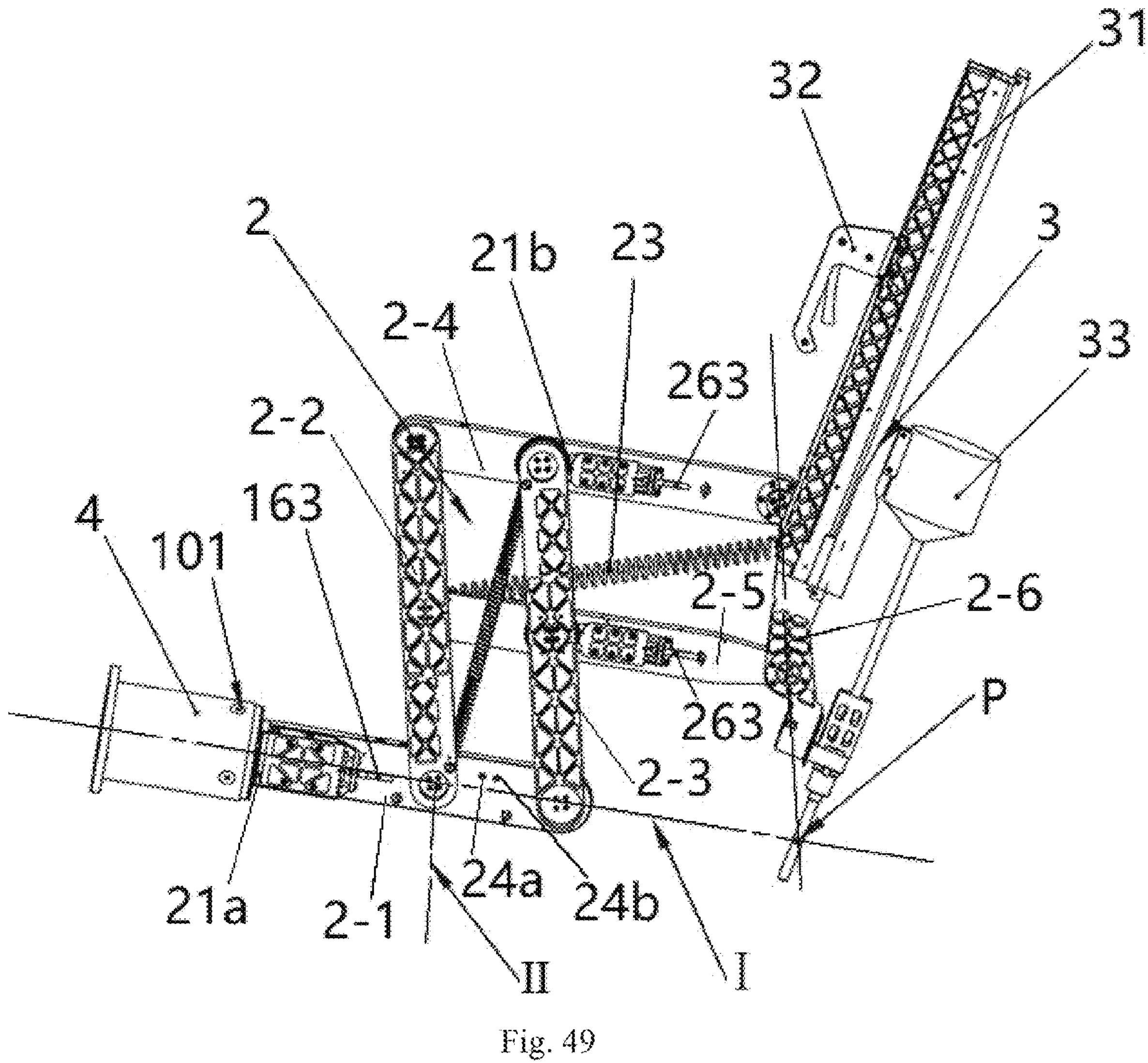
FIG. 49 shows a front view of part of a structure of a surgical robot according to some embodiments of the present disclosure.
Figure 50:
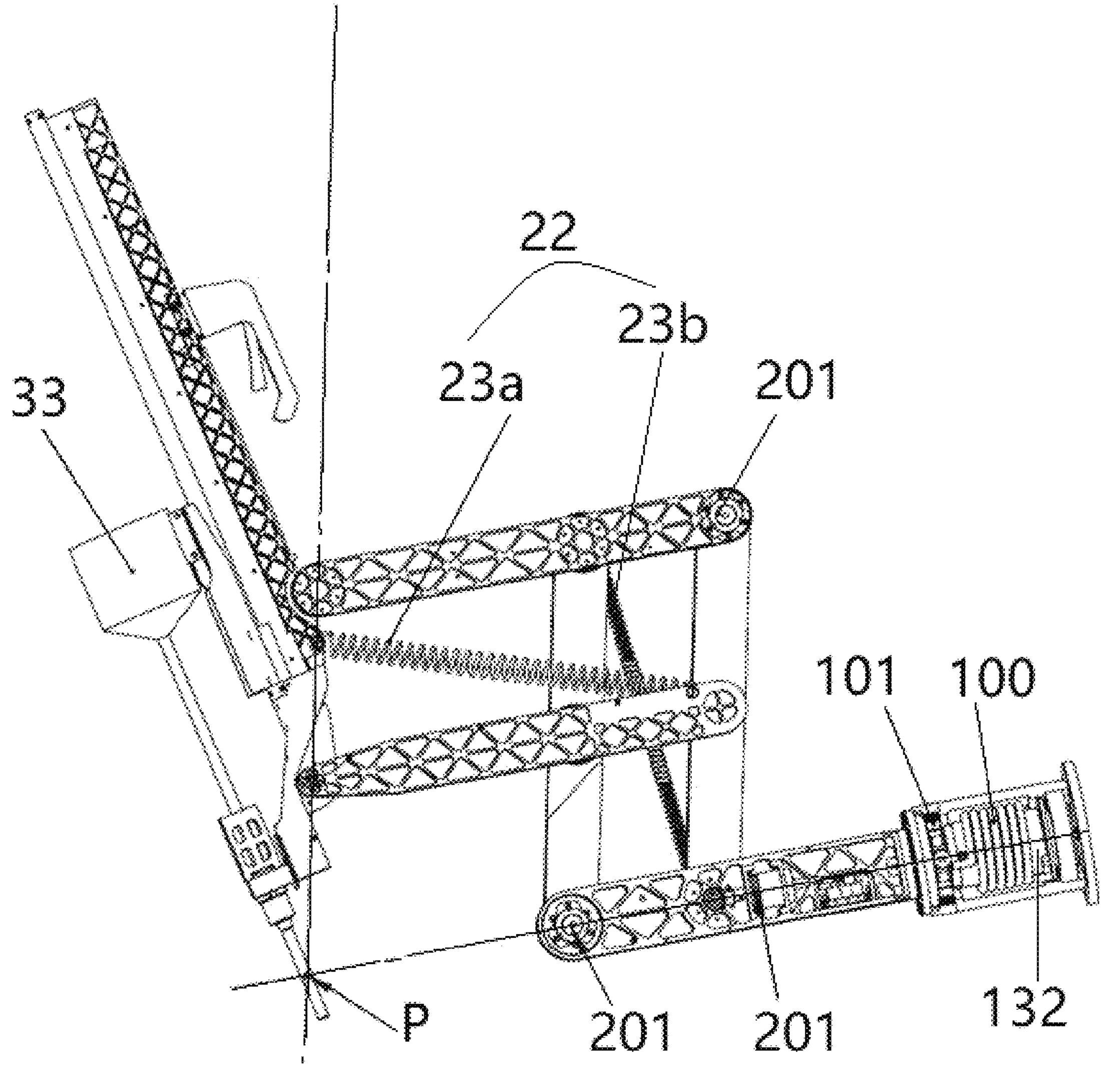
FIG. 50 shows a rear view of part of a structure of a surgical robot according to some embodiments of the present disclosure.

FIGS. 49 and 50 respectively show front and rear views of part of a structure of a surgical robot according to some embodiments of the present disclosure. As shown in the figures, in some embodiments, the surgical robot 1 may comprise: a double-parallelogram linkage 2 and a surgical device 3.

As shown in FIG. 49, the kinematic joint 4 may be connected to an input end of the double-parallelogram linkage 2, and the double-parallelogram linkage 2 rotates about an axis of rotation I of the kinematic joint 4. An output end of the double-parallelogram linkage 2 may be connected to the surgical device 3. The double-parallelogram linkage 2 has a rotational degree of freedom about an axis of articulation II thereof. The double-parallelogram linkage 2 can ensure that the axis of movement of the surgical device 3 always passes through a certain fixed point P in space, regardless of any angle of rotation about the axis of rotation I and/or the axis of articulation II. This fixed point P is a remote center of motion (RCM) of the double-parallelogram linkage 2.

In some embodiments, as shown in FIG. 49, the double-parallelogram linkage 2 may comprise: a first link 2-1, a second link 2-2, a third link 2-3, a fourth link 2-4, a fifth link 2-5 and a sixth link 2-6.

In some embodiments, one end of the first link 2-1 is fixedly connected to (or may be integrally formed with) a pivot of the kinematic joint 4, and the lengthwise direction of the first link 2-1 is parallel to the axis of rotation I of the kinematic joint 4. The second link 2-2 and the third link 2-3 are arranged in parallel and spaced apart from one another, and connections between the second link 2-2 and the third link 2-3 and the first link 2-1 each form an articulated joint. The fourth link 2-4 and the fifth link 2-5 are respectively arranged in parallel with and spaced apart from the first link 2-1, and connections between the fourth link 2-4 and the fifth link 2-5 and the second link 2-2 and the third link 2-3 each form an articulated joint. The sixth link 2-6 is arranged in parallel with and spaced apart from the second link 2-2 and the third link 2-3, and connections between the sixth link 2-6 and the fourth link 2-4 and the fifth link 2-5 each form an articulated joint, and the sixth link 2-6 is configured for carrying the surgical device 3 in such a way that the axis of the surgical device 3 always pass through the fixed point P.

In some embodiments, as shown in FIG. 50, the kinematic joint 4 may comprise a torque balancing device 100. The first link 2-1 is arranged at the first opposite end of the first body 110 of the torque balancing device 100, and is fixedly connected to a rotating shaft 132 to allow the double-parallelogram linkage 2 to freely rotate relative to the first body 110, and the axis of rotation I of the rotating shaft 132 is parallel to the lengthwise directions of the first body 110 and the first link 2-1 of the double-parallelogram linkage 2.

Thus, when the double-parallelogram linkage 2 rotates about the axis of rotation I, the stopping screw 151*a* and the stopping screw 151*b* fixedly connected to the rotating shaft 132 will be driven to rotate together (refer to FIGS. 3(*b*), 6(*b*), 6(*c*), 7(*b*) and 7(*c*)), and the stopping screw 151*a-b* will push against the outwardly extending leg 1211*a*/1211*b* corresponding thereto such that the torsion spring 121 is compressed. At this time, the outwardly extending leg 1211*a*/1211*b* on the other side of the torsion spring 121 is restrained to be immovable by the stop end A1/B2 of the limiting slot 1411*a*/1411*b*, whereby the torsion spring 121 may generate a balancing force to balance the torque caused by the double-parallelogram linkage 2 (e.g., due to the gravity), which achieves the purpose of force balance and thus may provide the function of power assistance and reduce the force exerted by an operator during operation. In some embodiments, the torque balancing device 100 may also be an unidirectional power-assistance torque balancing device.

In some embodiments, the kinematic joint 4 may be a self-balancing joint 10. In this case, the kinematic joint 4 further comprises a damping adjustment mechanism 101 as shown in FIGS. 8 and 9. Thus, when the guiding screw 1021 of the damping adjustment mechanism 101 is screwed in or out in the radial direction of the first body 110, the distance between the guiding screw 1021 and the friction member 103 may be changed, such that the amount of compression of the torsion spring 121 is changed to change a pressure of the friction member 103 on the rotating shaft 132, which in turn controls the frictional damping to which the rotating shaft 132 is subjected during rotation.

In some embodiments, as shown in FIG. 49, a first locking mechanism 21*a* is provided between the kinematic joint 4 and the input end of the double-parallelogram linkage 2, and is configured for locking or unlocking a rotation between the kinematic joint 4 and the double-parallelogram linkage 2. A second locking mechanism 21*b* is provided on at least one of the articulated joints of the double-parallelogram linkage 2, and is configured for locking or unlocking a rotation between the two links forming the articulated joint. A damping mechanism and a locking mechanism are additionally provided between the kinematic joint 4 and the input end of the double-parallelogram linkage 2 or on the double-parallelogram linkage 2, such that an optional stop function may be achieved for two degrees of freedom of the double-parallelogram linkage 2, which facilitates adjustment to an access point to the abdomen for an operator, prevents free movement of the joints and improves the surgical safety.

In some embodiments, the first locking mechanism 21*a* may comprise an end face tooth engagement locking mechanism 160 (refer to FIGS. 30 and 31). The end face toothed disk 161 is fixed to the first body 110. The end face tooth translation block 162 is slidably arranged at the input end (e.g., the first link 2-1) of the double-parallelogram linkage 2 by means of the slider 164 and the guide rail 165.

Therefore, in the natural state, at least one spring 168 will push the end face tooth translation block 162 to engage with the end face toothed disk 161, and in this case the kinematic pair between the kinematic joint 4 and the double-parallelogram linkage 2 is in the locked state, and the double-parallelogram linkage 2 cannot rotate freely. When the unlocking control cable 163 is pulled with a sufficient force, the end face tooth translation block 162 will overcome a friction force and the elastic force of the spring 168 to be disengaged from the end face toothed disk 161, the kinematic pair between the kinematic joint 4 and the double-parallelogram linkage 2 will be in the unlocked state, and the double-parallelogram linkage 2 can rotate freely.

In some embodiments, the second locking mechanism 21*b* uses the circumferential tooth engagement locking mechanism 260 (refer to FIGS. 32 and 33). The circumferential toothed disk 261 is fixed to one of the links (e.g., the third link 2-3) forming a certain articulated joint of the double-parallelogram linkage 2, the circumferential tooth translation block 262 is slidably arranged on the other link (e.g., the first link 2-1/the fourth link 2-4) forming the articulated joint of the double-parallelogram linkage 2 by means of the slider 264 and the guide rail 265, and the axis of articulation of the articulated joint is perpendicular to the lengthwise directions of both of the two links.

Thus, in the natural state, at least one spring 268 will push the circumferential tooth translation block 262 to engage with the circumferential toothed disk 261, and in this case the kinematic pair between the two links of the articulated joint of the double-parallelogram linkage 2 is in the locked state. When the unlocking control cable 263 is pulled with a sufficient force, the circumferential tooth translation block 262 will overcome a friction force and the elastic force of the spring 268 to be disengaged from the circumferential toothed disk 261, in this case the articulated joint of the double-parallelogram linkage 2 is in the unlocked state.

In some embodiments, as shown in FIG. 50, the damping adjustment mechanism 201 (refer to FIGS. 19 and 20) is further provided on the remaining at least one articulated joint of the double-parallelogram linkage 2.

In some embodiments, as shown in FIGS. 49 and 50, a gravity balancing mechanism 22 is further provided on the double-parallelogram linkage 2, the gravity balancing mechanism 22 may comprise at least one tension spring 23, and the tension spring 23 is connected to two different links of at least one parallelogram of the double-parallelogram linkage 2. When only a normal load is active, the parallelogram move in such a direction that allows the distances between the tension spring 23 and two connecting points of the parallelogram to increase, and a balancing force provided by the tension spring 23 may thus balance most of the gravity of the links and the load. As shown in FIG. 50, the gravity balancing mechanism 22 may comprise tension springs 23*a* and 23*b*, and the tension springs 23*a* and 23*b* are respectively arranged on two parallelogram diagonals of the double-parallelogram linkage 2.

In some embodiments, as shown in FIG. 49, limiting screws 24*a* and 24*b* are further provided on the first link 2-1 of the double-parallelogram linkage 2, and may be configured for limiting a torsion angle of the double-parallelogram linkage 2 within a certain range.

In some embodiments, as shown in FIG. 49, the surgical device 3 may comprise a linear module 31, an unlocking handle 32, and a surgical tool 33, the linear module 31 being arranged at the output end (e.g., the sixth link 2-6) of the double-parallelogram linkage 2, and the surgical tool 33 may be linearly fed along the linear module 31 to approach or move away from a surgical opening through the fixed point P.

Figure 51:
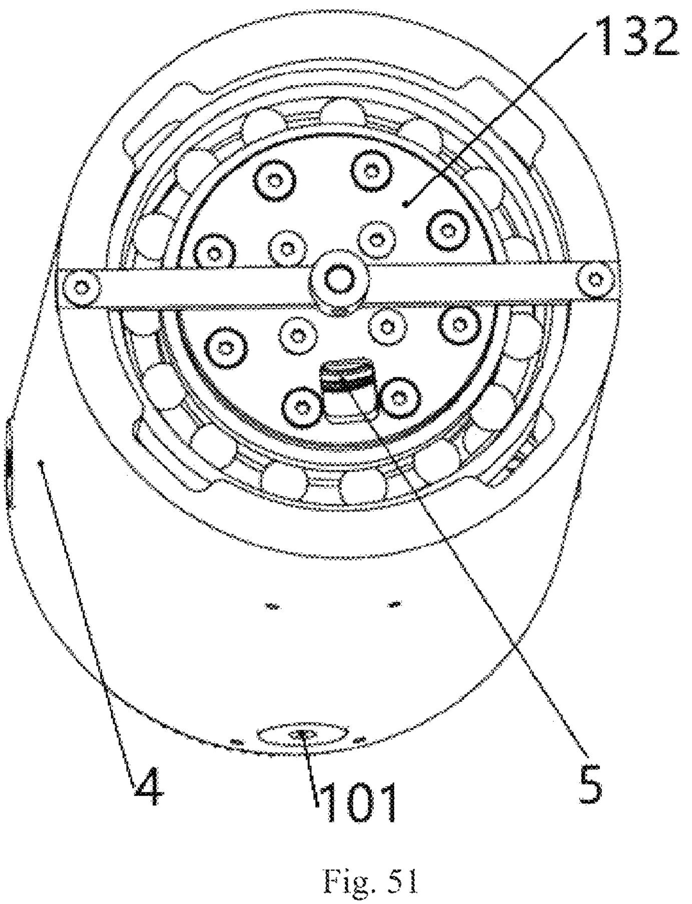
FIG. 51 shows a schematic diagram illustrating an end face structure of a kinematic joint according to some embodiments of the present disclosure.

FIG. 51 shows a schematic diagram illustrating an end face structure of a kinematic joint 4 according to some embodiments of the present disclosure. In some embodiments, as shown in FIG. 51, an encoder 5 is further provided on the kinematic joint 4 and/or at least one articulated joint of the double-parallelogram linkage 2, an accurate value of the angle of rotation of the kinematic joint 4 and/or of this articulated joint of the double-parallelogram linkage 2 may be calculated by means of the encoder 5, so as to meet the algorithm requirements during a surgery.

The present disclosure further discloses the following embodiments:

Item 1: A torque balancing device, comprising:

a first body comprising a first connection end and a first opposite end opposite to the first connection end;

a second body comprising a second connection end and a second opposite end opposite to the second connection end, the second connection end of the second body being rotatably connected to the first connection end of the first body;

an elastic part arranged in the first body; and a transmission part connected to the second body and the elastic part, the transmission part being configured to be driven by rotation of the second body relative to the first body to compress the elastic part so as to generate a torque.

Item 2: The torque balancing device of item 1, wherein the transmission part comprises:

at least one bearing comprising an inner race and an outer race that are rotatable relative to each other, the outer race of the bearing being fixedly connected to the first body; and a rotating shaft fixedly connected to the inner race of the bearing, and the rotating shaft being fixedly connected to the second body.

Item 3: The torque balancing device of item 2, the elastic part comprises a torsion spring that is sleeved outside the rotating shaft, at least one end of the torsion spring being capable of abutting against a stopping part arranged on the rotating shaft, and the stopping part being configured to position and compress the torsion spring.

Item 4: The torque balancing device of item 3, further comprising a limiting part;

the limiting part comprises at least one first limiting baffle arranged in the first body, a limiting slot for limiting the rotation of the torsion spring within an angle range being formed in the first limiting baffle, and a first end of the torsion spring being movably arranged in the limiting slot.

Item 5: The torque balancing device of item 4, wherein at least one limiting baffle further comprises at least one second limiting baffle, the second limiting baffle and the first limiting baffle being spaced apart within the first body; and the torsion spring is arranged between the first limiting baffle and the second limiting baffle, and a second end of the torsion spring is movably arranged in a limiting slot of the second limiting baffle.

Item 6: The torque balancing device of item 1, wherein the elastic part comprises:

a mounting seat mounted on the first body;

at least one sliding press block slidably arranged on the mounting seat, the sliding press block being connected to the transmission part; and at least one compression spring arranged between the mounting seat and the sliding press block;

wherein the transmission part is configured to be driven by rotation of the second body relative to the first body so as to compress the compression spring by means of the sliding press block.

Item 7: The torque balancing device of item 6, wherein the mounting seat is in the form of a recess, and at least one guiding post is provided between a first wing plate of the mounting seat and a second wing plate opposite to the first wing plate, the guiding post penetrating the sliding press block and forming a slide joint therewith.

Item 8: The torque balancing device of item 7, wherein the at least one compression spring comprises a first group of compression springs, and the at least one sliding press block comprises a first sliding press block;

the first group of compression springs are sleeved on the guiding posts between the first sliding press block and a first wing plate of the mounting seat, one end of each of the first group of compression springs abuts against the first wing plate of the mounting seat, and the other end of each of the first group of compression springs abuts against the first sliding press block.

Item 9: The torque balancing device of item 8, wherein the at least one compression spring further comprises a second group of compression springs, and the at least one sliding press block further comprises a second sliding press block;

the second group of compression springs are sleeved on the guiding posts located between the second sliding press block and the second wing plate of the mounting seat, one end of each of the second group of compression springs abuts against the second wing plate of the mounting seat, and the other end of each of the second group of compression springs abuts against the second sliding press block; and at least one limiting block is provided on a web plate of the mounting seat between the first sliding press block and the second sliding press block.

Item 10: The torque balancing device of item 8, wherein the at least one compression spring further comprises a second group of compression springs, and the elastic part further comprises a pair of sliding press plates;

the pair of sliding press plates are respectively slidably arranged on the guiding posts located on two sides of the first sliding press block, one end of each of the first group of compression springs and one end of each of the second group of compression springs respectively abut against the first and second wing plates of the mounting seat, and the other end of each of the first group of compression springs and the other end of each of the second group of compression springs respectively abut against the pair of sliding press plates; and at least one limiting block is provided on a web plate of the mounting seat between the pair of sliding press plates.

Item 11: The torque balancing device of any one of items 6-10, wherein the transmission part comprises: a gear transmission mechanism or a pulley transmission mechanism.

Item 12: The torque balancing device of item 11, wherein the transmission part is a gear transmission mechanism comprising:

a driving gear fixedly arranged at the second connection end of the second body and capable of rotating with the second body relative to the first body; and a driven gear rotatably connected to the first body by means of a pin and engaging with the driving gear.

Item 13: The torque balancing device of item 12, wherein a lever block is formed on the driven gear and located on the other side opposite to that of the sliding press block in contact with the elastic member, and the lever block is configured to push the sliding press block under the drive by means of the rotation of the driven gear so as to compress the elastic member.

Item 14: The torque balancing device of item 11, wherein the transmission part is a pulley transmission mechanism comprising:

an adapter block fixedly arranged at the second connection end of the second body;

a first pulley set; and a first traction rope located on one side of the adapter block, one end of the first traction rope being connected to the adapter block, and the other end of the first traction rope being turned by the first pulley set and then being fixedly connected to the first wing plate of the mounting seat on the same side as the first traction rope.

Item 15: The torque balancing device of item 14, wherein the pulley transmission mechanism further comprises:

a second pulley set; and a second traction rope located on the other side of the adapter block, one end of the second traction rope being connected to the adapter block, and the other end of the second traction rope being turned by the second pulley set and then being fixedly connected to the second wing plate of the mounting seat on the same side as the second traction rope.

Item 16: The torque balancing device of item 15, wherein the first pulley set comprises:

a first fixed pulley set rotatably arranged on the first wing plate of the mounting seat; and a first movable pulley set rotatably arranged on the sliding press block;

and the second pulley set comprises:

a second fixed pulley set rotatably arranged on the second wing plate of the mounting seat; and a second movable pulley set rotatably arranged on the sliding press block.

Item 17: The torque balancing device of item 16, further comprising first and second traction rope adjustment parts, wherein the other ends of the first traction rope and the second traction rope are fixedly connected to the mounting seat respectively by means of the first and second traction rope adjustment parts, and the first and second traction rope adjustment parts are respectively configured to adjust positions of the first traction rope and the second traction rope.

Item 18: The torque balancing device of item 1, further comprising: a locking mechanism;

wherein the locking mechanism comprises a band brake device or a gear locking mechanism.

Item 19: The torque balancing device of item 18, wherein the locking mechanism is an end face tooth engagement locking mechanism comprising:

an end face toothed disk fixed to the first body; and an end face tooth translation block movably arranged on the second body, a side of the end face tooth translation block close to the end face toothed disk having engaging teeth that mate with the end face toothed disk, and the end face tooth translation block being movable to engage with or disengage from the end face toothed disk.

Item 20: The torque balancing device of item 19, wherein the locking mechanism further comprises:

a retaining plate fixed to the second body and located on a side of the end face tooth translation block away from the end face toothed disk;

a guiding screw connected to the end face tooth translation block and the retaining plate;

an elastic member sleeved on the guiding screw, one end of the elastic member abutting against the retaining plate, and the other end of the elastic member abutting against the end face tooth translation block; and an unlocking control cable, one end of the unlocking control cable being connected to the end face tooth translation block.

Item 21: The torque balancing device of item 18, wherein the locking mechanism is a circumferential tooth engagement locking mechanism comprising:

a circumferential toothed disk fixed to the first body; and a circumferential tooth translation block slidably arranged on the second body, an axis of rotation of the second body being perpendicular to lengthwise directions of the first body and the second body, a side of the circumferential tooth translation block close to the circumferential toothed disk having engaging teeth that mate with the circumferential toothed disk, and the circumferential tooth translation block being slidable to engage with or disengage from the circumferential toothed disk.

Item 22: The torque balancing device of item 21, wherein the locking mechanism further comprises:

a retaining plate fixed to the second body and located on a side of the circumferential tooth translation block away from the circumferential toothed disk;

a guiding screw connected to the circumferential tooth translation block and the retaining plate;

an elastic member sleeved on the guiding screw, one end of the elastic member abutting against the retaining plate, and the other end of the elastic member abutting against the circumferential tooth translation block; and an unlocking control cable, one end of the unlocking control cable being connected to the circumferential tooth translation block.

Item 23: The torque balancing device of item 18, wherein the locking mechanism is a band brake device;

wherein the band brake device further comprises a band brake locking mechanism; and the band brake locking mechanism comprises:

an additional rod located above a multi-sheet layer of the band brake device and movably arranged on a rod of the band brake device; and an actuating component connected to the additional rod and configured to drive the additional rod to move in an axial direction of the rod of the band brake device, such that the additional rod compresses or releases a multi-sheet layer of the band brake device, the multi-sheet layer being configured to provide a frictional resistance to the band brake device when compressed by the additional rod.

Item 24: A self-balancing joint comprising a damping adjustment mechanism and a torque balancing device of any one of items 1-23.

Item 25: The self-balancing joint of item 24, wherein the damping adjustment mechanism comprises: a rotating part having an inner race and an outer race that are rotatable relative to each other, the outer race of the rotating part being connected to the first body;

a first friction part fixedly connected to the inner race of the rotating part and the second body;

a second friction part axially movably arranged on the first body and a friction interface being formed between the second friction part and the first friction part; and an adjustment part connected to the second friction part and configured to drive the second friction part to move closer to or away from the first friction part such that frictional damping at the friction interface between the second friction part and the first friction part increases or decreases.

Item 26: The self-balancing joint of item 25, wherein the rotating part comprises a crossed roller bearing, and the adjustment part comprises:

a retainer fixedly connected to the first body and the outer race of the crossed roller bearing;

a guiding member arranged in the retainer and movable along an axis of the crossed roller bearing; and a first elastic member with one end of the first elastic member abutting against the guiding member, and the other end of the first elastic member abutting against the second friction part.

Item 27: The self-balancing joint of item 24, wherein the damping adjustment mechanism comprises:

a guiding member arranged on the first body and movable in a radial direction of the first body;

a friction member radially movably arranged on the first body, the first body being connected to the second body by means a rotating shaft, the friction member being arranged outside the rotating shaft, and a friction interface being present between the friction member and the rotating shaft, and a gap being left between the friction member and the guiding member; and a second elastic member, one end of the second elastic member abutting against the guiding member, and the other end of the second elastic member abutting against the friction member.

Item 28: A surgical robot comprising at least one kinematic joint comprising a torque balancing device of any one of items 1-23;

or the kinematic joint comprising a self-balancing joint of any one of items 24-27.

Item 29: the surgical robot of item 28, further comprising a double-parallelogram linkage, wherein the kinematic joint is associated with an input end of the double-parallelogram linkage, an output end of the double-parallelogram linkage is configured to be connected to a surgical device in such a way that an axis of the surgical device always passes through a remote center of motion of the double-parallelogram linkage;

a first locking mechanism is provided between the kinematic joint and the input end of the double-parallelogram linkage and is configured to lock or unlock a rotation between the kinematic joint and the double-parallelogram linkage; or a second locking mechanism is provided on at least one articulated joint of the double-parallelogram linkage and is configured to lock or unlock a rotation between two links forming the articulated joint.

Item 30: The surgical robot of item 29, wherein the first locking mechanism is a band brake device or a gear locking mechanism; or the second locking mechanism is a band brake device or a gear locking mechanism.

It should be noted that the foregoing description is only exemplary embodiments of the present disclosure and the technical principles employed thereby. It will be understood by those skilled in the art that the present disclosure is not limited to the specific embodiments herein, and that various significant changes, rearrangements and substitutions can be made by those skilled in the art without departing from the scope of protection of the present disclosure. Therefore, although the present disclosure is described in detail with reference to the above embodiments, the present disclosure is not limited merely to the above embodiments. More other equivalent embodiments may also be devised without departing from the concept of the present disclosure, and the scope of protection of the present disclosure is determined by the appended claims.

The invention claimed is:

1. A torque balancing device, comprising:

a first body comprising a first connection end and a first opposite end opposite to the first connection end;

a second body comprising a second connection end and a second opposite end opposite to the second connection end, the second connection end of the second body being rotatably connected to the first connection end of the first body;

an elastic part arranged in the first body, wherein the elastic part comprises a mounting seat mounted on the first body, at least one sliding press block slidably arranged on the mounting seat, and at least one compression spring arranged between the mounting seat and the sliding press block; and a transmission part connected to the second body and the at least one sliding press block of the elastic part, the transmission part being configured to be driven by rotation of the second body relative to the first body thereby compressing the at least one compression spring by translational motion of the at least one sliding press block so as to generate a balancing torque, wherein the at least one compression spring comprises a first group of compression springs, and the at least one sliding press block comprises a first sliding press block, wherein the first group of compression springs are sleeved on guiding posts between the first sliding press block and a first wing plate of the mounting seat, one end of each of the first group of compression springs abuts against the first wing plate of the mounting seat, and the other end of each of the first group of compression springs abuts against the first sliding press block, wherein the at least one compression spring further comprises a second group of compression springs, and the elastic part further comprises a pair of sliding press plates, wherein the pair of sliding press plates are respectively slidably arranged on the guiding posts located on two sides of the first sliding press block, one end of each of the first group of compression springs and one end of each of the second group of compression springs respectively abut against the first and second wing plates of the mounting seat, and the other end of each of the first group of compression springs and the other end of each of the second group of compression springs respectively abut against the pair of sliding press plates, and wherein at least one limiting block is provided on a web plate of the mounting seat between the pair of sliding press plates.

2. The torque balancing device according to claim 1, wherein:

the at least one compression spring further comprises a second group of compression springs, and the at least one sliding press block further comprises a second sliding press block;

the second group of compression springs are sleeved on guiding posts between the second sliding press block and a second wing plate of the mounting seat, one end of each of the second group of compression springs abuts against the second wing plate of the mounting seat, and the other end of each of the second group of compression springs abuts against the second sliding press block; and at least one limiting block is provided on a web plate of the mounting seat between the first sliding press block and the second sliding press block.

3. The torque balancing device according to claim 1, wherein the transmission part is a pulley transmission mechanism, and the pulley transmission mechanism comprises:

an adapter block fixedly arranged at the second connection end of the second body;

a first pulley set; and a first traction rope located on one side of the adapter block, one end of the first traction rope being connected to the adapter block, the other end of the first traction rope being turned by the first pulley set and then being fixedly connected to the first wing plate of the mounting seat on the same side as the first traction rope, the first traction rope driving the first sliding press block to move by means of the first pulley set, and the first sliding press block driving the pair of sliding press plates to move.

4. The torque balancing device according to claim 3, wherein the pulley transmission mechanism further comprises:

a second pulley set; and a second traction rope located on the other side of the adapter block, one end of the second traction rope being connected to the adapter block, the other end of the second traction rope being turned by the second pulley set and then being fixedly connected to the second wing plate of the mounting seat on the same side as the second traction rope, the second traction rope driving the first sliding press block to move by means of the second pulley set, and the first sliding press block driving the pair of sliding press plates to move.

5. A self-balancing joint, comprising:

a damping adjustment mechanism and a torque balancing device, wherein the torque balancing device comprises:

a first body comprising a first connection end and a first opposite end opposite to the first connection end;

a second body comprising a second connection end and a second opposite end opposite to the second connection end, the second connection end of the second body being rotatably connected to the first connection end of the first body;

an elastic part arranged in the first body, wherein the elastic part comprises a mounting seat mounted on the first body, at least one sliding press block slidably arranged on the mounting seat, and at least one compression spring arranged between the mounting seat and the sliding press block; and a transmission part connected to the second body and the at least one sliding press block of the elastic part, the transmission part being configured to be driven by rotation of the second body relative to the first body thereby compressing the at least one compression spring by translational motion of the at least one sliding press block so as to generate a balancing torque, wherein the at least one compression spring comprises a first group of compression springs, and the at least one sliding press block comprises a first sliding press block, wherein the first group of compression springs are sleeved on guiding posts between the first sliding press block and a first wing plate of the mounting seat, one end of each of the first group of compression springs abuts against the first wing plate of the mounting seat, and the other end of each of the first group of compression springs abuts against the first sliding press block, wherein the at least one compression spring further comprises a second group of compression springs, and the elastic part further comprises a pair of sliding press plates, wherein the pair of sliding press plates are respectively slidably arranged on the guiding posts located on two sides of the first sliding press block, one end of each of the first group of compression springs and one end of each of the second group of compression springs respectively abut against the first and second wing plates of the mounting seat, and the other end of each of the first group of compression springs and the other end of each of the second group of compression springs respectively abut against the pair of sliding press plates, and wherein at least one limiting block is provided on a web plate of the mounting seat between the pair of sliding press plates.

6. The self-balancing joint according to claim 5, wherein:

the damping adjustment mechanism comprises: a rotating part having an inner race and an outer race that are rotatable relative to each other, the outer race of the rotating part being connected to the first body;

a first friction part fixedly connected to the inner race of the rotating part and the second body;

a second friction part axially movably arranged on the first body, and a friction interface being formed between the second friction part and the first friction part; and an adjustment part connected to the second friction part and configured to drive the second friction part to approach or move away from the first friction part such that frictional damping at the friction interface between the second friction part and the first friction part increases or decreases.

7. The self-balancing joint according to claim 6, wherein the rotating part comprises a crossed roller bearing, and the adjustment part comprises:

a retainer fixedly connected to the first body and the outer race of the crossed roller bearing;

a guiding member arranged in the retainer and movable along an axis of the crossed roller bearing; and a first elastic member with one end of the first elastic member abutting against the guiding member, and the other end of the first elastic member abutting against the second friction part.

8. A surgical robot, comprising:

at least one kinematic joint, the kinematic joint comprising a torque balancing device, wherein the torque balancing device comprises:

a first body comprising a first connection end and a first opposite end opposite to the first connection end;

a second body comprising a second connection end and a second opposite end opposite to the second connection end, the second connection end of the second body being rotatably connected to the first connection end of the first body;

an elastic part arranged in the first body, wherein the elastic part comprises a mounting seat mounted on the first body, at least one sliding press block slidably arranged on the mounting seat, and at least one compression spring arranged between the mounting seat and the sliding press block; and a transmission part connected to the second body and the at least one sliding press block of the elastic part, the transmission part being configured to be driven by rotation of the second body relative to the first body thereby compressing the at least one compression spring by translational motion of the at least one sliding press block so as to generate a balancing torque, wherein the at least one compression spring comprises a first group of compression springs, and the at least one sliding press block comprises a first sliding press block, wherein the first group of compression springs are sleeved on guiding posts between the first sliding press block and a first wing plate of the mounting seat, one end of each of the first group of compression springs abuts against the first wing plate of the mounting seat, and the other end of each of the first group of compression springs abuts against the first sliding press block, wherein the at least one compression spring further comprises a second group of compression springs, and the elastic part further comprises a pair of sliding press plates, wherein the pair of sliding press plates are respectively slidably arranged on the guiding posts located on two sides of the first sliding press block, one end of each of the first group of compression springs and one end of each of the second group of compression springs respectively abut against the first and second wing plates of the mounting seat, and the other end of each of the first group of compression springs and the other end of each of the second group of compression springs respectively abut against the pair of sliding press plates, and wherein at least one limiting block is provided on a web plate of the mounting seat between the pair of sliding press plates.

* * * * *